United States Patent
Pechan et al.

(10) Patent No.: US 10,821,193 B2
(45) Date of Patent: Nov. 3, 2020

(54) ADENO-ASSOCIATED VIRAL VECTORS FOR TREATING MYOCILIN (MYOC) GLAUCOMA

(71) Applicant: Genzyme Corporation, Cambridge, MA (US)

(72) Inventors: Peter Pechan, Newton, MA (US); Abraham Scaria, Framingham, MA (US); Jeffery Ardinger, Bridgewater, NJ (US)

(73) Assignee: GENZYME CORPORATION, Cambridge, MA (US)

(*) Notice: Subject to any disclaimer, the term of this patent is extended or adjusted under 35 U.S.C. 154(b) by 298 days.

(21) Appl. No.: 15/511,595

(22) PCT Filed: Sep. 16, 2015

(86) PCT No.: PCT/US2015/050515
§ 371 (c)(1),
(2) Date: Mar. 15, 2017

(87) PCT Pub. No.: WO2016/044478
PCT Pub. Date: Mar. 24, 2016

(65) Prior Publication Data
US 2017/0304465 A1  Oct. 26, 2017

Related U.S. Application Data

(60) Provisional application No. 62/051,299, filed on Sep. 16, 2014.

(51) Int. Cl.
| | |
|---|---|
| *C12N 15/864* | (2006.01) |
| *A61K 48/00* | (2006.01) |
| *C07K 14/47* | (2006.01) |
| *C12N 15/113* | (2010.01) |
| *C12N 7/00* | (2006.01) |
| *C12N 15/86* | (2006.01) |
| *C12N 15/11* | (2006.01) |
| *A61K 9/00* | (2006.01) |
| *A61K 38/17* | (2006.01) |
| *C12N 15/12* | (2006.01) |

(52) U.S. Cl.
CPC ........ *A61K 48/0058* (2013.01); *A61K 9/0048* (2013.01); *A61K 38/1709* (2013.01); *C07K 14/47* (2013.01); *C12N 7/00* (2013.01); *C12N 15/111* (2013.01); *C12N 15/113* (2013.01); *C12N 15/86* (2013.01); *A61K 48/0075* (2013.01); *C12N 2310/14* (2013.01); *C12N 2310/531* (2013.01); *C12N 2320/31* (2013.01); *C12N 2330/51* (2013.01); *C12N 2750/14132* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 2005/0130145 A1 | 6/2005 | Yue et al. | |
| 2007/0087989 A1* | 4/2007 | Huang | A61K 9/0048 514/44 A |
| 2013/0209473 A1* | 8/2013 | de Sauvage | A61K 39/39558 424/139.1 |
| 2014/0044713 A1* | 2/2014 | De Lau | C07K 14/475 424/134.1 |
| 2014/0199277 A1* | 7/2014 | Cosma | C12N 5/0606 424/93.7 |
| 2015/0126588 A1* | 5/2015 | Nakai | C07K 14/005 514/44 R |

FOREIGN PATENT DOCUMENTS

| | | |
|---|---|---|
| JP | 2014-518614 A | 8/2014 |
| WO | WO-2005/079815 A2 | 9/2005 |
| WO | WO-2005/117938 A2 | 12/2005 |
| WO | WO-2008/075796 A1 | 6/2008 |
| WO | WO-2009/046059 A1 | 4/2009 |
| WO | WO-2012/145601 A2 | 10/2012 |

OTHER PUBLICATIONS

Fumoto et al, Targeted Gene Delivery: Importance of Administration Routes, Chapter 1, Intech, 2013, pp. 3-31.*
Atkas et al, Proteasome Inhibition Increases the Efficiency of Lentiviral Vector-Mediated Transduction of Trabecular Meshwork, Invest Ophthalmol Vis Sci. 2018;59:298-310.*
Liu et al, Gene Therapy Targeting Glaucoma: Where Are We?, Sury Ophthalmol. 2009 ; 54(4): 472-486.*
Selot, Developing Immunologically Inert Adeno-Associated Virus (AAV) Vectors for Gene Therapy: Possibilities and Limitations, Curr Phar Biotech, 2013, pp. 1-11.*
Bemelmans et al, A Single Intravenous AAV9 Injection Mediates Bilateral Gene Transfer to the Adult Mouse Retina, PLOS ONE, 2013, pp. 1-9.*
Shen et al, Wnt Activation by Wild Type and Mutant Myocilin in Cultured Human Trabecular Meshwork Cells, PLOS ONE, 2012, pp. 1-10.*
Buie, L.K. et al. (Jan. 1, 2010). "Self-complementary AAV Virus (scAAV) Safe and Long Long-Term Gene Transfer in the Trabecular Meshwork of Living Rats and Monkeys," *Investigative Opthalmology & Visual Science* 51 (1):236.

(Continued)

*Primary Examiner* — Maria Marvich
(74) *Attorney, Agent, or Firm* — Morrison & Foerster LLP

(57) ABSTRACT

Provided herein are methods for treating myocilin (MYOC) glaucoma using adeno-associated viral (AAV) vectors. In some aspects, the AAV vectors encode R-spondin 1 (RSPO1), R-spondin 2 (RSPO2), R-spondin 3 (RSPO3) or R-spondin 4 (RSPO4) and/or RNAi that targets myocilin (MYOC). In one aspect, viral particles are administered to the eye of a human subject. Viral particles encoding RSPO1, RSPO2, RSPO3 and/or RSPO4 and/or MYOC RNAi are contemplated. In some aspects, variant AAV2 particles that transduce the trabecular meshwork are provided.

61 Claims, 14 Drawing Sheets

Specification includes a Sequence Listing.

(56) References Cited

OTHER PUBLICATIONS

Kim, K.A. et al. (Jun. 1, 2008, e-pub. Apr. 9, 2008). "R-Spondin Family Members Regulate the Wnt Pathway by a Common Mechanism," *Molecular Biology of the Cell* 19(6):2588-2596.

Kwon, H-S. et al. (Apr. 15, 2009). "Myocilin is a Modulator of Wnt Signaling," *Molecular and Cellular Biology* 29(8):2139-2154.

Lochrie, M.A. et al. (Jan. 1, 2006). "Mutations on the External Surfaces of Adeno-Associated Virus Type 2 Capsids that Affect Transduction and Neutralization," *Journal of Virology* 80(2):821-834.

Bennicelli, J. et al. (Mar. 2008, e-pub. Jan. 22, 2008). "Reversal of Blindness in Animal Models of Leber Congenital Amaurosis Using Optimized AAV2-mediated Gene Transfer," The American Society of Gene Therapy 16(3):458-465.

Pechan, P. et al. (Jun. 2015). "Role of Myocilin Mutants and Wnt Signaling in Glaucoma," BIOSIS 56(7):1973, 2 pages.

\* cited by examiner

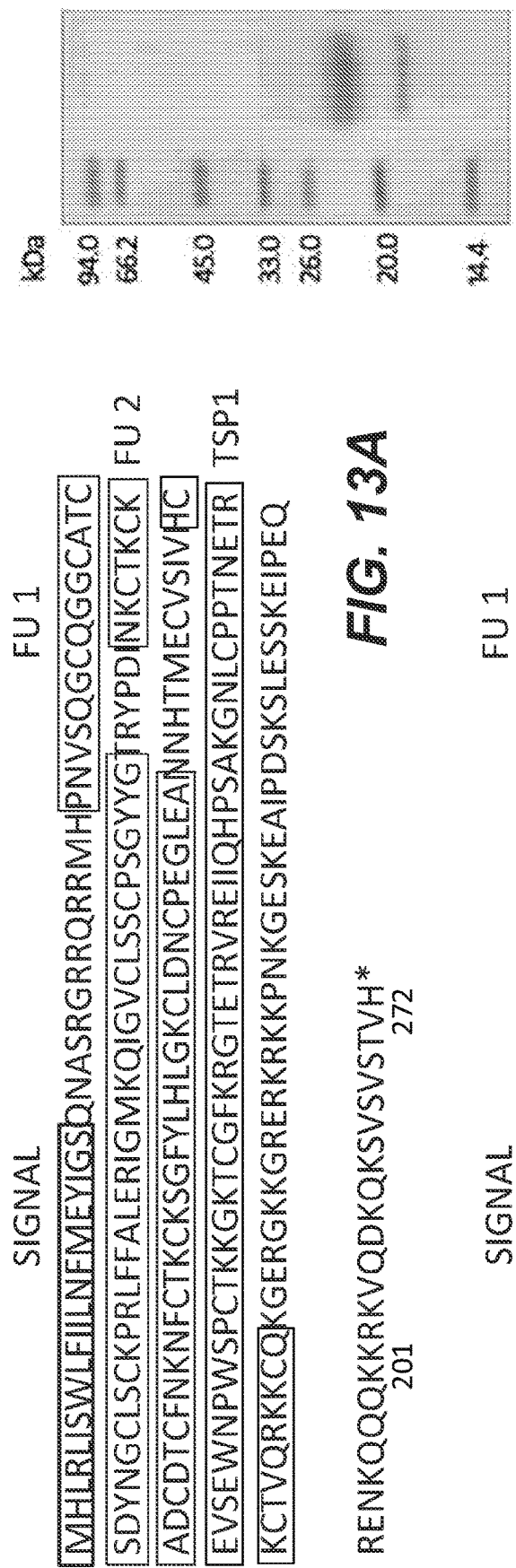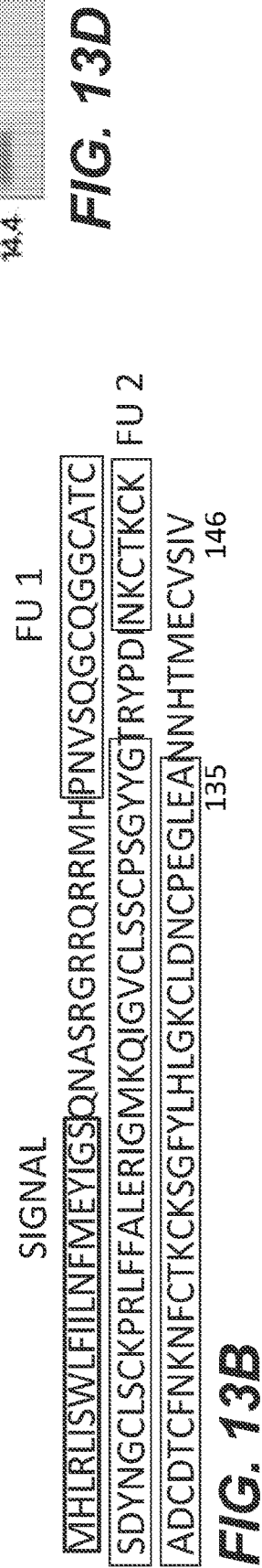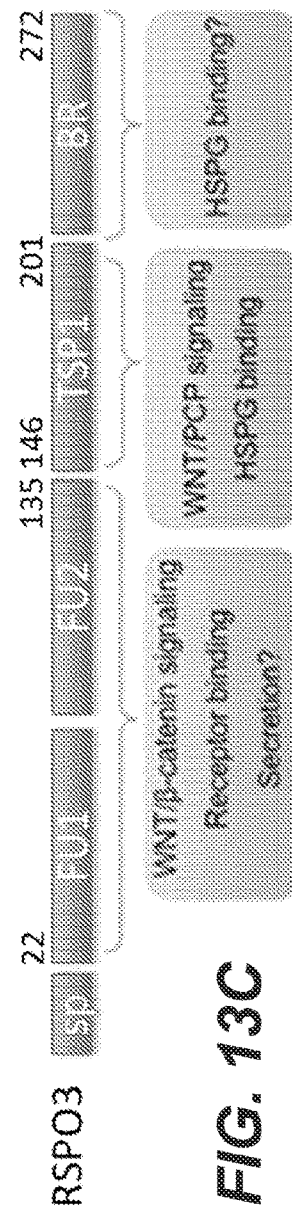
FIG. 13D
FIG. 13A
FIG. 13B
FIG. 13C

SEQUENCE LISTING

<160> NUMBER OF SEQ ID NOS: 24

<210> SEQ ID NO 1
<211> LENGTH: 272
<212> TYPE: PRT
<213> ORGANISM: Homo sapiens

<400> SEQUENCE: 1

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Cys Ala Thr Cys
            35                  40                  45

Ser Asp Tyr Asn Gly Cys Leu Ser Cys Lys Pro Arg Leu Phe Phe Ala
        50                  55                  60

Leu Glu Arg Ile Gly Met Lys Gln Ile Gly Val Cys Leu Ser Ser Cys
65              70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
        130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Pro Asn
        210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Lys Lys
                245                 250                 255

Arg Lys Val Gln Asp Lys Gln Lys Ser Val Ser Val Ser Thr Val His
            260                 265                 270
```

<210> SEQ ID NO 2
<211> LENGTH: 819
<212> TYPE: DNA
<213> ORGANISM: Homo sapiens

<400> SEQUENCE: 2

```
atgcacttgc gactgatttc ttggcttttt atcatttga actttatgga atacatcggc      60
agccaaaacg cctcccgggg aaggcgccag cgaagaatgc atcctaacgt tagtcaaggc    120
tgccaaggag gctgtgcaac atgctcagat tacaatggga gtttgtcatg taagcccaga    180
ctattttttg ctctggaaag aattggcatg aagcagattg gagtatgtct ctcttcatgt    240
ccaagtggat attatggaac tcgatatcca gatataaata gtgtacaaa  atgcaaagct    300
gactgtgata cctgtttcaa caaaaatttc tgcacaaaat gtaaaagtgg attttactta    360
caccttggaa agtgccttga caattgccca gaagggttgg aagccaacaa ccatactatg    420
gagtgtgtca gtattgtgca ctgtgaggtc agtgaatgga atccttggag tccatgcacg    480
aagaagggaa aaacatgtgg cttcaaaaga gggactgaaa cacgggtccg agaaataata    540
cagcatcctt cagcaaaggg taacctgtgt cccccaacaa atgagacaag aaagtgtaca    600
gtgcaaagga gaagtgtca  gaagggagaa cgaggaaaaa aaggaaggga gaggaaaaga    660
aaaaaaccta ataaaggaga agtaaagaa  gcaatacctg acagcaaaag tctggaatcc    720
agcaaagaaa tcccagagca acgagaaaac aaacagcagc agaagaagcg aaaagtccaa    780
gataaacaga atcggtatc  agtcagcact gtacactag                           819
```

<210> SEQ ID NO 3
<211> LENGTH: 502
<212> TYPE: PRT
<213> ORGANISM: Homo sapiens

<400> SEQUENCE: 3

```
Met Arg Phe Phe Cys Ala Arg Cys Cys Ser Phe Gly Pro Glu Met Pro
1               5                   10                  15

Ala Val Gln Leu Leu Leu Ala Cys Leu Val Trp Asp Val Gly Ala
            20                  25                  30

Arg Thr Ala Gln Leu Arg Lys Ala Asn Asp Gln Ser Gly Arg Cys Gln
        35                  40                  45

Tyr Thr Phe Ser Val Asp Asn Glu Ser Ser Cys Pro Glu Gln Ser Gln
    50                  55                  60

Ala Met Ser Val Ile His Asn Leu Gln Arg Asp Ser Ser Thr Gln Arg
65                  70                  75                  80

Leu Asp Leu Glu Ala Thr Lys Ala Arg Leu Ser Ser Leu Glu Ser Leu
                85                  90                  95

Leu His Gln Leu Thr Leu Asp Gln Ala Ala Arg Pro Gln Glu Thr Gln
            100                 105                 110

Glu Gly Leu Gln Arg Glu Leu Gly Thr Leu Arg Arg Glu Arg Asp Gln
        115                 120                 125

Leu Glu Thr Gln Thr Arg Glu Leu Glu Thr Ala Tyr Ser Asn Leu Leu
    130                 135                 140

Arg Asp Lys Ser Val Leu Glu Glu Glu Lys Lys Arg Leu Arg Gln Glu
145                 150                 155                 160

Asn Glu Asn Leu Ala Arg Arg Leu Glu Ser Ser Ser Gln Glu Val Ala
                165                 170                 175

Arg Leu Arg Arg Gly Gln Cys Pro Gln Thr Arg Asp Thr Ala Arg Ala
            180                 185                 190
```

Val Pro Pro Gly Ser Arg Glu Val Ser Thr Trp Asn Leu Asp Thr Leu
            195                 200                 205

Ala Phe Gln Glu Leu Lys Ser Glu Leu Thr Glu Val Pro Ala Ser Arg
210                 215                 220

Ile Leu Lys Glu Ser Pro Ser Gly Tyr Leu Arg Ser Gly Glu Gly Asp
225                 230                 235                 240

Thr Gly Cys Gly Glu Leu Val Trp Val Gly Glu Pro Leu Thr Leu Arg
            245                 250                 255

Thr Ala Glu Thr Ile Thr Gly Lys Tyr Gly Val Trp Met Arg Asp Pro
                260                 265                 270

Lys Pro Thr Tyr Pro Tyr Thr Gln Glu Thr Thr Trp Arg Ile Asp Thr
            275                 280                 285

Val Gly Thr Asp Val Arg Gln Val Phe Glu Tyr Asp Leu Ile Ser Gln
290                 295                 300

Phe Met Gln Gly Tyr Pro Ser Lys Val His Ile Leu Pro Arg Pro Leu
305                 310                 315                 320

Glu Ser Thr Gly Ala Val Val Tyr Ser Gly Ser Leu Tyr Phe Gln Gly
            325                 330                 335

Ala Glu Ser Arg Thr Val Ile Arg Tyr Glu Leu Asn Thr Glu Thr Val
                340                 345                 350

Lys Ala Glu Lys Glu Ile Pro Gly Ala Gly Tyr His Gly Gln Phe Pro
            355                 360                 365

Tyr Ser Trp Gly Gly Tyr Thr Asp Ile Asp Leu Ala Val Asp Glu Ala
370                 375                 380

Gly Leu Trp Val Ile Tyr Ser Thr Asp Glu Ala Lys Gly Ala Ile Val
385                 390                 395                 400

Leu Ser Lys Leu Asn Pro Glu Asn Leu Glu Leu Glu Gln Thr Trp Glu
            405                 410                 415

Thr Asn Ile Arg Lys Gln Ser Val Ala Asn Ala Phe Ile Ile Cys Gly
                420                 425                 430

Thr Leu Tyr Thr Val Ser Ser Tyr Thr Ser Ala Asp Ala Thr Val Asn
            435                 440                 445

Phe Ala Tyr Asp Thr Gly Thr Gly Ile Ser Lys Thr Leu Thr Ile Pro
450                 455                 460

Phe Lys Asn Arg Tyr Lys Tyr Ser Ser Met Ile Asp Tyr Asn Pro Leu
465                 470                 475                 480

Glu Lys Lys Leu Phe Ala Trp Asp Asn Leu Asn Met Val Thr Tyr Asp
            485                 490                 495

Ile Lys Leu Ser Lys Met
            500

<210> SEQ ID NO 4
<211> LENGTH: 1515
<212> TYPE: DNA
<213> ORGANISM: Artificial Sequence
<220> FEATURE:
<223> OTHER INFORMATION: Synthetic Construct

<400> SEQUENCE: 4
atgaggttct tctgtgcacg ttgctgcagc tttgggcctg agatgccagc tgtccagctg        60
ctgcttctgg cctgcctggt gtgggatgtg ggggccagga cagctcagct caggaaggcc       120
aatgaccaga gtggccgatg ccagtatacc ttcagtgtgg ccagtcccaa tgaatccagc       180
tgcccagaga gagccaggc catgtcagtc atccataact acagagaga cagcagcacc         240 caacgcttag acctggaggc caccaaagct cgactcagct ccctggagag cctcctccac       300

```
caattgacct tggaccaggc tgccaggccc caggagaccc aggaggggct gcagagggag      360
ctgggcaccc tgaggcggga gcgggaccag ctggaaaccc aaaccagaga gttggagact      420
gcctacagca acctcctccg agacaagtca gttctggagg aagagaagaa gcgactaagg      480
caagaaaatg agaatctggc caggaggttg gaaagcagca gccaggaggt agcaaggctg      540
agaaggggcc agtgtcccca gacccgagac actgctcggg ctgtgccacc aggctccaga      600
gaagtttcta cgtggaattt ggacactttg gccttccagg aactgaagtc cgagctaact      660
gaagttcctg cttcccgaat tttgaaggag agcccatctg gctatctcag gagtggagag      720
ggagacaccg gatgtggaga actagtttgg gtaggagagc ctctcacgct gagaacagca      780
gaaacaatta ctggcaagta tggtgtgtgg atgcgagacc ccaagcccac ctacccctac      840
acccaggaga ccacgtggag aatcgacaca gttggcacgg atgtccgcca ggttttttgag     900 tatgacctca tcagccagtt tatgcagggc tacccttcta aggttcacat actgcctagg      960
ccactggaaa gcacgggtgc tgtggtgtac tcggggagcc tctatttcca gggcgctgag     1020
tccagaactg tcataagata tgagctgaat accgagacag tgaaggctga aaggaaatc      1080 cctggagctg gctaccacgg acagttcccg tattcttggg gtggctacac ggacattgac     1140
ttggctgtgg atgaagcagg cctctgggtc atttacagca ccgatgaggc caaaggtgcc     1200
attgtcctct ccaaactgaa cccagagaat ctggaactcg aacaaacctg ggagacaaac     1260
atccgtaagc agtcagtcgc caatgccttc atcatctgtg gcaccttgta caccgtcagc     1320
agctacacct cagcagatgc taccgtcaac tttgcttatg acacaggcac aggtatcagc     1380
aagaccctga ccatcccatt caagaaccgc tataagtaca gcagcatgat tgactacaac     1440
cccctggaga agaagctctt tgcctgggac aacttgaaca tggtcactta tgacatcaag     1500
ctctccaaga tgtag                                                      1515

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
ggccatgtca gtcatccat                                                    19

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Gln Ala Met Ser Val Ile His
1               5

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
aatagtgaag ccacagatgt att                                               23
```

<210> SEQ ID NO 8
<211> LENGTH: 259
<212> TYPE: PRT
<213> ORGANISM: Homo sapiens

<400> SEQUENCE: 8

Met Arg Leu Gly Leu Cys Val Val Leu Ser Trp Thr His Leu Thr
1               5                   10                  15

Ile Ser Ser Arg Gly Ile Lys Gly Lys Arg Gln Arg Ile Ser Ala
                20                  25                  30

Glu Gly Ser Gln Ala Cys Ala Lys Gly Cys Glu Leu Cys Ser Glu Val
                35                  40                  45

Asn Gly Cys Leu Lys Cys Ser Pro Lys Leu Phe Ile Leu Leu Glu Arg
    50                  55                      60

Asn Asp Ile Arg Gln Val Gly Val Cys Leu Pro Ser Cys Pro Pro Gly
65                  70                  75                  80

Tyr Phe Asp Ala Arg Asn Pro Asp Met Asn Lys Cys Ile Lys Cys Lys
                    85                  90                  95

Ile Glu His Cys Glu Ala Cys Phe Ser His Asn Phe Cys Thr Lys Cys
                100                 105                 110

Lys Glu Gly Leu His Lys Gly Arg Cys Tyr Pro Ala Cys Pro Glu Gly
                115                 120                 125

Ser Ser Ala Ala Asn Gly Thr Met Glu Cys Ser Ser Pro Ala Gln Cys
    130                 135                 140

Glu Met Ser Glu Trp Ser Pro Trp Gly Pro Cys Ser Lys Lys Gln Gln
145                 150                 155                 160

Leu Cys Gly Phe Arg Arg Gly Ser Glu Glu Arg Thr Arg Arg Val Leu
                165                 170                 175

His Ala Pro Val Gly Asp His Ala Ala Cys Ser Asp Thr Lys Glu Thr
                180                 185                 190

Arg Arg Cys Thr Val Arg Arg Val Pro Cys Pro Glu Gly Gln Lys Arg
                195                 200                 205

Arg Lys Gly Gly Gln Gly Arg Arg Glu Asn Ala Asn Arg Asn Leu Ala
    210                 215                 220

Arg Lys Glu Ser Lys Glu Ala Gly Ala Gly Ser Arg Arg Arg Lys Gly
225                 230                 235                 240

Gln Gln Gln Gln Gln Gln Gly Thr Val Gly Pro Leu Thr Ser Ala
                245                 250                 255

Gly Pro Ala

<210> SEQ ID NO 9
<211> LENGTH: 243
<212> TYPE: PRT
<213> ORGANISM: Homo sapiens

<400> SEQUENCE: 9

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
                20                  25                  30

Ser Tyr Val Ser Asn Pro Ile Cys Lys Gly Cys Leu Ser Cys Ser Lys
                35                  40                  45

Asp Asn Gly Cys Ser Arg Cys Gln Gln Lys Leu Phe Phe Phe Leu Arg
    50                  55                      60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
210                 215                 220

Ile Glu Arg Ala Gln Glu Gln His Ser Val Phe Leu Ala Thr Asp Arg
225                 230                 235                 240

Ala Asn Gln

<210> SEQ ID NO 10
<211> LENGTH: 234
<212> TYPE: PRT
<213> ORGANISM: Homo sapiens

<400> SEQUENCE: 10

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

```
Gln Arg Pro Cys Pro Gly Glu Arg Ser Pro Gly Gln Lys Gly Arg
        195                 200                 205

Lys Asp Arg Arg Pro Arg Lys Asp Arg Lys Leu Asp Arg Arg Leu Asp
        210                 215                 220

Val Arg Pro Arg Gln Pro Gly Leu Gln Pro
225                 230

<210> SEQ ID NO 11
<211> LENGTH: 131
<212> TYPE: PRT
<213> ORGANISM: Artificial Sequence
<220> FEATURE:
<223> OTHER INFORMATION: Synthetic Construct

<400> SEQUENCE: 11

Met Arg Leu Gly Leu Cys Val Val Leu Ser Trp Thr His Leu Thr
1               5                   10                  15

Ile Ser Ser Arg Gly Ile Lys Gly Lys Arg Gln Arg Ile Ser Ala
                20                  25                  30

Glu Gly Ser Gln Ala Cys Ala Lys Gly Cys Glu Leu Cys Ser Glu Val
            35                  40                  45

Asn Gly Cys Leu Lys Cys Ser Pro Lys Leu Phe Ile Leu Leu Glu Arg
50                  55                  60

Tyr Phe Asp Ala Arg Asn Pro Asp Met Asn Lys Cys Ile Lys Cys Lys
                85                  90                  95

Ile Glu His Cys Glu Ala Cys Phe Ser His Asn Phe Cys Thr Lys Cys
            100                 105                 110

Lys Glu Gly Leu His Lys Gly Arg Cys Tyr Pro Ala Cys Pro Glu Gly
            115                 120                 125

Ser Ser Ala
    130

<210> SEQ ID NO 12
<211> LENGTH: 202
<212> TYPE: PRT
<213> ORGANISM: Artificial Sequence
<220> FEATURE:
<223> OTHER INFORMATION: Synthetic Construct

<400> SEQUENCE: 12

Met Arg Leu Gly Leu Cys Val Val Leu Ser Trp Thr His Leu Thr
1               5                   10                  15

Ile Ser Ser Arg Gly Ile Lys Gly Lys Arg Gln Arg Ile Ser Ala
                20                  25                  30

Glu Gly Ser Gln Ala Cys Ala Lys Gly Cys Glu Leu Cys Ser Glu Val
            35                  40                  45

Asn Gly Cys Leu Lys Cys Ser Pro Lys Leu Phe Ile Leu Leu Glu Arg
50                  55                  60

Asn Asp Ile Arg Gln Val Gly Val Cys Leu Pro Ser Cys Pro Pro Gly
65                  70                  75                  80

Tyr Phe Asp Ala Arg Asn Pro Asp Met Asn Lys Cys Ile Lys Cys Lys
                85                  90                  95

Ile Glu His Cys Glu Ala Cys Phe Ser His Asn Phe Cys Thr Lys Cys
            100                 105                 110

Lys Glu Gly Leu His Lys Gly Arg Cys Tyr Pro Ala Cys Pro Glu Gly
            115                 120                 125
```

```
Ser Ser Ala Ala Asn Gly Thr Met Glu Cys Ser Ser Pro Ala Gln Cys
    130                 135                 140

Glu Met Ser Glu Trp Ser Pro Trp Gly Pro Cys Ser Lys Lys Gln Gln
145                 150                 155                 160

Leu Cys Gly Phe Arg Arg Gly Ser Glu Glu Arg Thr Arg Arg Val Leu
                165                 170                 175

His Ala Pro Val Gly Asp His Ala Ala Cys Ser Asp Thr Lys Glu Thr
            180                 185                 190

Arg Arg Cys Thr Val Arg Val Pro Cys
            195                 200

<210> SEQ ID NO 13
<211> LENGTH: 134
<212> TYPE: PRT
<213> ORGANISM: Artificial Sequence
<220> FEATURE:
<223> OTHER INFORMATION: Synthetic Construct

<400> SEQUENCE: 13

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro
    130

<210> SEQ ID NO 14
<211> LENGTH: 203
<212> TYPE: PRT
<213> ORGANISM: Artificial Sequence
<220> FEATURE:
<223> OTHER INFORMATION: Synthetic Construct

<400> SEQUENCE: 14

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
```

```
                    85                  90                  95

Arg Ile Glu Asn Cys Asp Ser Cys Phe Ser Lys Asp Phe Cys Thr Lys
                100                 105                 110

Cys Lys Val Gly Phe Tyr Leu His Arg Gly Arg Cys Phe Asp Glu Cys
            115                 120                 125

Pro Asp Gly Phe Ala Pro Leu Glu Glu Thr Met Glu Cys Val Glu Gly
        130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys
        195                 200

<210> SEQ ID NO 15
<211> LENGTH: 135
<212> TYPE: PRT
<213> ORGANISM: Artificial Sequence
<220> FEATURE:
<223> OTHER INFORMATION: Synthetic Construct

<400> SEQUENCE: 15

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala
    130                 135

<210> SEQ ID NO 16
<211> LENGTH: 146
<212> TYPE: PRT
<213> ORGANISM: Artificial Sequence
<220> FEATURE:
<223> OTHER INFORMATION: Synthetic Construct

<400> SEQUENCE: 16

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45
```

```
Ser Asp Tyr Asn Gly Cys Leu Ser Cys Lys Pro Arg Leu Phe Phe Ala
     50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
                100                 105                 110

Lys Cys Lys Ser Gly Phe Tyr Leu His Leu Gly Lys Cys Leu Asp Asn
                115                 120                 125

Cys Pro Glu Gly Leu Glu Ala Asn Asn His Thr Met Glu Cys Val Ser
130                 135                 140

Ile Val
145

<210> SEQ ID NO 17
<211> LENGTH: 206
<212> TYPE: PRT
<213> ORGANISM: Artificial Sequence
<220> FEATURE:
<223> OTHER INFORMATION: Synthetic Construct

<400> SEQUENCE: 17

Met His Leu Arg Leu Ile Ser Trp Leu Phe Ile Ile Leu Asn Phe Met
 1               5                  10                  15

Glu Tyr Ile Gly Ser Gln Asn Ala Ser Arg Gly Arg Gln Arg Arg
                 20                  25                  30

Met His Pro Asn Val Ser Gln Gly Cys Gln Gly Gly Cys Ala Thr Cys
                 35                  40                  45

Ser Asp Tyr Asn Gly Cys Leu Ser Cys Lys Pro Arg Leu Phe Phe Ala
     50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
                100                 105                 110

Lys Cys Lys Ser Gly Phe Tyr Leu His Leu Gly Lys Cys Leu Asp Asn
                115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
                180                 185                 190

Thr Asn Glu Thr Arg Lys Cys Thr Val Gln Arg Lys Lys Cys
                195                 200                 205

<210> SEQ ID NO 18
<211> LENGTH: 128
<212> TYPE: PRT
<213> ORGANISM: Artificial Sequence
<220> FEATURE:
<223> OTHER INFORMATION: Synthetic Construct

<400> SEQUENCE: 18
```

```
Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
            115                 120                 125
```

<210> SEQ ID NO 19
<211> LENGTH: 195
<212> TYPE: PRT
<213> ORGANISM: Artificial Sequence
<220> FEATURE:
<223> OTHER INFORMATION: Synthetic Construct

<400> SEQUENCE: 19

```
Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
            115                 120                 125

His Gln Asn Thr Arg Glu Cys Gln Gly Glu Cys Glu Leu Gly Pro Trp
            130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro
        195
```

<210> SEQ ID NO 20
<211> LENGTH: 78
<212> TYPE: DNA
<213> ORGANISM: Artificial Sequence

```
<220> FEATURE:
<223> OTHER INFORMATION: Synthetic Construct

<400> SEQUENCE: 20
cactccctct ctgcgcgctc gctcgctcac tgaggccggg cgaccaaagg tcgcccacgc      60
ccgggctttg cccgggcg                                                    78

<210> SEQ ID NO 21
<211> LENGTH: 31
<212> TYPE: DNA
<213> ORGANISM: Artificial Sequence
<220> FEATURE:
<223> OTHER INFORMATION: Synthetic Construct

<400> SEQUENCE: 21
accacggaca gttcctgtat tcttggggtg g                                     31

<210> SEQ ID NO 22
<211> LENGTH: 31
<212> TYPE: DNA
<213> ORGANISM: Artificial Sequence
<220> FEATURE:
<223> OTHER INFORMATION: Synthetic Construct

<400> SEQUENCE: 22
ccaccccaag aatacaggaa ctgtccgtgg t                                     31

<210> SEQ ID NO 23
<211> LENGTH: 29
<212> TYPE: DNA
<213> ORGANISM: Artificial Sequence
<220> FEATURE:
<223> OTHER INFORMATION: Synthetic Construct

<400> SEQUENCE: 23
tctgtggcac cttgcacacc gtcagcagc                                        29

<210> SEQ ID NO 24
<211> LENGTH: 29
<212> TYPE: DNA
<213> ORGANISM: Artificial Sequence
<220> FEATURE:
<223> OTHER INFORMATION: Synthetic Construct

<400> SEQUENCE: 24
gctgctgacg gtgtgcaagg tgccacaga                                        29
```

ADENO-ASSOCIATED VIRAL VECTORS FOR TREATING MYOCILIN (MYOC) GLAUCOMA

CROSS-REFERENCE TO RELATED APPLICATIONS

This application is a National Phase application under 35 U.S.C. § 371 of International Application No. PCT/US2015/050515 filed Sep. 16, 2015, which claims priority benefit of U.S. Provisional Application No. 62/051,299, filed Sep. 16, 2014, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792012500SEQLIST.txt, date recorded: Mar. 15, 2017, size: 31 KB).

FIELD OF THE INVENTION

The present invention relates to AAV vectors and methods of using AAV vectors for treating myocilin (MYOC) glaucoma.

BRIEF SUMMARY OF THE INVENTION

Myocilin (MYOC) mutations account for about 2%-4% of primary open-angle glaucoma (POAG; ~90,000 U.S. patients). In particular, glaucomatous MYOC mutations P370L or Y437H account for 10%-30% of the juvenile form of POAG (JOAG; ~6,000 U.S. patients) and are associated with increased intraocular pressure (IOP), retinal ganglion cell death, and optic nerve head (ONH) damage (Shimizu et al. (2000) *Am. J. Ophthalmol.* 130:165-77; Fan and Wiggs (2010) *J. Clin. Invest.* 120:3064-72).

Despite the association between MYOC mutations and glaucoma, the effect of MYOC mutants on eye function remains unclear. Accordingly, further understanding of MYOC and mutant MYOC function is needed to uncover new therapeutic strategies for treating myocilin (MYOC) glaucoma.

The invention provides methods for treating myocilin (MYOC) glaucoma in a mammal, comprising administering to the eye of the mammal an agent that increases Wnt signaling in the eye of the mammal. In some embodiments, the agent increases Wnt signaling in a trabecular meshwork (TM) cell of the eye of the mammal. In some embodiments, the agent increases R-spondin 1 (RSPO1), R-spondin 2 (RSPO2), R-spondin 3 (RSPO3), and/or R-spondin 4 (RSPO4) activity in the eye of the mammal. In some embodiments, the agent is used in combination with one or more additional agents that increase one or more RSPO activities in the eye of the mammal. In some embodiments, the agent increases RSPO1 in the TM of the eye of the mammal. In some embodiments, the agent is RSPO1 or a functional variant thereof. In some embodiments, the agent is a recombinant adeno-associated virus (rAAV) particle comprising a vector encoding RSPO1 or a functional variant thereof. In some embodiments, the RSPO1 is a truncated RSPO1. In some embodiments, the agent increases RSPO2 in the TM of the eye of the mammal. In some embodiments, the agent is RSPO2 or a functional variant thereof. In some embodiments, the agent is a recombinant adeno-associated virus (rAAV) particle comprising a vector encoding RSPO2 or a functional variant thereof. In some embodiments, the RSPO2 is a truncated RSPO2. In some embodiments, the agent increases RSPO3 in the TM of the eye of the mammal. In some embodiments, the agent is RSPO3 or a functional variant thereof. In some embodiments, the agent is a recombinant adeno-associated virus (rAAV) particle comprising a vector encoding RSPO3 or a functional variant thereof. In some embodiments, the RSPO3 is a truncated RSPO3. In some embodiments, the agent increases RSPO4 in the TM of the eye of the mammal. In some embodiments, the agent is RSPO4 or a functional variant thereof. In some embodiments, the agent is a recombinant adeno-associated virus (rAAV) particle comprising a vector encoding RSPO4 or a functional variant thereof. In some embodiments, the RSPO4 is a truncated RSPO4.

In some aspects, the invention provides administering a second agent that increases Wnt signaling in the eye of the mammal. In some embodiments, the second agent increases Wnt signaling in the TM of the eye of the mammal. In some embodiments, the second agent reduces or inhibits expression of myocilin (MYOC) in the eye of the mammal. In some embodiments, the second agent reduces or inhibits expression of MYOC in the TM of the eye of the mammal. In some embodiments, the second agent is a recombinant adeno-associated virus (rAAV) particle comprising a vector encoding an inhibitory nucleic acid that targets expression of MYOC. In some embodiments, the inhibitory nucleic acid is a MYOC RNAi that targets expression of MYOC. In some embodiments, the MYOC RNAi is MYOC shRNA that targets expression of MYOC.

In some aspects, the agent of the invention reduces or inhibits expression of myocilin (MYOC) in the eye of the mammal. In some embodiments, the agent reduces or inhibits expression of MYOC in the TM of the eye of the mammal. In some embodiments, the agent is a recombinant adeno-associated virus (rAAV) particle comprising a vector encoding an inhibitory nucleic acid that targets expression of MYOC. In some embodiments, the inhibitory nucleic acid is a MYOC RNAi that targets expression of MYOC. In further embodiments, the MYOC RNAi is MYOC shRNA that targets expression of MYOC.

In some embodiments of the invention, the methods further comprise administering a second agent that increases Wnt signaling in the eye of the mammal. In some embodiments, the second agent increases Wnt signaling in the TM of the eye of the mammal. In some embodiments, the second agent increases R-spondin 1 (RSPO1), R-spondin 2 (RSPO2), R-spondin 3 (RSPO3), or R-spondin 4 (RSPO4) activity in the eye of the mammal. In some embodiments, the second agent increases RSPO1 in the TM of the eye of the mammal. In some embodiments, the second agent is RSPO1 or a functional variant thereof. In some embodiments, the second agent is a recombinant adeno-associated virus (rAAV) particle comprising a vector encoding RSPO1 or a functional variant thereof. In some embodiments, the RSPO1 is a truncated RSPO1. In some embodiments, the second agent increases RSPO2 in the TM of the eye of the mammal. In some embodiments, the second agent is RSPO2 or a functional variant thereof. In some embodiments, the second agent is a recombinant adeno-associated virus (rAAV) particle comprising a vector encoding RSPO2 or a functional variant thereof. In some embodiments, the RSPO2 is a truncated RSPO2. In some embodiments, the second agent increases RSPO3 in the TM of the eye of the mammal. In some embodiments, the second agent is RSPO3 or a functional variant thereof. In some embodiments, the second agent is a recombinant adeno-associated virus (rAAV) particle comprising a vector encoding RSPO3 or a functional variant thereof. In some embodiments, the RSPO3 is a truncated RSPO3. In some embodiments, the second agent increases RSPO4 in the TM of the eye of the mammal. In some embodiments, the second agent is RSPO4 or a functional variant thereof. In some embodiments, the second agent is a recombinant adeno-associated virus (rAAV) particle comprising a vector encoding RSPO4 or a functional variant thereof. In some embodiments, the RSPO4 is a truncated RSPO4.

In some aspects, the invention provides methods for treating myocilin (MYOC) glaucoma in a mammal, comprising administering to the eye of the mammal a recombinant adeno-associated virus (rAAV) particle comprising a vector encoding RSPO1, RSPO2, RSPO3, RSPO4, or a functional variant thereof. In some aspects, the present invention provides methods for treating myocilin (MYOC) glaucoma in a mammal, comprising administering to the eye of the mammal a recombinant adeno-associated virus (rAAV) particle comprising a vector encoding a MYOC RNAi which targets expression of a myocilin (MYOC) in the mammal. In other aspects, the invention provides methods for treating myocilin (MYOC) glaucoma in a mammal, comprising administering to the eye of the mammal an agent that increases Wnt signaling in the eye of the mammal and an agent that reduces or inhibits expression of myocilin in the mammal. In other aspects, the invention provides methods for treating myocilin (MYOC) glaucoma in a mammal, comprising administering to the eye of the mammal a recombinant adeno-associated virus (rAAV) particle comprising a vector encoding RSPO1, RSPO2, RSPO3, RSPO4, or a functional variant thereof, and a rAAV particle comprising a vector encoding a MYOC RNAi which targets expression of a myocilin in the mammal. In yet other aspects, the invention provides methods for treating myocilin (MYOC) glaucoma in a mammal, comprising administering to the eye of the mammal a recombinant adeno-associated virus (rAAV) particle comprising a vector encoding RSPO1, RSPO2, RSPO3, RSPO4, or a functional variant thereof, and encoding a MYOC shRNA which targets expression of a myocilin (MYOC shRNA) in the mammal. In some embodiments, the RNAi is a shRNA targeting MYOC. In some embodiments, the shRNA reduces or inhibits expression of MYOC.

In some aspects, the invention provides methods for enhancing Wnt signaling in trabecular meshwork cells in a mammal having an ocular disorder, comprising administering to the eye of the mammal a recombinant adeno-associated virus (rAAV) particle comprising a vector encoding RSPO1, RSPO2, RSPO3, RSPO4, or a functional variant thereof. In some aspects, the invention provides methods for enhancing Wnt signaling in trabecular meshwork cells in a mammal having an ocular disorder, comprising administering to the eye of the mammal a recombinant adeno-associated virus (rAAV) particle comprising a vector encoding an inhibitory nucleic acid which targets expression of a myocilin (MYOC) in the mammal. In other aspects, the invention provides methods for enhancing Wnt signaling in trabecular meshwork cells in a mammal having an ocular disorder, comprising administering to the eye of the mammal a recombinant adeno-associated virus (rAAV) particle comprising a vector encoding a MYOC RNAi which targets expression of a myocilin (MYOC) in the mammal. In other aspects, the invention provides methods for enhancing Wnt signaling in trabecular meshwork cells in a mammal having an ocular disorder, comprising administering to the eye of the mammal a recombinant adeno-associated virus (rAAV) particle comprising a vector encoding RSPO1, RSPO2, RSPO3, RSPO4, or a functional variant thereof, and a rAAV particle comprising a vector encoding a MYOC RNAi which targets expression of a myocilin in the mammal. In other aspects, the invention provides methods for enhancing Wnt signaling in trabecular meshwork cells in a mammal having an ocular disorder, comprising administering to the eye of the mammal a recombinant adeno-associated virus (rAAV) particle comprising a vector encoding RSPO1, RSPO2, RSPO3, RSPO4, or a functional variant thereof, and encoding a MYOC RNAi which targets expression of a myocilin in the mammal. In some embodiments, the ocular disorder is myocilin (MYOC) glaucoma.

In some embodiments, the mammal is a human. In some embodiments of the invention, the myocilin (MYOC) glaucoma is associated with a mutation in a myocilin. In some embodiments, the myocilin (MYOC) glaucoma is associated with a mutation in a human myocilin. In some embodiments, the myocilin mutation comprises one or more amino acid substitutions selected from of E323K, K398R, Q368X, G364V, P370L, D380A, K423E, Y437H, and I477S. In some embodiments, the myocilin mutation comprises a P370L amino acid substitution. In some embodiments, the myocilin mutation comprises a Y437H amino acid substitution. In some embodiments, the myocilin (MYOC) glaucoma is primary open-angle glaucoma (POAC). In some embodiments, the myocilin (MYOC) glaucoma is the juvenile form of primary open angle glaucoma (JOAC). In some embodiments of the invention, the treatment reduces a symptom of myocilin (MYOC) glaucoma. In some embodiments, the reducing a symptom of myocilin (MYOC) glaucoma is a reducing of intraocular pressure, reducing accumulation of MYOC in the trabecular meshwork, reducing ocular hypertension, or increasing aqueous outflow from the trabecular meshwork.

In some embodiments, the RSPO1 is a human RSPO1. In some embodiments, the RSPO1 has more than about 80%, 85%, 90%, 91%, 92%, 93%, 94%, 95%, 96%, 97%, 98%, or 99% identity to human RSPO1. In some embodiments, the RSPO1 comprises the amino acid sequence of SEQ ID NO:8. In some embodiments, the RSPO1 has more than about 80%, 85%, 90%, 91%, 92%, 93%, 94%, 95%, 96%, 97%, 98%, or 99% identity to SEQ ID NO:8. In some embodiments, the RSPO1 comprises the amino acid sequence of SEQ ID NO:11. In some embodiments, the RSPO1 has more than about 80%, 85%, 90%, 91%, 92%, 93%, 94%, 95%, 96%, 97%, 98%, or 99% identity to SEQ ID NO:11. In some embodiments, the RSPO1 comprises the amino acid sequence of SEQ ID NO:12. In some embodiments, the RSPO1 has more than about 80%, 85%, 90%, 91%, 92%, 93%, 94%, 95%, 96%, 97%, 98%, or 99% identity to SEQ ID NO:12. In some embodiments, the RSPO2 is a human RSPO2. In some embodiments, the RSPO2 has more than about 80%, 85%, 90%, 91%, 92%, 93%, 94%, 95%, 96%, 97%, 98%, or 99% identity to human RSPO2. In some embodiments, the RSPO2 comprises the amino acid sequence of SEQ ID NO:9. In some embodiments, the RSPO2 has more than about 80%, 85%, 90%, 91%, 92%, 93%, 94%, 95%, 96%, 97%, 98%, or 99% identity to SEQ ID NO:9. In some embodiments, the RSPO2 comprises the amino acid sequence of SEQ ID NO:13. In some embodiments, the RSPO2 has more than about 80%, 85%, 90%, 91%, 92%, 93%, 94%, 95%, 96%, 97%, 98%, or 99% identity to SEQ ID NO:13. In some embodiments, the RSPO2 comprises the amino acid sequence of SEQ ID NO:14. In some embodiments, the RSPO2 has more than about 80%, 85%, 90%, 91%, 92%, 93%, 94%, 95%, 96%, 97%, 98%, or 99% identity to SEQ ID NO:14. In some embodiments, the RSPO3 is a human RSPO3. In some embodiments, the RSPO3 has more than about 80%, 85%, 90%, 91%, 92%, 93%, 94%, 95%, 96%, 97%, 98%, or 99% identity to human RSPO3. In some embodiments, the RSPO3 comprises the amino acid sequence of SEQ ID NO:1. In some embodiments, the RSPO3 has more than about 80%, 85%, 90%, 91%, 92%, 93%, 94%, 95%, 96%, 97%, 98%, or 99% identity to SEQ ID NO:1. In some embodiments, the RSPO3 comprises the amino acid sequence of SEQ ID NO:15. In some embodiments, the RSPO3 has more than about 80%, 85%, 90%, 91%, 92%, 93%, 94%, 95%, 96%, 97%, 98%, or 99% identity to SEQ ID NO:15. In some embodiments, the RSPO3 comprises the amino acid sequence of SEQ ID NO:16. In some embodiments, the RSPO3 comprises the amino acid sequence of SEQ ID NO:17. In some embodiments, the RSPO3 has more than about 80%, 85%, 90%, 91%, 92%, 93%, 94%, 95%, 96%, 97%, 98%, or 99% identity to SEQ ID NO:17. In some embodiments, the RSPO4 is a human RSPO4. In some embodiments, the RSPO4 has more than about 80%, 85%, 90%, 91%, 92%, 93%, 94%, 95%, 96%, 97%, 98%, or 99% identity to human RSPO4. In some embodiments, the RSPO4 comprises the amino acid sequence of SEQ ID NO:10. In some embodiments, the RSPO4 has more than about 80%, 85%, 90%, 91%, 92%, 93%, 94%, 95%, 96%, 97%, 98%, or 99% identity to SEQ ID NO:10. In some embodiments, the RSPO4 comprises the amino acid sequence of SEQ ID NO:18. In some embodiments, the RSPO4 has more than about 80%, 85%, 90%, 91%, 92%, 93%, 94%, 95%, 96%, 97%, 98%, or 99% identity to SEQ ID NO:18. In some embodiments, the RSPO4 comprises the amino acid sequence of SEQ ID NO:19. In some embodiments, the RSPO4 has more than about 80%, 85%, 90%, 91%, 92%, 93%, 94%, 95%, 96%, 97%, 98%, or 99% identity to SEQ ID NO:12. In some embodiments, the RSPO1, RSPO2, RSPO3, RSPO4, and/or functional variant thereof is operably linked to a promoter. In some embodiments, the promoter is capable of expressing the RSPO1, RSPO2, RSPO3, RSPO4, and/or functional variant thereof in the eye of the mammal. In some embodiments, the promoter is capable of expressing the RSPO1, RSPO2, RSPO3, RSPO4, and/or functional variant thereof in cells of the trabecular meshwork. In some embodiments, the promoter is a hybrid chicken β-actin (CBA) promoter.

In some embodiments, the MYOC RNAi that targets expression of MYOC of the invention targets human MYOC. In some embodiments, the RNAi is a small inhibitory RNA (siRNA), a micro RNA (miRNA), or a small hairpin RNA (shRNA). In some embodiments, the MYOC RNAi is a MYOC shRNA. In some embodiments, the shRNA targets the amino acid sequence of MYOC set forth in SEQ ID NO:6. In some embodiments, the shRNA comprises the loop sequence of SEQ ID NO:7. In some embodiments, the MYOC RNAi (e.g., shRNA) is operably linked to a promoter. In some embodiments, the promoter is capable of expressing the MYOC RNAi (e.g., shRNA) in the eye of the mammal. In further embodiments, the promoter is capable of expressing the MYOC RNAi (e.g., shRNA) in cells of the trabecular meshwork. In some embodiments, the promoter is a hybrid chicken β-actin (CBA) promoter. In some embodiments, the promoter is a RNA polymerase III promoter. In some embodiments, the expression of MYOC RNAi (e.g., shRNA) reduces or inhibits expression of MYOC in eye of the mammal. In some embodiments, the expression of MYOC RNAi (e.g., shRNA) reduces or inhibits expression of MYOC in the cells of the trabecular meshwork of the mammal. In some embodiments, the MYOC is a wildtype MYOC. In some embodiments, the MYOC is a mutant MYOC. In some embodiments, the MYOC is a wildtype MYOC and a mutant MYOC. In further embodiments, the mutant MYOC comprises amino acid substitutions corresponding to P370L and/or Y437H amino acid substitutions of human MYOC. In some embodiments, the myocilin mutation comprises one or more amino acid substitutions selected from of E323K, K398R, Q368X, G364V, P370L, D380A, K423E, Y437H, and I477S.

In some embodiments of the aspects and embodiments described above, the AAV viral particle comprises an AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, the AAV viral particle comprises an AAV capsid comprising an amino acid substitution at one or more of positions R484, R487, K527, K532, R585 or R588, numbering based on VP1 of AAV2. In further embodiments, a AAV particle comprises capsid proteins of an AAV serotype from Clades A-F. In some embodiments, the rAAV viral particle comprises an AAV serotype 2 capsid. In further embodiments, the AAV serotype 2 capsid comprises AAV2 capsid protein comprising a R471A amino acid substitution, numbering relative to AAV2 VP1. In some embodiments, the vector comprises AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype inverted terminal repeats (ITRs). In some embodiments, the vector comprises AAV serotype 2 ITRs. In some embodiments, the AAV viral particle comprises one or more ITRs and capsid derived from the same AAV serotype. In other embodiments, the AAV viral particle comprises one or more ITRs derived from a different AAV serotype than capsid of the rAAV viral particles. In some embodiments, the rAAV viral particle comprises an AAV2 capsid, and wherein the vector comprises AAV2 ITRs. In further embodiments, the AAV2 capsid comprises AAV2 capsid protein comprising a R471A amino acid substitution, numbering relative to AAV2 VP1.

In some embodiments, at least $1 \times 10^9$ genome copies of the rAAV particles are administered to the mammal. In some embodiments the AAV is administered to the cornea, to the retina and/or to the sclera of the eye of the mammal. In some embodiments, the AAV particle is administered by intravitreal injection and/or intracameral injection. In some embodiments, the rAAV is administered to more than one location of the eye.

In some embodiments, the invention provides methods of treating myocilin (MYOC) glaucoma in a mammal wherein the mammal is a human. In some embodiments, the myocilin (MYOC) glaucoma is primary open-angle glaucoma (POAC). In some embodiments, the myocilin (MYOC) glaucoma is juvenile form of primary open angle glaucoma (JOAC).

In some embodiments of the invention, the rAAV viral particles are in a pharmaceutical composition. In further embodiments, the pharmaceutical composition further comprises a pharmaceutically acceptable carrier.

In some embodiments of the above methods, the agent (e.g., the AAV particle) is used in combination with one or more additional agents that increase the activity of a R-spondin (e.g., RSPO1, RSPO2, RSPO3 and/or RSPO4).

In some aspects, the invention provides recombinant AAV particles comprising an AAV vector, wherein the AAV vector comprises nucleic acid encoding RSPO1, RSPO2, RSPO3, RSPO4, or a functional variant thereof. In other aspects, the invention provides rAAV particles comprising a vector encoding an inhibitory nucleic acid which targets expression of a myocilin (MYOC) in the mammal. In other aspects, the invention provides rAAV particles comprising a vector encoding a MYOC RNAi which targets expression of a myocilin (MYOC) in the mammal. In yet other aspects, the invention provides rAAV particles comprising a vector encoding RSPO1, RSPO2, RSPO3, RSPO4, or a functional variant thereof, and encoding a MYOC RNAi which targets expression of a myocilin in the mammal.

In some embodiments, the AAV vector comprises nucleic acid encoding RSPO1 or a functional variant thereof, and the RSPO1 or functional variant thereof is a human RSPO1. In some embodiments, the AAV vector comprises nucleic acid encoding RSPO1 or a functional variant thereof, and the RSPO1 or functional variant thereof comprises the amino acid sequence of SEQ ID NOs:8, 11, and/or 12. In some embodiments, the AAV vector comprises nucleic acid encoding RSPO1 or a functional variant thereof, and the RSPO1 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:8, 11, and/or 12. In some embodiments, the AAV vector comprises nucleic acid encoding RSPO2 or a functional variant thereof, and the RSPO2 or functional variant thereof is a human RSPO2. In some embodiments, the AAV vector comprises nucleic acid encoding RSPO2 or a functional variant thereof, and the RSPO2 or functional variant thereof comprises the amino acid sequence of SEQ ID NOs:9, 13, and/or 14. In some embodiments, the AAV vector comprises nucleic acid encoding RSPO2 or a functional variant thereof, and the RSPO2 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:9, 13, and/or 14. In some embodiments, the AAV vector comprises nucleic acid encoding RSPO3 or a functional variant thereof, and the RSPO3 or functional variant thereof is a human RSPO3. In some embodiments, the AAV vector comprises nucleic acid encoding RSPO3 or a functional variant thereof, and the RSPO3 or functional variant thereof comprises the amino acid sequence of SEQ ID NOs:1 and/or 15-17. In some embodiments, the AAV vector comprises nucleic acid encoding RSPO3 or a functional variant thereof, and the RSPO3 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:1 and/or 15-17. In some embodiments, the AAV vector comprises nucleic acid encoding RSPO4, and the RSPO4 is a human RSPO4. In some embodiments, the AAV vector comprises nucleic acid encoding RSPO4 or a functional variant thereof, and the RSPO4 or functional variant thereof comprises the amino acid sequence of SEQ ID NOs:10, 18, and/or 19. In some embodiments, the AAV vector comprises nucleic acid encoding RSPO4 or a functional variant thereof, and the RSPO4 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:10, 18, and/or 19. In further embodiments, the RSPO1, RSPO2, RSPO3, RSPO4, or functional variant thereof is operably linked to a promoter. In further embodiments, the promoter is capable of expressing the RSPO1, RSPO2, RSPO3, RSPO4, or functional variant thereof in the eye of the mammal. In some embodiments, the promoter is capable of expressing the RSPO1, RSPO2, RSPO3, RSPO4, or functional variant thereof in cells of the trabecular meshwork. In some embodiments, the promoter is a hybrid chicken β-actin (CBA) promoter.

In some embodiments, the inhibitory nucleic acid that targets expression of a myocilin (MYOC) in the mammal is an RNAi. In some embodiments, the MYOC RNAi (e.g., shRNA) that targets expression of MYOC of the invention targets human MYOC. In some embodiments, the RNAi is a small inhibitory RNA (siRNA), a micro RNA (miRNA), or a small hairpin RNA (shRNA). In some embodiments, the MYOC RNAi is a shRNA. In some embodiments, the RNAi (e.g., shRNA) targets the amino acid sequence of MYOC set forth in SEQ ID NO:6. In some embodiments, the RNAi (e.g., shRNA) comprises the loop sequence of SEQ ID NO:7. In some embodiments, the MYOC RNAi (e.g., shRNA) is operably linked to a promoter. In some embodiments, the promoter is capable of expressing the MYOC RNAi (e.g., shRNA) in the eye of the mammal. In further embodiments, the promoter is capable of expressing the MYOC RNAi (e.g., shRNA) in cells of the trabecular meshwork. In some embodiments, the promoter is a hybrid chicken β-actin (CBA) promoter. In some embodiments, the promoter is a RNA polymerase III promoter. In some embodiments, the expression of MYOC RNAi (e.g., shRNA) reduces or inhibits expression of MYOC in the eye of the mammal. In some embodiments, the expression of MYOC RNAi (e.g., shRNA) reduces or inhibits expression of MYOC in the cells of the trabecular meshwork of the mammal. In some embodiments, the MYOC is a wild-type MYOC. In some embodiments, the MYOC is a mutant MYOC. In some embodiments, the MYOC is a wild-type MYOC and a mutant MYOC. In further embodiments, the mutant MYOC comprises amino acid substitutions corresponding to E323K, K398R, Q368X, G364V, P370L, D380A, K423E, Y437H, and I477S amino acid substitutions of human MYOC. In some embodiments, the mutant MYOC comprises amino acid substitutions corresponding to P370L and/or Y437H amino acid substitutions of human MYOC. In some embodiments, the myocilin mutation is associated with primary open-angle glaucoma (POAC). In some embodiments, the myocilin mutation is associated with the juvenile form of primary open angle glaucoma (JOAC).

In some embodiments of the aspects and embodiments described above, the AAV viral particle comprises an AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, the AAV viral particle comprises an AAV capsid comprising an amino acid substitution at one or more of positions R484, R487, K527, K532, R585 or R588, numbering based on VP1 of AAV2. In further embodiments, a AAV particle comprises capsid proteins of an AAV serotype from Clades A-F. In some embodiments, the rAAV viral particle comprises an AAV serotype 2 capsid. In further embodiments, the AAV serotype 2 capsid comprises AAV2 capsid protein comprising a R471A amino acid substitution, numbering relative to AAV2 VP1. In some embodiments, the vector comprises AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype inverted terminal repeats (ITRs). In some embodiments, the vector comprises AAV serotype 2 ITRs. In some embodiments, the AAV viral particle comprises one or more ITRs and capsid derived from the same AAV serotype. In other embodiments, the AAV viral particle comprises one or more ITRs derived from a different AAV serotype than capsid of the rAAV viral particles. In some embodiments, the rAAV viral particle comprises an AAV2 capsid, and wherein the vector comprises AAV2 ITRs. In further embodiments, the AAV2 capsid comprises AAV2 capsid protein comprising a R471A amino acid substitution, numbering relative to AAV2 VP1.

The invention provides pharmaceutical compositions comprising any of the recombinant AAV particles described herein. The invention also provides pharmaceutical compositions that are suitable for any of the methods described herein. The invention provides uses of a pharmaceutical composition and recombinant AAV particles described herein in the manufacture of a medicament for treating myocilin (MYOC) glaucoma in a mammal. In some embodiments, the mammal is a human. In some embodiments, the myocilin (MYOC) glaucoma is primary open-angle glaucoma (POAC). In some embodiments, the myocilin (MYOC) glaucoma is juvenile form of primary open angle glaucoma (JOAC).

In some aspects, the invention provides kits for treating myocilin (MYOC) glaucoma in a mammal wherein the kit comprises a rAAV viral particle comprising a vector encoding RSPO1, RSPO2, RSPO3, RSPO4, or a functional variant thereof; a rAAV viral particle comprising an AAV vector, wherein the AAV vector comprises nucleic acid encoding an inhibitory nucleic acid (e.g., MYOC RNAi including shRNA) which targets expression of a myocilin (MYOC) in the mammal; and/or a rAAV viral particle comprising an AAV vector, wherein the AAV vector comprises nucleic acid encoding RSPO1, RSPO2, RSPO3, RSPO4, or a functional variant thereof, and encoding a MYOC RNAi (e.g., shRNA) which targets expression of a MYOC in the mammal. In some embodiments, the kit further comprises instructions for use in treating myocilin (MYOC) glaucoma. In some embodiments the kit further comprising buffers and/or pharmaceutically acceptable excipients.

In some embodiments, the kits of the invention comprise nucleic acid encoding a MYOC RNAi (e.g., shRNA) which targets expression of a MYOC in the mammal. In some embodiments, the MYOC RNAi targets expression of a human MYOC. In some embodiments, the MYOC RNAi targets the amino acid sequence of MYOC set forth in SEQ ID NO:6. In some embodiments, the RNAi is a small inhibitory RNA (siRNA), a micro RNA (miRNA), or a small hairpin RNA (shRNA). In some embodiments, the RNAi is a shRNA. In some embodiments, the MYOC shRNA comprises the loop sequence of SEQ ID NO:7. In some embodiments, the kits of the invention comprise an AAV vector, wherein the AAV vector comprises nucleic acid encoding RSPO1, RSPO2, RSPO3, RSPO4, or a functional variant thereof. In some embodiments, the AAV vector comprises nucleic acid encoding RSPO1 or a functional variant thereof, and the RSPO1 or functional variant thereof is a human RSPO1. In some embodiments, the AAV vector comprises nucleic acid encoding RSPO1 or a functional variant thereof, and the RSPO1 or functional variant thereof comprises the amino acid sequence of SEQ ID NOs:8, 11, and/or 12. In some embodiments, the AAV vector comprises nucleic acid encoding RSPO1 or a functional variant thereof, and the RSPO1 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:8, 11, and/or 12. In some embodiments, the AAV vector comprises nucleic acid encoding RSPO2 or a functional variant thereof, and the RSPO2 or functional variant thereof is a human RSPO2. In some embodiments, the AAV vector comprises nucleic acid encoding RSPO2 or a functional variant thereof, and the RSPO2 or functional variant thereof comprises the amino acid sequence of SEQ ID NOs:9, 13, and/or 14. In some embodiments, the AAV vector comprises nucleic acid encoding RSPO2 or a functional variant thereof, and the RSPO2 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:9, 13, and/or 14. In some embodiments, the AAV vector comprises nucleic acid encoding RSPO3 or a functional variant thereof, and the RSPO3 or functional variant thereof is a human RSPO3. In some embodiments, the AAV vector comprises nucleic acid encoding RSPO3 or a functional variant thereof, and the RSPO3 or functional variant thereof comprises the amino acid sequence of SEQ ID NOs:1 and/or 15-17. In some embodiments, the AAV vector comprises nucleic acid encoding RSPO3 or a functional variant thereof, and the RSPO3 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:1 and/or 15-17. In some embodiments, the AAV vector comprises nucleic acid encoding RSPO4 or a functional variant thereof, and the RSPO4 or functional variant thereof is a human RSPO4. In some embodiments, the AAV vector comprises nucleic acid encoding RSPO4 or a functional variant thereof, and the RSPO4 or functional variant thereof comprises the amino acid sequence of SEQ ID NOs:10, 18, and/or 19. In some embodiments, the AAV vector comprises nucleic acid encoding RSPO4 or a functional variant thereof, and the RSPO4 or functional variant thereof comprises an amino acid sequence that has 80%, 85%, 90%, 91%, 92%, 93%, 94%, 95%, 96%, 97%, 98%, or 99% identity to the amino acid sequence of SEQ ID NOs:10, 18, and/or 19. In some embodiments, the RSPO1, RSPO2, RSPO3, RSPO4, or functional variant thereof is operably linked to a promoter. In some embodiments, the promoter is capable of expressing the RSPO1, RSPO2, RSPO3, RSPO4, or functional variant thereof in the eye of the mammal. In some embodiments, the promoter is capable of expressing the RSPO1, RSPO2, RSPO3, RSPO4, or functional variant thereof in cells of the trabecular meshwork. In some embodiments, the promoter is a hybrid chicken β-actin (CBA) promoter. In some embodiments, the MYOC RNAi is operably linked to a promoter. In some embodiments, the promoter is capable of expressing the MYOC RNAi in the eye of the mammal. In some embodiments, the promoter is capable of expressing the MYOC RNAi in cells of the trabecular meshwork. In some embodiments, the promoter is a hybrid chicken β-actin (CBA) promoter. In some embodiments, the promoter is an RNA polymerase III promoter. In some embodiments, the expression of MYOC RNAi reduces or inhibits expression of MYOC in eye of the mammal. In some embodiments, the expression of MYOC RNAi reduces or inhibits expression of MYOC in the cells of the trabecular meshwork of the mammal.

In some embodiments, the AAV particles describe herein may be used in combination with one or more additional agents that increase the activity of a R-spondin (e.g., RSPO1, RSPO2, RSPO3 and/or RSPO4).

In some embodiments, the kits of the invention comprise an AAV viral particle comprising a vector and an AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, the AAV viral particle comprises an AAV capsid comprising an amino acid substitution at one or more of positions R484, R487, K527, K532, R585 or R588, numbering based on VP1 of AAV2. In further embodiments, a AAV particle comprises capsid proteins of an AAV serotype from Clades A-F. In some embodiments, the rAAV viral particle comprises an AAV serotype 2 capsid. In some embodiments, the AAV serotype 2 capsid comprises AAV2 capsid protein comprising a R471A amino acid substitution, numbering relative to AAV2 VP1. In some embodiments, the vector comprises AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype inverted terminal repeats (ITRs). In some embodiments, the vector comprises AAV serotype 2 ITRs. In some embodiments, the AAV viral particle comprises one or more ITRs and capsid derived from the same AAV serotype. In some embodiments, the AAV viral particle comprises one or more ITRs derived from a different AAV serotype than capsid of the rAAV viral particles. In some embodiments, the rAAV viral particle comprises an AAV2 capsid, and the vector comprises AAV2 ITRs. In some embodiments, the AAV2 capsid comprises a AAV2 capsid protein comprising a R471A amino acid substitution, numbering relative to AAV2 VP1.

In some embodiments of the above kits, the AAV particle of the kit is used in combination with one or more additional agents that increase the activity of a R-spondin (e.g., RSPO1, RSPO2, RSPO3 and/or RSPO4). In some embodiments, kits of the invention comprise an AAV particle as described herein and one or more additional agents that increase the activity of a R-spondin (e.g., RSPO1, RSPO2, RSPO3 and/or RSPO4).

The invention provides kits suitable for use in any one of the methods of described herein. The invention provides kits comprising any of the recombinant AAV particles described herein. In some aspects, the kits described herein further comprise instructions for use in treating myocilin (MYOC) glaucoma. In some aspects, the kits described herein further comprise buffers and/or pharmaceutically acceptable excipients.

In some aspects, the invention provides methods of delivering nucleic acid (e.g. a nucleic acid encoding a therapeutic transgene) to the trabecular meshwork of the eye of a mammal, comprising administering an AAV serotype 2 (AAV2) particle comprising a rAAV vector to the eye of the mammal, wherein the rAAV vector comprises the nucleic acid, and wherein the AAV2 particle comprises AAV2 capsid protein comprising a R471A amino acid substitution, numbering based on VP1 of AAV2. In some aspects, the invention provides methods of treating an ocular disorder in a mammal comprising administering a AAV2 particle comprising a rAAV vector to the eye of the mammal, wherein the rAAV vector comprises nucleic acid encoding a therapeutic transgene, and wherein the AAV2 particle comprises AAV2 capsid protein comprising a R471A amino acid substitution, numbering based on VP1 of AAV2. In some embodiments, the rAAV particle is administered intravitreally and/or intracamerally. In some embodiments, the rAAV particle transduces cells of the trabecular meshwork of the eye. In some embodiments, the therapeutic transgene is expressed in the trabecular meshwork of the eye. In some embodiments, the therapeutic transgene encodes a therapeutic polypeptide or a therapeutic nucleic acid. In some embodiments, the ocular disorder is a disorder associated with the trabecular meshwork of the eye. In some embodiments, the ocular disorder is myocilin (MYOC) glaucoma. In some embodiments, the mammal is a human.

In some aspects, the invention provides recombinant AAV2 particle for delivering nucleic acid (e.g., nucleic acid encoding a therapeutic transgene) to the trabecular meshwork of the eye of a mammal, wherein the AAV2 particle comprises a rAAV vector, wherein the rAAV vector comprises the nucleic acid, and wherein the AAV2 particle comprises AAV2 capsid protein comprising a R471A amino acid substitution, numbering based on VP1 of AAV2. In some aspects, the invention provides a recombinant AAV2 particle for treating an ocular disorder in a mammal wherein the AAV2 particle comprises a rAAV vector, wherein the rAAV vector comprises nucleic acid encoding a therapeutic transgene, and wherein the AAV2 particle comprises AAV2 capsid protein comprising a R471A amino acid substitution, numbering based on VP1 of AAV2. In some embodiments, the rAAV particle transduces cells of the trabecular meshwork of the eye. In some embodiments, the therapeutic transgene is expressed in the trabecular meshwork of the eye. In some embodiments, the therapeutic transgene encodes a therapeutic polypeptide or a therapeutic nucleic acid. In some embodiments, the ocular disorder is a disorder associated with the trabecular meshwork of the eye. In some embodiments, the ocular disorder is myocilin (MYOC) glaucoma. In some embodiments, the mammal is a human.

In some aspects, the invention provides uses of a recombinant AAV2 particle for delivering nucleic acid (e.g., a nucleic acid encoding a therapeutic transgene) to the trabecular meshwork of the eye of a mammal, wherein the AAV2 particle comprises a rAAV vector, wherein the rAAV vector comprises the nucleic acid, and wherein the AAV2 particle comprises AAV2 capsid protein comprising a R471A amino acid substitution, numbering based on VP1 of AAV2. In some aspects, the invention provides the use of a recombinant AAV2 particle for treating an ocular disorder in a mammal wherein the AAV2 particle comprises a rAAV vector, wherein the rAAV vector comprises nucleic acid encoding a therapeutic transgene, and wherein the AAV2 particle comprises AAV2 capsid protein comprising a R471A amino acid substitution, numbering based on VP1 of AAV2. In some embodiments, the rAAV particle is administered intravitreally and/or intracamerally. In some embodiments, the rAAV particle transduces cells of the trabecular meshwork of the eye. In some embodiments, the therapeutic transgene is expressed in the trabecular meshwork of the eye. In some embodiments, the therapeutic transgene encodes a therapeutic polypeptide or a therapeutic nucleic acid. In some embodiments, the ocular disorder is a disorder associated with the trabecular meshwork of the eye. In some embodiments, the ocular disorder is myocilin (MYOC) glaucoma. In some embodiments, the mammal is a human.

In some aspects, the invention provides kits delivering nucleic acid (e.g., a nucleic acid encoding a therapeutic transgene) to the trabecular meshwork of the eye of a mammal, comprising a rAAV2 particle comprising a rAAV vector, wherein the rAAV vector comprises the nucleic acid, and wherein the AAV2 particle comprises AAV2 capsid protein comprising a R471A amino acid substitution, numbering based on VP1 of AAV2. In some aspects, the invention provides kits for treating an ocular disorder in a mammal comprising a rAAV2 particle comprising a rAAV vector, wherein the rAAV vector comprises nucleic acid encoding a therapeutic transgene, and wherein the AAV2 particle comprises AAV2 capsid protein comprising a R471A amino acid substitution, numbering based on VP1 of AAV2. In some embodiments, the rAAV particle is administered intravitreally and/or intracamerally. In some embodiments, the rAAV particle transduces cells of the trabecular meshwork of the eye. In some embodiments, the therapeutic transgene is expressed in the trabecular meshwork of the eye. In some embodiments, the therapeutic transgene encodes a therapeutic polypeptide or a therapeutic nucleic acid. In some embodiments, the ocular disorder is a disorder associated with the trabecular meshwork of the eye. In some embodiments, the ocular disorder is myocilin (MYOC) glaucoma. In some embodiments, the mammal is a human.

All references cited herein, including patent applications and publications, are incorporated by reference in their entirety.

BRIEF DESCRIPTION OF THE DRAWINGS

FIG. 13A shows the sequence of full-length human RSPO3 (SEQ ID NO:1) with signal sequence, FU1, FU2, and TSP1 domains labeled.

FIG. 13B shows the sequence of an active human RSPO3 fragment (SEQ ID NO:16) with signal sequence, FU1, and FU2 domains labeled. The fragment used, which lacks the signal peptide, corresponds to amino acids 22-146 of SEQ ID NO:16, and is 15 kDa including the His tag.

FIG. 13C depicts the domain structure of full-length hRSPO3 with signal peptide, FU1, FU2, TSP1, and BR domains labeled. Putative functions for each domain are listed below.

FIG. 13D shows a Western blot of full-length hRSPO3 and the hRSPO3 fragment.

FIG. 16 shows that expression of RSPO family members can induce Wnt signaling upon co-expression with Y437H MYOC even without addition of Wnt3a.

DETAILED DESCRIPTION

Figure 1:
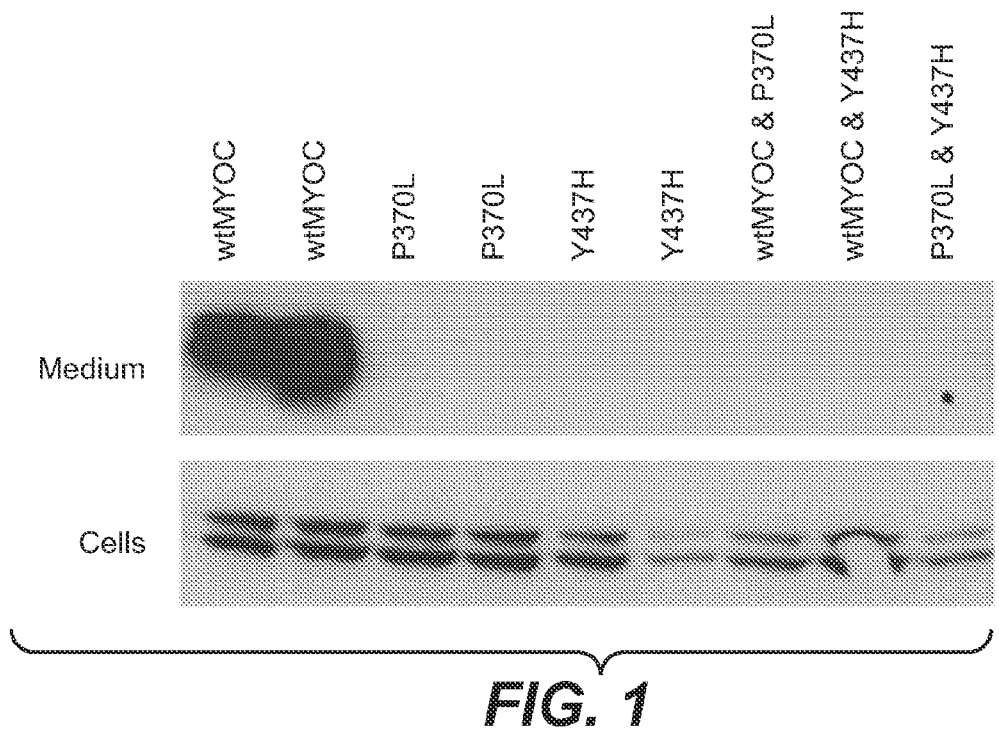
FIG. 1 demonstrates that MYOC mutants P370L and Y437H are not secreted and block the secretion of wild-type MYOC ("wtMYOC"). Cell culture medium or cell lysates from 293 cells transfected with constructs expressing wtMYOC and/or MYOC mutants (as labeled) were probed by Western blotting using anti-human MYOC antibody.

The present invention provides methods for methods for treating myocilin (MYOC) glaucoma in a mammal, comprising administering to the eye of the mammal a recombinant adeno-associated virus (rAAV) viral particle. In some embodiments, wnt signaling in the eye of the mammal is increased; for example, by expression of R-spondin 1 (RSPO1), R-spondin 2 (RSPO2), R-spondin 3 (RSPO3), and/or R-spondin 4 (RSPO4). In some embodiments, expression of myocilin (MYOC) (e.g. mutant myocilin) is inhibited; for example by use of RNAi targeting MYOC expression. In some aspects, the AAV particle comprises a vector encoding RSPO1, RSPO2, RSPO3, and/or RSPO4, and/or a functional variant therein. In other aspects, the rAAV particle comprises a vector encoding a MYOC RNAi (e.g., shRNA) which targets expression of a myocilin (MYOC) in the mammal. In other aspects, the invention provides methods for treating myocilin (MYOC) glaucoma in a mammal comprising administering to the eye of the mammal a mixture of rAAV particles comprising a vector encoding RSPO1, RSPO2, RSPO3, and/or RSPO4, and/or a functional variant therein and rAAV particles comprising a vector encoding a MYOC RNAi (e.g., shRNA) which targets expression of a myocilin in the mammal. In other aspects, the invention provides methods for treating myocilin (MYOC) glaucoma in a mammal, comprising administering to the eye of the mammal a rAAV particle comprising a vector encoding RSPO1, RSPO2, RSPO3, and/or RSPO4, and/or a functional variant therein and encoding a MYOC RNAi (e.g., shRNA) which targets expression of a myocilin (MYOC shRNA) in the mammal. The invention also provides compositions and kits for treating myocilin (MYOC) glaucoma using the rAAV vectors encoding RSPO1, RSPO2, RSPO3, and/or RSPO4, and/or a functional variant therein and/or MYOC RNAi (e.g., shRNA). The invention also provides recombinant AAV particles, compositions and kits.

In some aspects, the invention provides methods of targeting AAV2 to transduce cells of the trabecular meshwork. In some aspects, the invention provides rAAV2 particles comprising a R471A mutation, numbering based on VP1 of AAV2. In some embodiments, the invention provides methods and compositions for treating ocular diseases associated with the trabecular meshwork (e.g. myocilin (MYOC) glaucoma) using AAV2 viral particles comprising mutated capsid protein (e.g., a R471A amino acid substitution).

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups. Alternatively, the backbone of the nucleic acid can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded nucleic acid can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, preferably two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and, in embodiments, encapsidated in a viral particle, particularly an AAV particle. A rAAV vector can be packaged into an AAV virus capsid to generate a "recombinant adeno-associated viral particle (rAAV particle)". AAV helper functions (i.e., functions that allow AAV to be replicated and packaged by a host cell) can be provided in any of a number of forms, including, but not limited to, helper virus or helper virus genes which aid in AAV replication and packaging. Other AAV helper functions are known in the art.

An "rAAV virus" or "rAAV viral particle" refers to a viral particle composed of at least one AAV capsid protein and an encapsidated rAAV vector genome.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a nucleic acid that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease. For example, an effective amount of a rAAV particle expresses a desired amount of heterologous nucleic acid such as a therapeutic polypeptide or therapeutic nucleic acid.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

The term "trabecular meshwork" as used herein refers to a sponge-like tissue located near the cornea and iris that functions to drain the aqueous humor from the eye into the blood. A sponge-like tissue located near the cornea and iris that functions to drain the aqueous humor from the eye into the blood. The trabecular meshwork contains endothelium-lined spaces (the intertrabecular spaces) through which passes the aqueous humour to Schlemm's canal. It is usually divided into two parts: the corneoscleral meshwork which is in contact with the cornea and the sclera and opens into Schlemm's canal and the uveal meshwork which faces the anterior chamber.

The term "central retina" as used herein refers to the outer macula and/or inner macula and/or the fovea. The term "central retina cell types" as used herein refers to cell types of the central retina, such as, for example, RPE and photoreceptor cells.

The term "macula" refers to a region of the central retina in primates that contains a higher relative concentration of photoreceptor cells, specifically rods and cones, compared to the peripheral retina. The term "outer macula" as used herein may also be referred to as the "peripheral macula". The term "inner macula" as used herein may also be referred to as the "central macula".

The term "fovea" refers to a small region in the central retina of primates of approximately equal to or less than 0.5 mm in diameter that contains a higher relative concentration of photoreceptor cells, specifically cones, when compared to the peripheral retina and the macula.

The term "subretinal space" as used herein refers to the location in the retina between the photoreceptor cells and the retinal pigment epithelium cells. The subretinal space may be a potential space, such as prior to any subretinal injection of fluid. The subretinal space may also contain a fluid that is injected into the potential space. In this case, the fluid is "in contact with the subretinal space." Cells that are "in contact with the subretinal space" include the cells that border the subretinal space, such as RPE and photoreceptor cells.

The term "bleb" as used herein refers to a fluid space within the subretinal space of an eye. A bleb of the invention may be created by a single injection of fluid into a single space, by multiple injections of one or more fluids into the same space, or by multiple injections into multiple spaces, which when repositioned create a total fluid space useful for achieving a therapeutic effect over the desired portion of the subretinal space.

"Chicken β-actin (CBA) promoter" refers to a polynucleotide sequence derived from a chicken β-actin gene (e.g., *Gallus gallus* beta actin, represented by GenBank Entrez Gene ID 396526). As used herein, "chicken β-actin promoter" may refer to a promoter containing a cytomegalovirus (CMV) early enhancer element, the promoter and first exon and intron of the chicken β-actin gene, and the splice acceptor of the rabbit beta-globin gene, such as the sequences described in Miyazaki, J., et al. (1989) *Gene* 79(2):269-77. As used herein, the term "CAG promoter" may be used interchangeably. As used herein, the term "CMV early enhancer/chicken beta actin (CAG) promoter" may be used interchangeably.

"Myocilin (MYOC)" refers to a protein (or gene encoding said protein) implicated in cytoskeletal function, cell adhesion, cell signaling, and cell migration, also known as trabecular meshwork inducible glucocorticoid response, GPOA, TIGR, GLC1A, JOAG, and JOAG1. Myocilin is expressed as a secreted protein in many different cell types. In the eye, myocilin is thought to be secreted into the aqueous humor by the trabecular meshwork, a tissue that is critical in the regulation of intraocular pressure (IOP). As described above, mutations in myocilin are thought to account for a subset of primary open-angle glaucoma cases, particularly the juvenile form of the disorder.

As used herein, "myocilin" may refer to a full-length precursor as well as any processed forms of the protein (e.g., a mature protein secreted from a cell). Examples of myocilin proteins may include without limitation human, mouse, dog, and cat myocilin, e.g., NCBI Reference Sequences NP_000252, NP_034995, NP_001041495, and NP_001265779. Examples of myocilin genes may include without limitation human, mouse, dog, and cat myocilin genes, e.g., GenBank Entrez Gene ID 4653 (MYOC, a.k.a. GPOA, JOAG, TIGR, GLC1A, and JOAG1), GenBank Entrez Gene ID 17926 (Myoc, a.k.a. TIGR, GLC1A, and AI957332), GenBank Entrez Gene ID 490344, and GenBank Entrez Gene ID 101087632.

"R-spondin 1 (RSPO1)" refers to a member of the R-spondin family implicated in modulation of Wnt signaling. The term "RSPO1" may refer to an RSPO1 protein or a gene encoding an RSPO1 protein. Members of a superfamily of thrombospondin type 1 repeat (TSR-1)-containing proteins, R-spondins include a signal peptide, a TSR-1 domain, and two furin-like repeats. While the exact mechanism is unclear, R-spondin family polypeptides are thought to activate Wnt signaling. For further description of the connections between R-spondins and Wnt signaling, see, e.g., Kim, K. A. et al. (2006) *Cell Cycle* 5:23-26; Kim, K. A. et al. (2008) *Mol. Biol. Cell.* 19:2588-2596; Jin, Y. R. and Yoon, J. K. (2012) *Int. J. Biochem. Cell Biol.* 44:2278-2287; and de Lau, W. B., et al. (2012) *Genome Biol.* 13(3):242.

As used herein, "RSPO1" may refer to a full-length precursor as well as any processed forms of the protein (e.g., a mature protein secreted from a cell). Examples of RSPO1 proteins may include without limitation human, mouse, dog, and cat RSPO1, e.g., NCBI Reference Sequences NP_001229837, NP_619624, XP_00562890, and XP_003989918. Examples of RSPO1 genes may include without limitation human, mouse, dog, and cat RSPO1 genes, e.g., GenBank Entrez Gene ID 284654 (RSPO1, a.k.a. RSPO and CRISTIN3), GenBank Entrez Gene ID 192199 (Rspo1, a.k.a. Rspondin and R-spondin), GenBank Entrez Gene ID 608179, and GenBank Entrez Gene ID 101091033. In some embodiments, the RSPO1 is a functional variant of an RSPO1. In some embodiments, a functional RSPO1 variant may include one or more amino acid substitutions, insertions, and/or deletions (e.g., truncations) but retain some or all activity with respect to one or more activities of the full-length RSPO1 (e.g., Wnt signaling activity, assays for which are described and/or exemplified herein). In some embodiments, the functional RSPO1 variant is a truncated RSPO1. Examples of truncated RSPO1 polypeptides include without limitation SEQ ID NOs:11 and 12, or processed forms of SEQ ID NOs:11 and 12 that lack the signal peptide.

"R-spondin 2 (RSPO2)" refers to a member of the R-spondin family implicated in modulation of Wnt signaling. The term "RSPO2" may refer to an RSPO2 protein or a gene encoding an RSPO2 protein. Members of a superfamily of thrombospondin type 1 repeat (TSR-1)-containing proteins, R-spondins include a signal peptide, a TSR-1 domain, and two furin-like repeats. While the exact mechanism is unclear, R-spondin family polypeptides are thought to activate Wnt signaling. For further description of the connections between R-spondins and Wnt signaling, see, e.g., Kim, K. A. et al. (2006) *Cell Cycle* 5:23-26; Kim, K. A. et al. (2008) *Mol. Biol. Cell.* 19:2588-2596; Jin, Y. R. and Yoon, J. K. (2012) *Int. J. Biochem. Cell Biol.* 44:2278-2287; and de Lau, W. B., et al. (2012) *Genome Biol.* 13(3):242.

As used herein, "RSPO2" may refer to a full-length precursor as well as any processed forms of the protein (e.g., a mature protein secreted from a cell). Examples of RSPO2 proteins may include without limitation human, mouse, dog, and cat RSPO2, e.g., NCBI Reference Sequences NP_848660, NP_766403, XP_005627927, and XP_004000104. Examples of RSPO2 genes may include without limitation human, mouse, dog, and cat RSPO2 genes, e.g., GenBank Entrez Gene ID 340419 (RSPO2, a.k.a. CRISTIN2), GenBank Entrez Gene ID 239405 (Rspo2, a.k.a. ftls, AA673245, D430027K22 and 2610028F08Rik), GenBank Entrez Gene ID 482004, and GenBank Entrez Gene ID 101087380. In some embodiments, the RSPO2 is a functional variant of an RSPO2. In some embodiments, a functional RSPO2 variant may include one or more amino acid substitutions, insertions, and/or deletions (e.g., truncations) but retain some or all activity with respect to one or more activities of the full-length RSPO2 (e.g., Wnt signaling activity, assays for which are described and/or exemplified herein). In some embodiments, the functional RSPO2 variant is a truncated RSPO2. Examples of truncated RSPO2 polypeptides include without limitation SEQ ID NOs:13 and 14, or processed forms of SEQ ID NOs:13 and 14 that lack the signal peptide.

"R-spondin 3 (RSPO3)" refers to a member of the R-spondin family implicated in modulation of Wnt signaling. The term "RSPO3" may refer to an RSPO3 protein or a gene encoding an RSPO3 protein. Members of a superfamily of thrombospondin type 1 repeat (TSR-1)-containing proteins, R-spondins include a signal peptide, a TSR-1 domain, and two furin-like repeats. While the exact mechanism is unclear, RSPO3 is thought to activate Wnt signaling, and loss of RSPO3 function in mice and *Xenopus* results in Wnt loss-of-function phenotypes (Kazanskaya, O., et al. (2008) *Development* 135:3655-64). For further description of the connections between R-spondins and Wnt signaling, see, e.g., de Lau, W. B., et al. (2012) *Genome Biol.* 13(3): 242.

As used herein, "RSPO3" may refer to a full-length precursor as well as any processed forms of the protein (e.g., a mature protein secreted from a cell). Examples of RSPO3 proteins may include without limitation human, mouse, dog, and cat RSPO3, e.g., NCBI Reference Sequences NP_116173, NP_082627, XP_005615677, and XP_003986583. Examples of RSPO3 genes may include without limitation human, mouse, dog, and cat RSPO3 genes, e.g., GenBank Entrez Gene ID 84870 (RSPO3, a.k.a. PWTSR, THSD2, and CRISTIN1), GenBank Entrez Gene ID 72780 (Rspo3, a.k.a. Thsd2, Cristin1, AW742308, and 2810459H04Rik), GenBank Entrez Gene ID 476287, and GenBank Entrez Gene ID 101085635. In some embodiments, the RSPO3 is a functional variant of an RSPO3. In some embodiments, a functional RSPO3 variant may include one or more amino acid substitutions, insertions, and/or deletions (e.g., truncations) but retain some or all activity with respect to one or more activities of the full-length RSPO3 (e.g., Wnt signaling activity, assays for which are described and/or exemplified herein). In some embodiments, the functional RSPO3 variant is a truncated RSPO3. Examples of truncated RSPO3 polypeptides include without limitation SEQ ID NOs:15-17, or processed forms of SEQ ID NOs:15-17 that lack the signal peptide.

"R-spondin 4 (RSPO4)" refers to a member of the R-spondin family implicated in modulation of Wnt signaling. The term "RSPO4" may refer to an RSPO4 protein or a gene encoding an RSPO4 protein. Members of a superfamily of thrombospondin type 1 repeat (TSR-1)-containing proteins, R-spondins include a signal peptide, a TSR-1 domain, and two furin-like repeats. While the exact mechanism is unclear, R-spondin family polypeptides are thought to activate Wnt signaling. For further description of the connections between R-spondins and Wnt signaling, see, e.g., Kim, K. A. et al. (2006) *Cell Cycle* 5:23-26; Kim, K. A. et al. (2008) *Mol. Biol. Cell.* 19:2588-2596; Jin, Y. R. and Yoon, J. K. (2012) *Int. J. Biochem. Cell Biol.* 44:2278-2287; and de Lau, W. B., et al. (2012) *Genome Biol.* 13(3):242.

As used herein, "RSPO4" may refer to a full-length precursor as well as any processed forms of the protein (e.g., a mature protein secreted from a cell). Examples of RSPO4 proteins may include without limitation human, mouse, dog, and cat RSPO4, e.g., NCBI Reference Sequences NP_001025042, NP_001035779, XP_542937, and XP_011279253. Examples of RSPO4 genes may include without limitation human, mouse, dog, and cat RSPO4 genes, e.g., GenBank Entrez Gene ID 343637 (RSPO4, a.k.a. CRISTIN4 and C20orf182), GenBank Entrez Gene ID 228770 (Rspo4, a.k.a. A730099F22 and A930029K19Rik), GenBank Entrez Gene ID 485813, and GenBank Entrez Gene ID 101091527. In some embodiments, the RSPO4 is a functional variant of an RSPO4. In some embodiments, a functional RSPO4 variant may include one or more amino acid substitutions, insertions, and/or deletions (e.g., truncations) but retain some or all activity with respect to one or more activities of the full-length RSPO4 (e.g., Wnt signaling activity, assays for which are described and/or exemplified herein). In some embodiments, the functional RSPO4 variant is a truncated RSPO4. Examples of truncated RSPO4 polypeptides include without limitation SEQ ID NOs:18 and 19, or processed forms of SEQ ID NOs:18 and 19 that lack the signal peptide.

As used herein "RNA interference (RNAi)" is a biological process in which RNA molecules inhibit gene expression, typically by causing the destruction of specific mRNA molecules. Examples of RNAi include small inhibitory RNA (siRNA), micro RNA (miRNA), small hairpin RNA (shRNA).

As used herein, a "small hairpin RNA" or "short hairpin RNA" (shRNA) is a RNA molecule that makes a tight hairpin turn that can be used to silence target gene expression; for example, by RNA interference.

"Wnt signaling" refers to a group of related cell signaling pathways that are regulated by the interaction between a Wnt protein and a Frizzled (Fz) family receptor (for a review, see, e.g., Logan, C. Y., and Nusse, R. (2004) *Annu. Rev. Cell Dev. Biol.* 20:781-810). These pathways have been implicated in a wide array of developmental and pathogenic processes. As used herein, unless otherwise specified, the term "Wnt signaling" may refer to part or all of the canonical Wnt pathway, the Wnt/planar cell polarity (PCP) pathway, and/or the Wnt/calcium pathway. For example, in the canonical Wnt pathway, binding of Wnt to the Frizzled/LRP receptor complex results in modulation of Dishevelled (Dsh), Axin, Adenomatous Polyposis Coli (APC), and glycogen synthase kinase (GSK-3) activity, ultimately inhibiting the degradation of beta-catenin. Beta-catenin is then able to translocate to the nucleus and regulate gene transcription, e.g., in conjunction with lymphoid enhancer-binding factor 1/T cell-specific transcription factor (LEF/TCF) transcription factors. In some embodiments, beta-catenin activity may be assayed as a readout for Wnt signaling (e.g., by a TOP-Flash assay, such as the one characterized in Molenaar, M., et al. (1996) *Cell* 86(3):391-9).

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. Methods of Treatment

The invention provides methods of gene therapy for myocilin (MYOC) glaucoma wherein rAAV particles comprising therapeutic vectors are delivered to the eye of a mammal. In some embodiments, the myocilin (MYOC) glaucoma primary open-angle glaucoma (POAC). In some embodiments, the myocilin (MYOC) glaucoma is the juvenile form of primary open angle glaucoma (JOAC). In some embodiments, the mammal is a human (e.g., a human with POAC or a human with JOAC). In some embodiments, the mammal with myocilin (MYOC) glaucoma has a mutated MYOC. In some embodiments, the mutated MYOC comprises one or more amino acid substitutions corresponding to E323K, K398R, Q368X, G364V, P370L, D380A, K423E, Y437H, and I477S of human MYOC. In some embodiments the mutated MYOC gene comprises one or more amino acid substitutions corresponding to P370L and/or Y437H amino acid substitutions of human MYOC. In some embodiments, the invention provides methods of treating myocilin (MYOC) glaucoma in a human comprising administering to the eye of the human, an effective amount of rAAV particles comprising a vector encoding RSPO1, RSPO2, RSPO3, RSPO4, or a functional variant thereof and/or MYOC RNAi (e.g., shRNA). In some embodiments, the methods of the invention are used for reducing a symptom of myocilin (MYOC) glaucoma in a mammal; for example, reducing of intraocular pressure, reducing accumulation of MYOC in the trabecular meshwork, reducing ocular hypertension, or increasing aqueous outflow from the trabecular meshwork.

In some aspects, the invention provides methods for enhancing Wnt signaling in trabecular meshwork cells in a mammal having an ocular disorder, comprising administering to the eye of the mammal a recombinant adeno-associated virus (rAAV) particle comprising a vector encoding RSPO1, RSPO2, RSPO3, RSPO4, or a functional variant thereof. In some embodiments, the invention provides methods for enhancing Wnt signaling in trabecular meshwork cells in a mammal having an ocular disorder, comprising administering to the eye of the mammal a recombinant adeno-associated virus (rAAV) particle comprising a vector encoding a MYOC RNAi which targets expression of a myocilin (MYOC) in the mammal. In some embodiments, Wnt signaling is enhanced using one or more viral particles expressing RSPO1, RSPO2, RSPO3, RSPO4, or a functional variant thereof and/or MYOC RNAi; for example, RSPO1, RSPO2, RSPO3, RSPO4, or a functional variant thereof and MYOC RNAi may be expressed from rAAV vectors with different recombinant viral genomes or from the same rAAV viral genome.

Therapeutic Vectors

The invention provides methods of gene therapy for myocilin (MYOC) glaucoma wherein rAAV particles comprising therapeutic vectors are delivered to the eye of a mammal; for example, the therapeutic vector may encode a therapeutic nucleic acid and/or a therapeutic polypeptide. A therapeutic AAV vector which encodes a therapeutic nucleic acid and/or therapeutic polypeptide can be generated using methods known in the art, using standard synthesis and recombinant methods. In some embodiments, the therapeutic polypeptide is a polypeptide that stimulates Wnt signaling. In some embodiments, the therapeutic polypeptide stimulates Wnt signaling in the presence of a mutant MYOC. In some embodiments, the therapeutic polypeptide stimulates Wnt signaling in the presence of a human mutant MYOC. In some embodiments, the therapeutic polypeptide stimulates Wnt signaling in the presence of a human mutant MYOC associated with glaucoma. In some embodiments, the mutant MYOC comprises a P370L and/or a Y437H amino acid substitution. In some embodiments, the mutated MYOC comprises one or more amino acid substitutions corresponding to E323K, K398R, Q368X, G364V, P370L, D380A, K423E, Y437H, and I477S of human MYOC.

In some embodiments, the invention provides rAAV vectors for treating myocilin (MYOC) glaucoma wherein the rAAV vectors encodes an R-spondin (RSPO) polypeptide (e.g., RSPO1, RSPO2, RSPO3, RSPO4, or a functional variant thereof). In some embodiments, the RSPO1 polypeptide is a human RSPO1. In some embodiments, the RSPO1 comprises the amino acid sequence of SEQ ID NO:8, or a functional variant thereof. An example of a RSPO1 functional variant includes an RSPO1 that has one or more amino acid substitutions, additions and/or deletions of the amino acid sequence of SEQ ID NO:8. In some embodiments, the variant RSPO1 comprises one, two, three, four, five, six, seven, eight, nine, ten or more than 10 substitutions, additions and/or deletions of the amino acid sequence of SEQ ID NO:8 while maintaining the ability to stimulate Wnt signaling (e.g., in the presence of a mutant MYOC). In some embodiments, the variant RSPO1 has more than about 80%, 85%, 90%, 91%, 92%, 93%, 94%, 95%, 96%, 97%, 98%, or 99% identity to SEQ ID NO:8. In some embodiments, the RSPO1 is a truncated RSPO1. In some embodiments, the truncated RSPO1 may include one or more furin-like Cys-rich domains (e.g., FU1 and/or FU2) but lack one or more of: a signal peptide, a thrombospondin type 1 domain (e.g., TSR-1 or TSP1), and/or a positively-charged C-terminal domain (e.g., including a bipartite NLS and/or BR domain; for reference, see FIGS. 11-13C). In certain embodiments, the truncated RSPO1 may comprise SEQ ID NOs:11 and/or 12, or processed forms of SEQ ID NOs:11 and/or 12 that lack the signal peptide. In certain embodiments, the truncated RSPO1 has more than about 80%, 85%, 90%, 91%, 92%, 93%, 94%, 95%, 96%, 97%, 98%, or 99% identity to SEQ ID NOs:11 and/or 12. In some embodiments, the RSPO2 polypeptide is a human RSPO2. In some embodiments, the RSPO2 comprises the amino acid sequence of SEQ ID NO:9, or a functional variant thereof. An example of a RSPO2 functional variant includes an RSPO2 that has one or more amino acid substitutions, additions and/or deletions of the amino acid sequence of SEQ ID NO:9. In some embodiments, the variant RSPO2 comprises one, two, three, four, five, six, seven, eight, nine, ten or more than 10 substitutions, additions and/or deletions of the amino acid sequence of SEQ ID NO:9 while maintaining the ability to stimulate Wnt signaling (e.g., in the presence of a mutant MYOC). In some embodiments, the variant RSPO2 has more than about 80%, 85%, 90%, 91%, 92%, 93%, 94%, 95%, 96%, 97%, 98%, or 99% identity to SEQ ID NO:9. In some embodiments, the RSPO2 is a truncated RSPO2. In some embodiments, the truncated RSPO2 may include one or more furin-like Cys-rich domains (e.g., FU1 and/or FU2) but lack one or more of: a signal peptide, a thrombospondin type 1 domain (e.g., TSR-1 or TSP1), and/or a positively-charged C-terminal domain (e.g., including a bipartite NLS and/or BR domain; for reference, see FIGS. 11-13C). In certain embodiments, the truncated RSPO2 may comprise SEQ ID NOs:13 and/or 14, or processed forms of SEQ ID NOs:13 and/or 14 that lack the signal peptide. In certain embodiments, the truncated RSPO2 has more than about 80%, 85%, 90%, 91%, 92%, 93%, 94%, 95%, 96%, 97%, 98%, or 99% identity to SEQ ID NOs:13 and/or 14. In some embodiments, the RSPO3 polypeptide is a human RSPO3. In some embodiments, the RSPO3 comprises the amino acid sequence of SEQ ID NO:1, or a functional variant thereof. An example of a RSPO3 functional variant includes an RSPO3 that has one or more amino acid substitutions, additions and/or deletions of the amino acid sequence of SEQ ID NO:1. In some embodiments, the variant RSPO3 comprises one, two, three, four, five, six, seven, eight, nine, ten or more than 10 substitutions, additions and/or deletions of the amino acid sequence of SEQ ID NO:1 while maintaining the ability to stimulate Wnt signaling (e.g., in the presence of a mutant MYOC). In some embodiments, the variant RSPO3 has more than about 80%, 85%, 90%, 91%, 92%, 93%, 94%, 95%, 96%, 97%, 98%, or 99% identity to SEQ ID NO:1. In some embodiments, the RSPO3 is a truncated RSPO3. In some embodiments, the truncated RSPO3 may include one or more furin-like Cys-rich domains (e.g., FU1 and/or FU2) but lack one or more of: a signal peptide, a thrombospondin type 1 domain (e.g., TSR-1 or TSP1), and/or a positively-charged C-terminal domain (e.g., including a bipartite NLS and/or BR domain; for reference, see FIGS. 11-13C). In certain embodiments, the truncated RSPO3 may comprise SEQ ID NOs:15, 16, and/or 17, or processed forms of SEQ ID NOs:15, 16, and/or 17 that lack the signal peptide. In certain embodiments, the truncated RSPO3 has more than about 80%, 85%, 90%, 91%, 92%, 93%, 94%, 95%, 96%, 97%, 98%, or 99% identity to SEQ ID NOs:15, 16 and/or 17. In some embodiments, the RSPO4 polypeptide is a human RSPO4. In some embodiments, the RSPO4 comprises the amino acid sequence of SEQ ID NO:9, or a functional variant thereof. An example of a RSPO2 functional variant includes an RSPO2 that has one or more amino acid substitutions, additions and/or deletions of the amino acid sequence of SEQ ID NO:10. In some embodiments, the variant RSPO4 comprises one, two, three, four, five, six, seven, eight, nine, ten or more than 10 substitutions, additions and/or deletions of the amino acid sequence of SEQ ID NO:10 while maintaining the ability to stimulate Wnt signaling (e.g., in the presence of a mutant MYOC). In some embodiments, the variant RSPO4 has more than about 80%, 85%, 90%, 91%, 92%, 93%, 94%, 95%, 96%, 97%, 98%, or 99% identity to SEQ ID NO:10. In some embodiments, the RSPO4 is a truncated RSPO4. In some embodiments, the truncated RSPO4 may include one or more furin-like Cys-rich domains (e.g., FU1 and/or FU2) but lack one or more of: a signal peptide, a thrombospondin type 1 domain (e.g., TSR-1 or TSP1), and/or a positively-charged C-terminal domain (e.g., including a bipartite NLS and/or BR domain; for reference, see FIGS. 11-13C). In certain embodiments, the truncated RSPO4 may comprise SEQ ID NOs:18 and/or 19, or processed forms of SEQ ID NOs:18 and 19 that lack the signal peptide. In certain embodiments, the truncated RSPO4 has more than about 80%, 85%, 90%, 91%, 92%, 93%, 94%, 95%, 96%, 97%, 98%, or 99% identity to SEQ ID NOs:18 and/or 19.

In some embodiments, the rAAV vector comprises nucleic acid encoding RSPO1, RSPO2, RSPO3, RSPO4, or a functional variant thereof operably linked to a promoter. In some embodiments, the promoter is capable of expressing the RSPO1, RSPO2, RSPO3, RSPO4, or functional variant thereof in the eye of the mammal. In some embodiments, the promoter is capable of expressing the RSPO1, RSPO2, RSPO3, RSPO4, or functional variant thereof in cells of the trabecular meshwork. In some embodiments, the promoter is a hybrid chicken β-actin (CBA) promoter.

The invention provides methods of gene therapy for myocilin (MYOC) glaucoma wherein rAAV particles comprising therapeutic vectors are delivered to the eye of a mammal; for example, the therapeutic vector may encode a therapeutic nucleic acid and/or a therapeutic polypeptide. A therapeutic AAV vector which encodes a therapeutic nucleic acid and/or therapeutic polypeptide can be generated using methods known in the art, using standard synthesis and recombinant methods. In some embodiments, the therapeutic nucleic acid encodes an RNA that targets expression of MYOC. In some embodiments, the heterologous nucleic acid encodes an RNA that reduces or inhibits expression of MYOC. In some embodiments, the heterologous nucleic acid encodes an RNA that reduces or inhibits expression of a mutant MYOC. In some embodiments, the heterologous nucleic acid encodes an RNA that reduces or inhibits expression of a mutant human MYOC. In some embodiments, the mutant human MYOC comprises a P370L amino acid substitution and/or a Y437 amino acid substitution. Nonlimiting examples of therapeutic nucleic acid include RNAi, small inhibitory RNA (siRNA), micro RNA (miRNA), small hairpin RNA (shRNA) and/or ribozymes (such as hammerhead and hairpin ribozymes). In some embodiments, the heterologous nucleic acid encodes an RNA that reduces or inhibits expression of MYOC is a shRNA that reduces or inhibits expression of MYOC (e.g., wildtype and mutant MYOC).

In some aspects, the invention provides methods of gene therapy for myocilin (MYOC) glaucoma wherein rAAV particles comprising therapeutic vectors are delivered to the eye of a mammal wherein the vectors comprise nucleic acid which encodes one or more therapeutic polypeptides. rAAV particles comprising therapeutic vectors can be generated using methods known in the art, using standard synthesis and recombinant methods. In some embodiments, the vector encodes a therapeutic polypeptide. In some embodiments, the therapeutic polypeptide targets Wnt signaling. In some embodiments, the therapeutic polypeptide stimulates Wnt signaling.

In some aspects, the invention provides methods of gene therapy for myocilin (MYOC) glaucoma wherein rAAV particles comprising therapeutic vectors are delivered to the eye of a mammal wherein the vectors comprise nucleic acid which encodes one or more therapeutic polypeptides and one or more therapeutic nucleic acids. rAAV particles comprising therapeutic vectors can be generated using methods known in the art, using standard synthesis and recombinant methods. In some embodiments, the therapeutic polypeptide targets Wnt signaling and the therapeutic nucleic acid targets MYOC expression. In some embodiments, the therapeutic polypeptide stimulates Wnt signaling. In some embodiments, the heterologous nucleic acid encodes an RNA that reduces or inhibits expression of MYOC. In some embodiments, the heterologous nucleic acid encodes an RNA that reduces or inhibits expression of a mutant MYOC. In some embodiments, the heterologous nucleic acid encodes an RNA that reduces or inhibits expression of a mutant human MYOC. In some embodiments, the mutant human MYOC comprises a P370L amino acid substitution and/or a Y437 amino acid substitution. Nonlimiting examples of therapeutic nucleic acid include RNAi, siRNA, miRNA, shRNA and/or ribozymes.

In some aspects, the invention provides methods of gene therapy for myocilin (MYOC) glaucoma in a mammal wherein rAAV particles comprising vectors encoding one or more therapeutic polypeptides are administered to the mammal and rAAV particles comprise vectors encoding one or more therapeutic nucleic acids are administered to the mammal. In some embodiments, the therapeutic polypeptide targets Wnt signaling and the therapeutic nucleic acid targets MYOC expression. In some embodiments, the therapeutic polypeptide stimulates Wnt signaling. In some embodiments, the heterologous nucleic acid encodes an RNA that reduces or inhibits expression of MYOC. In some embodiments, the heterologous nucleic acid encodes an RNA that reduces or inhibits expression of a mutant MYOC. In some embodiments, the heterologous nucleic acid encodes an RNA that reduces or inhibits expression of a mutant human MYOC. In some embodiments, the mutant human MYOC comprises a P370L amino acid substitution and/or a Y437 amino acid substitution. Nonlimiting examples of therapeutic nucleic acid include RNAi, siRNA, miRNA, shRNA and/or ribozymes. The rAAV particles comprising vectors encoding one or more therapeutic polypeptides and the rAAV particles comprising vectors encoding one or more therapeutic nucleic acids can be administered to the mammal simultaneously or sequentially. In some embodiments, rAAV particles comprising vectors encoding one or more therapeutic polypeptides are administered before rAAV particles comprising vectors encoding one or more therapeutic nucleic acids are be administered. In some embodiments, rAAV particles comprising vectors encoding one or more therapeutic polypeptides are administered after rAAV particles comprising vectors encoding one or more therapeutic nucleic acids are be administered.

The nucleic acids of the invention may encode polypeptides that are intracellular proteins, anchored in the cell membrane, remain within the cell, or are secreted by the cell transduced with the vectors of the invention. For polypeptides secreted by the cell that receives the vector; preferably the polypeptide is soluble (i.e., not attached to the cell). For example, soluble polypeptides are devoid of a transmembrane region and are secreted from the cell. Techniques to identify and remove nucleic acid sequences which encode transmembrane domains are known in the art.

The vectors that can be administered according to the present invention also include vectors comprising a nucleic acid which encodes a RNA (e.g., shRNA, RNAi, ribozymes, miRNA, siRNA, antisense RNA) that when transcribed from the nucleic acids of the vector can treat myocilin (MYOC) glaucoma by interfering with translation or transcription of an abnormal or excess protein associated with a disease state of the invention; for example, MYOC. In some examples, the nucleic acids of the invention may encode for an RNA which treats a disease by highly specific elimination or reduction of mRNA encoding the abnormal and/or excess proteins. Therapeutic RNA sequences include small hairpin RNA (shRNA), RNAi, small inhibitory RNA (siRNA), micro RNA (miRNA), and/or ribozymes (such as hammerhead and hairpin ribozymes) that can treat diseases by highly specific elimination or reduction of mRNA encoding the abnormal and/or excess proteins, such as those occurring in various forms of inherited retinal degeneration. Examples of therapeutic RNA sequences and nucleic acids encoding these sequences which may be used in the invention include those described in, for example, U.S. Pat. No. 6,225,291, the disclosure of which is herein incorporated by reference in its entirety.

In some embodiments of the invention, the therapeutic RNA sequence is a RNAi (e.g., shRNA) sequence targeting expression of MYOC. In some embodiments, the RNAi (e.g., shRNA) sequence targeting expression of MYOC is a RNAi (e.g., shRNA) sequence that reduces or inhibits expression of MYOC. In some embodiments, the RNAi (e.g., shRNA) reduces or inhibits expression of a human MYOC. In some embodiments, the RNAi (e.g., shRNA) reduces or inhibits expression of a MYOC comprising the amino acid sequence of SEQ ID NO:3. In some embodiments, the MYOC RNAi (e.g., shRNA) targets a QAMSVIH (SEQ ID NO:6) amino acid sequence of MYOC. In some embodiments, the rAAV particles encode a vector comprising more than one RNAi (e.g., shRNA) that targets (e.g., reduces or inhibits) expression of MYOC. In some embodiments, the loop sequence of the MYOC RNAi (e.g., shRNA) comprises the nucleic acid sequence AATAGTGAAGCCACAGATGTATT (SEQ ID NO:7). In some embodiments, the rAAV particles encode a vector comprising one, two, three, four, five, or more RNAi (e.g., shRNA) that targets (e.g., reduces or inhibits) expression of MYOC.

In some embodiments, the rAAV vector comprises nucleic acid encoding a MYOC RNAi (e.g., shRNA) operably linked to a promoter. In some embodiments, the promoter is capable of expressing the MYOC RNAi (e.g., shRNA) in the eye of the mammal. In some embodiments, the promoter is capable of expressing the MYOC RNAi (e.g., shRNA) in cells of the trabecular meshwork. In some embodiments, the promoter is a hybrid chicken β-actin (CBA) promoter. In some embodiments, the promoter is a RNA polymerase III promoter.

In some embodiments, the rAAV vector comprises nucleic acid encoding any RSPO1, RSPO2, RSPO3, RSPO4, or functional variant thereof as described herein and nucleic acid encoding any MYOC RNAi (e.g., shRNA) as described herein. In some embodiments, the nucleic acid encoding RSPO1, RSPO2, RSPO3, RSPO4, or a functional variant thereof and the nucleic acid encoding MYOC RNAi (e.g., shRNA) are on different rAAV genomes. In some embodiments, the nucleic acid encoding RSPO1, RSPO2, RSPO3, RSPO4, or a functional variant thereof and the nucleic acid encoding MYOC RNAi (e.g., shRNA) are on the same rAAV genome. In some embodiments, the nucleic acid encoding RSPO1, RSPO2, RSPO3, RSPO4, or a functional variant thereof and the nucleic acid encoding MYOC RNAi (e.g., shRNA) are operably linked to the same promoter. In some embodiments, the nucleic acid encoding RSPO1, RSPO2, RSPO3, RSPO4, or a functional variant thereof and the nucleic acid encoding MYOC RNAi (e.g., shRNA) are operably linked to the different promoters. In some embodiments, the nucleic acid encoding the RSPO1, RSPO2, RSPO3, RSPO4, or functional variant thereof is 5' to the nucleic acid encoding the MYOC RNAi (e.g., shRNA). In some embodiments, the nucleic acid encoding the RSPO1, RSPO2, RSPO3, RSPO4, or functional variant thereof is 3' to the nucleic acid encoding the MYOC RNAi (e.g., shRNA). In some embodiments, the nucleic acid encoding RSPO1, RSPO2, RSPO3, RSPO4, or a functional variant thereof and the nucleic acid encoding MYOC RNAi (e.g., shRNA) are operably linked to the same promoter, wherein the nucleic acid includes an internal ribosome entry site (IRES) between the RSPO1, RSPO2, RSPO3, RSPO4, or functional variant thereof and MYOC RNAi (e.g., shRNA) nucleic acids.

rAAV Compositions

In some aspects, the invention provides compositions comprising any of the rAAV particles described herein. Generally, the compositions for use in the methods and systems of the invention comprise an effective amount of rAAV particles comprising rAAV vectors encoding a polypeptide and/or RNA, preferably in a pharmaceutically acceptable excipient. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

Generally, these compositions are formulated for administration by ocular injection (e.g., intravitreal, intracameral, subretinal). Accordingly, these compositions are preferably combined with pharmaceutically acceptable vehicles such as saline, Ringer's balanced salt solution (pH 7.4), and the like. Although not required, the compositions may optionally be supplied in unit dosage form suitable for administration of a precise amount.

In some embodiments, the invention provides pharmaceutical formulations of rAAV for the treatment of myocilin (MYOC) glaucoma. In some embodiments, the formulation comprises rAAV particles comprising a rAAV vector encoding an RSPO1, RSPO2, RSPO3, and/or RSPO4 polypeptide, or a functional variant thereof. In some embodiments, the formulation comprises rAAV particles comprising a rAAV vector encoding a MYOC RNAi (e.g., shRNA). In some embodiments, the formulation comprises rAAV particles comprising an rAAV vector encoding an RSPO1, RSPO2, RSPO3, and/or RSPO4 polypeptide, or a functional variant thereof, and a MYOC RNAi (e.g., shRNA). In some embodiments, the formulation comprises rAAV particles comprising a rAAV vector encoding an RSPO1, RSPO2, RSPO3, and/or RSPO4 polypeptide, or a functional variant thereof, and rAAV particles comprising a rAAV vector encoding a MYOC RNAi (e.g., shRNA).

Methods of Ocular Delivery of rAAV

In some aspects, the invention provides methods of treating myocilin (MYOC) glaucoma in a mammal comprising administering rAAV particles to the eye of the mammal. In some embodiments, the rAAV particles comprise a rAAV vector encoding an RSPO1, RSPO2, RSPO3, and/or RSPO4 polypeptide, or a functional variant thereof, and/or a rAAV vector encoding a MYOC RNAi (e.g., shRNA). In some embodiments, the rAAV particles are delivered to the eye by intravitreal and/or intracameral injection. Methods of administering rAAV particles to the eye known in the art.

In some embodiments, rAAV particles comprising rAAV vectors encoding RSPO1, RSPO2, RSPO3, RSPO4, or a functional variant thereof and/or MYOC RNAi (e.g., shRNA) are delivered to the eye of a mammal where the RSPO1, RSPO2, RSPO3, RSPO4, or functional variant thereof and/or MYOC RNAi (e.g., shRNA) are expressed in the trabecular meshwork of the eye. In some embodiments, rAAV particles comprising rAAV vectors encoding RSPO1, RSPO2, RSPO3, RSPO4, or a functional variant thereof are delivered to the eye of a mammal where other parts of the eye are transduced (e.g., retinal ganglion cells). Use of rAAV particles comprising AAV2 capsid comprising a R471A amino acid substitution may facilitate transduction of cells of the trabecular meshwork.

By safely and effectively transducing ocular cells (e.g., cells of the trabecular meshwork) with a vector comprising a therapeutic polypeptide or nucleic acid sequence, the methods of the invention may be used to treat an individual; e.g., a human, having a myocilin (MYOC) glaucoma, wherein the transduced cells produce the therapeutic polypeptide or RNA sequence in an amount sufficient to treat the myocilin (MYOC) glaucoma (e.g., POAC or JOAC). In some embodiments, transduction of ocular cells is improved by using rAAV2 particles comprising a R471A amino acid substitution of AAV capsid proteins, numbering based on VP1 of AAV2. In some embodiments, the rAAV particles demonstrate increased transduction of cells of the trabecular meshwork; e.g., transduction of more than about 10%, 25%, 50%, 75%, 100% or any number therebetween of cells of the trabecular meshwork.

An effective amount of rAAV (in some embodiments in the form of particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells (e.g., cells of the trabecular meshwork), in some embodiments at least about 20% of the cells of the desired tissue type, in some embodiments at least about 50%, in some embodiments at least about 80%, in some embodiments at least about 95%, in some embodiments at least about 99% of the cells of the desired tissue type. As a guide, the number of particles administered per injection is generally between about $1 \times 10^6$ and about $1 \times 10^{14}$ particles, between about $1 \times 10^7$ and $1 \times 10^{13}$ particles, between about $1 \times 10^9$ and $1 \times 10^{12}$ particles or about $1 \times 10^9$ particles, about $1 \times 10^{10}$ particles, or about $1 \times 10^{11}$ particles. The rAAV composition may be administered by one or more ocular injections, either during the same procedure or spaced apart by days, weeks, months, or years. In some embodiments, multiple vectors may be used to treat the human.

Methods to identify ocular cells transduced by AAV viral particles are known in the art; for example, immunohistochemistry or the use of a marker such as enhanced green fluorescent protein can be used to detect transduction of viral particles; for example viral particles comprising a rAAV capsid with one or more substitutions of amino acids.

In some embodiments of the invention, the methods comprise intravitreal and/or intracameral administration an effective amount of AAV viral particles to the mammal for treating an individual with myocilin (MYOC) glaucoma; e.g., a human with POAC or JOAC. In some embodiments, the composition is injected to one or more locations in the eye to allow expression of a heterologous nucleic acid in cells of the eye (e.g., cells of the trabecular meshwork). In some embodiments, the composition is injected into any one of one, two, three, four, five, six, seven, eight, nine, ten or more than ten locations in the eye.

In some embodiments the rAAV viral particles comprising a rAAV capsid with are administered to more than one location simultaneously or sequentially. In some embodiments, multiple injections of rAAV viral particles are no more than one hour, two hours, three hours, four hours, five hours, six hours, nine hours, twelve hours or 24 hours apart.

Methods of Subretinal Delivery

Methods of subretinal delivery are known in the art. For example, see WO 2009/105690, incorporated herein by reference. Briefly, the general method for delivering rAAV particles (e.g., rAAV2 particles) to the subretina of the macula and fovea may be illustrated by the following brief outline. This example is merely meant to illustrate certain features of the method, and is in no way meant to be limiting.

Generally, the rAAV vector can be delivered in the form of a composition injected intraocularly (subretinally) under direct observation using an operating microscope. In some embodiments the vector is encapsidated in a rAAV particle wherein the rAAV particle comprises a rAAV capsid comprising rAAV capsid proteins comprising one or more amino acid substitutions at one or more positions that interacts with a heparan sulfate proteoglycan (e.g., reduces or inhibits or ablates HSPG binding), and the rAAV vector comprising a heterologous nucleic acid and at least one AAV inverted terminal repeat. This procedure may involve vitrectomy followed by injection of rAAV vector suspension using a fine cannula through one or more small retinotomies into the subretinal space.

Briefly, an infusion cannula can be sutured in place to maintain a normal globe volume by infusion (of e.g., saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g., saline) creates space to accommodate the intraocular injection of vector, and (3) its controlled removal reduces the possibility of retinal tears and unplanned retinal detachment.

In some embodiments, the rAAV composition is directly injected into the subretinal space outside the central retina, by utilizing a cannula of the appropriate bore size (e.g., 27-45 gauge), thus creating a bleb in the subretinal space. In other embodiments, the subretinal injection of rAAV composition is preceded by subretinal injection of a small volume (e.g., about 0.1 to about 0.5 ml) of an appropriate fluid (such as saline or Ringer's solution) into the subretinal space outside the central retina. This initial injection into the subretinal space establishes an initial fluid bleb within the subretinal space, causing localized retinal detachment at the location of the initial bleb. This initial fluid bleb can facilitate targeted delivery of rAAV composition to the subretinal space (by defining the plane of injection prior to rAAV delivery), and minimize possible rAAV administration into the choroid and the possibility of rAAV injection or reflux into the vitreous cavity. In some embodiments, this initial fluid bleb can be further injected with fluids comprising one or more rAAV compositions and/or one or more additional therapeutic agents by administration of these fluids directly to the initial fluid bleb with either the same or additional fine bore cannulas.

Intraocular administration of the rAAV compositions and/or the initial small volume of fluid can be performed using a fine bore cannula (e.g., 27-45 gauge) attached to a syringe. In some embodiments, the plunger of this syringe may be driven by a mechanized device, such as by depression of a foot pedal. The fine bore cannula is advanced through the sclerotomy, across the vitreous cavity and into the retina at a site pre-determined in each subject according to the area of retina to be targeted (but outside the central retina). Under direct visualization the vector suspension is injected mechanically under the neurosensory retina causing a localized retinal detachment with a self-sealing non-expanding retinotomy. As noted above, the rAAV composition can be either directly injected into the subretinal space creating a bleb outside the central retina or the vector can be injected into an initial bleb outside the central retina, causing it to expand (and expanding the area of retinal detachment). In some embodiments, the injection of rAAV composition is followed by injection of another fluid into the bleb.

Without wishing to be bound by theory, the rate and location of the subretinal injection(s) can result in localized shear forces that can damage the macula, fovea and/or underlying RPE cells. The subretinal injections may be performed at a rate that minimizes or avoids shear forces. In some embodiments, the rAAV composition is injected over about 15-17 minutes. In some embodiments, the vector is injected over about 17-20 minutes. In some embodiments, the rAAV composition is injected over about 20-22 minutes. In some embodiments, the rAAV composition is injected at a rate of about 35 to about 65 µl/min. In some embodiments, the rAAV composition is injected at a rate of about 35 µl/min. In some embodiments, the rAAV composition is injected at a rate of about 40 µl/min. In some embodiments, the rAAV composition is injected at a rate of about 45 µl/min. In some embodiments, the rAAV composition is injected at a rate of about 50 µl/min. In some embodiments, the rAAV composition is injected at a rate of about 55 µl/min. In some embodiments, the rAAV composition is injected at a rate of about 60 µl/min. In some embodiments, the rAAV composition is injected at a rate of about 65 µl/min. One of ordinary skill in the art would recognize that the rate and time of injection of the bleb may be directed by, for example, the volume of the rAAV composition or size of the bleb necessary to create sufficient retinal detachment to access the cells of central retina, the size of the cannula used to deliver the rAAV composition, and the ability to safely maintain the position of the cannula of the invention.

In some embodiments of the invention, the volume of the composition injected to the subretinal space of the retina is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

One or multiple (e.g., 2, 3, or more) blebs can be created. Generally, the total volume of bleb or blebs created by the methods and systems of the invention cannot exceed the fluid volume of the eye, for example about 4 ml in a typical human subject. The total volume of each individual bleb is preferably at least about 0.3 ml, and more preferably at least about 0.5 ml in order to facilitate a retinal detachment of sufficient size to expose the cell types of the central retina and create a bleb of sufficient dependency for optimal manipulation. One of ordinary skill in the art will appreciate that in creating the bleb according to the methods and systems of the invention that the appropriate intraocular pressure must be maintained in order to avoid damage to the ocular structures. The size of each individual bleb may be, for example, about 0.5 to about 1.2 ml, about 0.8 to about 1.2 ml, about 0.9 to about 1.2 ml, about 0.9 to about 1.0 ml, about 1.0 to about 2.0 ml, about 1.0 to about 3.0 ml. Thus, in one example, to inject a total of 3 ml of rAAV composition suspension, 3 blebs of about 1 ml each can be established. The total volume of all blebs in combination may be, for example, about 0.5 to about 3.0 ml, about 0.8 to about 3.0 ml, about 0.9 to about 3.0 ml, about 1.0 to about 3.0 ml, about 0.5 to about 1.5 ml, about 0.5 to about 1.2 ml, about 0.9 to about 3.0 ml, about 0.9 to about 2.0 ml, about 0.9 to about 1.0 ml.

In order to safely and efficiently transduce areas of target retina (e.g., the central retina) outside the edge of the original location of the bleb, the bleb may be manipulated to reposition the bleb to the target area for transduction. Manipulation of the bleb can occur by the dependency of the bleb that is created by the volume of the bleb, repositioning of the eye containing the bleb, repositioning of the head of the human with an eye or eyes containing one or more blebs, and/or by means of a fluid-air exchange. This is particularly relevant to the central retina since this area typically resists detachment by subretinal injection. In some embodiments fluid-air exchange is utilized to reposition the bleb; fluid from the infusion cannula is temporarily replaced by air, e.g., from blowing air onto the surface of the retina. As the volume of the air displaces vitreous cavity fluid from the surface of the retina, the fluid in the vitreous cavity may flow out of a cannula. The temporary lack of pressure from the vitreous cavity fluid causes the bleb to move and gravitate to a dependent part of the eye. By positioning the eye globe appropriately, the bleb of subretinal rAAV composition is manipulated to involve adjacent areas (e.g., the macula and/or fovea). In some cases, the mass of the bleb is sufficient to cause it to gravitate, even without use of the fluid-air exchange. Movement of the bleb to the desired location may further be facilitated by altering the position of the subject's head, so as to allow the bleb to gravitate to the desired location in the eye. Once the desired configuration of the bleb is achieved, fluid is returned to the vitreous cavity. The fluid is an appropriate fluid, e.g., fresh saline. Generally, the subretinal rAAV composition may be left in situ without retinopexy to the retinotomy and without intraocular tamponade, and the retina will spontaneously reattach within about 48 hours.

By safely and effectively transducing ocular cells (e.g., cells of the trabecular meshwork) with a vector comprising a therapeutic polypeptide or RNA sequence, the methods of the invention may be used to treat an individual; e.g., a human, having a myocilin (MYOC) glaucoma, wherein the transduced cells produce the therapeutic polypeptide or RNA sequence in an amount sufficient to treat myocilin (MYOC) glaucoma.

An effective amount of rAAV (in some embodiments in the form of particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. As discussed above, substitution of one or more amino acids of the rAAV capsid that interacts with HSPG improves rAAV transduction. As a guide, the number of particles administered per injection is generally between about $1 \times 10^6$ and about $1 \times 10^{14}$ particles, between about $1 \times 10^7$ and $1 \times 10^{13}$ particles, between about $1 \times 10^9$ and $1 \times 10^{12}$ particles or about $1 \times 10^{11}$ particles. The rAAV composition may be administered by one or more subretinal injections, either during the same procedure or spaced apart by days, weeks, months, or years. In some embodiments, multiple vectors may be used to treat the human.

In some embodiments, the administration to the eye of an effective amount of rAAV viral particles results in more than about any of 5%, 10%, 15%, 20%, 25%, 30%, 35%, 40%, 45%, 50%, 55%, 60%, 65%, 70%, 75% or 100% or any % therebetween of ocular cells are transduced. In some embodiments, about 5% to about 100%, about 10% to about 50%, about 10% to about 30%, about 25% to about 75%, about 25% to about 50%, or about 30% to about 50% of the ocular cells are transduced. Methods to identify ocular cells transduced by AAV viral particles comprising a rAAV capsid are known in the art; for example, immunohistochemistry or the use of a marker such as enhanced green fluorescent protein can be used to detect transduction of viral particles.

In some embodiments, the administration to the trabecular meshwork of an effective amount of rAAV viral particles results in more than about any of 5%, 10%, 15%, 20%, 25%, 30%, 35%, 40%, 45%, 50%, 55%, 60%, 65%, 70%, 75% or 100% or any % therebetween of trabecular meshwork cells are transduced. In some embodiments, about 5% to about 100%, about 10% to about 50%, about 10% to about 30%, about 25% to about 75%, about 25% to about 50%, or about 30% to about 50% of the trabecular meshwork cells are transduced. Methods to identify trabecular meshwork cells transduced by AAV viral particles comprising a rAAV capsid are known in the art; for example, immunohistochemistry or the use of a marker such as enhanced green fluorescent protein can be used to detect transduction of viral particles.

In some embodiments of the invention, the methods comprise administration to the eye of a mammal an effective amount of AAV viral particles for treating an individual with a myocilin (MYOC) glaucoma; e.g., a human with a myocilin (MYOC) glaucoma. In some embodiments, the composition is injected to one or more locations in the eye to allow expression of a heterologous nucleic acid in ocular cells. In some embodiments, the composition is injected into any one of one, two, three, four, five, six, seven, eight, nine, ten or more than ten locations in the eye.

In some embodiments of the invention, the methods comprise administration to the trabecular meshwork of a mammal an effective amount of AAV viral particles for treating an individual with a myocilin (MYOC) glaucoma; e.g., a human with a myocilin (MYOC) glaucoma. In some embodiments, the composition is injected to one or more locations in the trabecular meshwork to allow expression of a heterologous nucleic acid in trabecular meshwork cells. In some embodiments, the composition is injected into any one of one, two, three, four, five, six, seven, eight, nine, ten or more than ten locations in the trabecular meshwork.

In some embodiments the rAAV viral particles are administered to more than one location simultaneously or sequentially. In some embodiments, multiple injections of rAAV viral particles are no more than one hour, two hours, three hours, four hours, five hours, six hours, nine hours, twelve hours or 24 hours apart.

Methods of Intravitreal Injection

The general method for intravitreal injection may be illustrated by the following brief outline. This example is merely meant to illustrate certain features of the method, and is in no way meant to be limiting. Procedures for intravitreal injection are known in the art (see, e.g., Peyman, G. A., et al. (2009) *Retina* 29(7):875-912 and Fagan, X. J. and Al-Qureshi, S. (2013) *Clin. Experiment. Ophthalmol.* 41(5): 500-7).

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as Povidone-Iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site.

During injection, the needle may be inserted perpendicular to the sclera and pointed to the center of the eye. The needle may be inserted such that the tip ends in the vitreous, rather than the subretinal space. Any suitable volume known in the art for injection may be used. After injection, the eye may be treated with a sterilizing agent such as an antibiotic. The eye may also be rinsed to remove excess sterilizing agent.

Methods of Intracameral Injection

Methods of intracameral injection to the eye are known in the art. A non-limiting example of intracameral injection is provided by Buie, et al., (2010) *IOVS* 51(1):236-248.

The effectiveness of rAAV delivery by intravitreal or intracameral injection can be monitored by several criteria as described herein. For example, after treatment in a subject using methods of the present invention, the subject may be assessed for e.g., an improvement and/or stabilization and/or delay in the progression of one or more signs or symptoms of the disease state by one or more clinical parameters including those described herein. Examples of such tests are known in the art, and include objective as well as subjective (e.g., subject reported) measures. For example, to measure the effectiveness of a treatment on a subject's visual function, one or more of the following may be evaluated: the subject's subjective quality of vision or improved central vision function (e.g., an improvement in the subject's ability to read fluently and recognize faces), the subject's visual mobility (e.g., a decrease in time needed to navigate a maze), visual acuity (e.g., an improvement in the subject's Log-MAR score), microperimetry (e.g., an improvement in the subject's dB score), dark-adapted perimetry (e.g., an improvement in the subject's dB score), fine matrix mapping (e.g., an improvement in the subject's dB score), Goldmann perimetry (e.g., a reduced size of scotomatous area (i.e. areas of blindness) and improvement of the ability to resolve smaller targets), flicker sensitivities (e.g., an improvement in Hertz), autofluorescence, and electrophysiology measurements (e.g., improvement in ERG). In some embodiments, the visual function is measured by the subject's visual mobility. In some embodiments, the visual function is measured by the subject's visual acuity. In some embodiments, the visual function is measured by microperimetry. In some embodiments, the visual function is measured by dark-adapted perimetry. In some embodiments, the visual function is measured by ERG. In some embodiments, the visual function is measured by the subject's subjective quality of vision.

For any of the methods or compositions described herein, a medical test for myocilin (MYOC) glaucoma may be used to assess the efficacy of a treatment described herein or diagnose a patient who may benefit from a treatment described herein. Numerous medical tests for diagnosing or monitoring myocilin (MYOC) glaucoma are known in the art. For example, ophthalmoscopy, laser polarimetry, ocular coherence tomography, and/or scanning laser tomography may be used to inspect the optic nerve, which may be damaged by myocilin (MYOC) glaucoma. Intraocular pressure may be measured by tonometry. A pachymeter may be used to measure central corneal thickness (e.g., thin central corneal thickness may be predictive of myocilin (MYOC) glaucoma). A visual field test may be used to assess the visual field.

As described above, myocilin mutations have been implicated in primary open-angle myocilin (MYOC) glaucoma (POAG). Therefore, a medical test for diagnosing POAG may be used to assess the efficacy of a treatment described herein or diagnose a patient who may benefit from a treatment described herein. Any medical test for diagnosing POAG known in the art may be used, e.g., to distinguish POAG from another form of myocilin (MYOC) glaucoma (such as angle-closure glaucoma). For example, gonioscopy may be used to provide an assessment that aids in the diagnosis of POAG.

Efficacy of treatments for myocilin (MYOC) glaucoma may be tested in an animal model. Animal models for myocilin (MYOC) glaucoma are known in the art. For example, mice expressing Y437H human MYOC or Y423H mouse MYOC have been demonstrated to develop myocilin (MYOC) glaucoma symptoms similar to POAG (see Zode et al. (2011) *J. Clin. Invest.* 121(9):3542-53 and Senatorov, V., et al. (2006) *J. Neurosci.* 26(46):11903-14). In addition, mice lacking the alpha subunit of the nitric oxide receptor soluble guanylate cyclase are another model of POAG (Buys, E. S., et al. (2013) *PLoS ONE* 8(3):e60156). Rat models have also been developed; rats expressing human TGF-beta delivered via adenoviral gene transfer show increased IOP (Shepard, A. R., et al. (2010) *Invest. Ophthalmol.* 51(4):2067-76). Further description of other animal models for various aspects of POAG, including primate, dog, and zebrafish models, may be found in Bouhenni, R. A., et al. (2012) *J. Biomed. Biotechnol.* 2012:692609).

In some ocular disorders, there is a "nurse cell" phenomenon, in which improving the function of one type of cell improves the function of another. For example, transduction of the RPE of the central retina by a rAAV of the invention may then improve the function of the rods, and in turn, improved rod function results in improved cone function. Accordingly, treatment of one type of cell may result in improved function in another. In myocilin (MYOC) glaucoma, reduction of IOP by transduction of the TM will reduce the degeneration of the ganglion cell structure & function.

The selection of a particular rAAV vector and composition depend on a number of different factors, including, but not limited to, the individual human's medical history and features of the condition and the individual being treated. The assessment of such features and the design of an appropriate therapeutic regimen is ultimately the responsibility of the prescribing physician.

Compositions of the invention (e.g., AAV viral particles encoding RSPO1, RSPO2, RSPO3, RSPO4, or a functional variant thereof and/or MYOC RNAi (e.g., shRNA)) can be used either alone or in combination with one or more additional therapeutic agents for treating ocular disorders. The interval between sequential administration can be in terms of at least (or, alternatively, less than) minutes, hours, or days.

In some embodiments, one or more additional therapeutic agents may be administered to the trabecular meshwork. Non-limiting examples of the additional therapeutic agent include prostaglandins such as Xalatan, Lumigan, Travatan Z and Rescula; beta-blockers including Timoptic XE, Istalol and Betoptic S; alpha-adrenergic agonists, including Iopidine, Alphagan, and Alphagan-P; carbonic anhydrase inhibitors including Trusopt and Azopt, Diamox, Neptazane and Daranide; parasympathomimetics including pilocarpine, carbachol, echothiophate and demecarium; epinephrines including Propine; or combination treatments including include Cosopt, Combigan and DuoTray.

IV. Expression Constructs

The invention provides methods of delivery of heterologous nucleic acid to the eye by subretinal delivery of a rAAV vector comprising the heterologous nucleic acid and wherein the rAAV vector is encapsidated in a rAAV capsid comprising one or more substitutions of amino acids that interact with HSPG. In some embodiments, the heterologous nucleic acid (e.g., a transgene) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene,* 1991, 108(2):193-9) and the elongation factor 1-alpha promoter (EF1-alpha) promoter (Kim et al., *Gene,* 1990, 91(2):217-23 and Guo et al., *Gene Ther.,* 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the promoter is capable of expressing the heterologous nucleic acid in a cell of the eye. In some embodiments, the promoter is capable of expressing the heterologous nucleic acid in photoreceptor cells or RPE. In embodiments, the promoter is a rhodopsin kinase (RK) promoter; e.g., a human RK promoter. In some embodiments, the promoter is an opsin promoter; e.g., a human opsin promoter or a mouse opsin promoter. In some embodiments, the promoter is a RNA polymerase III promoter. In some embodiments, the invention provides methods of treating myocilin (MYOC) glaucoma in a mammal (e.g., a human) by administering to the eye of the mammal, a rAAV particle comprising a rAAV vector encoding an RSPO1, RSPO2, RSPO3, RSPO4 polypeptide, or a functional variant thereof, under the control of a CBA promoter. In some embodiments, the invention provides methods of treating myocilin (MYOC) glaucoma in a mammal (e.g., a human) by administering to the eye of the mammal, a rAAV particle comprising a rAAV vector encoding a RNAi (e.g., shRNA) that targets (e.g., reduces or inhibits) a MYOC (e.g., a human MYOC) under the control of a CBA promoter. In some embodiments, the invention provides methods of treating myocilin (MYOC) glaucoma in a mammal (e.g., a human) by administering to the eye of the mammal, a rAAV particle comprising a rAAV vector encoding an RSPO1, RSPO2, RSPO3, RSPO4 polypeptide, or a functional variant thereof, under the control of a CBA promoter and a rAAV particle comprising a rAAV vector encoding a RNAi (e.g., shRNA) that targets (e.g., reduces or inhibits) a MYOC (e.g., a human MYOC) under the control of a CBA promoter. In some embodiments, the invention provides methods of treating myocilin (MYOC) glaucoma in a mammal (e.g., a human) by administering to the eye of the mammal, a rAAV particle comprising a rAAV vector encoding an RSPO1, RSPO2, RSPO3, RSPO4 polypeptide, or a functional variant thereof, under the control of a CBA promoter and a RNAi (e.g., shRNA) that targets (e.g., reduces or inhibits) a MYOC (e.g., a human MYOC) under the control of a CBA promoter.

The present invention contemplates the use of a recombinant viral genome for introduction of one or more nucleic acid sequences encoding a therapeutic polypeptide and/or nucleic acid for packaging into a rAAV viral particle. The recombinant viral genome may include any element to establish the expression of the therapeutic polypeptide and/or nucleic acid, for example, a promoter, an ITR, a ribosome binding element, terminator, enhancer, selection marker, intron, polyA signal, and/or origin of replication.

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the first heterologous nucleic acid sequence and a second heterologous nucleic acid sequence are linked by a mutated ITR (e.g., the right ITR). In some embodiments, the ITR comprises the polynucleotide sequence 5'-CACTCCCTCTCT-GCGCGCTCGCTCGCTCACTGAGGCCGGGCGAC-CAAAGGTCGCCCA CGCCCGGGCTTTGCCCGGGCG-3' (SEQ ID NO:20). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

VI. Viral Particles and Methods of Producing Viral Particles rAAV Viral Particles

The invention provides methods of using rAAV particles to treat myocilin (MYOC) glaucoma and provides compositions comprising rAAV particles. In some embodiments, the viral particle is a recombinant AAV particle comprising a nucleic acid comprising a sequence encoding an RSPO1, RSPO2, RSPO3, RSPO4 polypeptide, or a functional variant thereof, and/or a MYOC RNAi (e.g., shRNA) described herein flanked by one or two ITRs. The nucleic acid is encapsidated in the AAV particle. The AAV particle also comprises capsid proteins. In some embodiments, the nucleic acid comprises the coding sequence(s) of interest (e.g., nucleic acid encoding an RSPO1, RSPO2, RSPO3, RSPO4 polypeptide, or a functional variant thereof, and/or a MYOC RNAi (e.g., shRNA)) operatively linked components in the direction of transcription, control sequences including transcription initiation and termination sequences, thereby forming an expression cassette. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS,* 2000, 97(7)3428-32; Passini et al., *J. Virol.,* 2003, 77(12):7034-40; and Pechan et al., *Gene Ther.,* 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.,* 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10): 6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype inverted terminal repeats (ITRs) or the like. In some embodiments, the nucleic acid in the AAV further encodes an RSPO1, RSPO2, RSPO3, RSPO4 polypeptide, or a functional variant thereof; MYOC RNAi (e.g., shRNA); or an RSPO1, RSPO2, RSPO3, RSPO4 polypeptide, or a functional variant thereof, and MYOC as described herein. For example, the nucleic acid in the AAV can comprise at least one ITR of any AAV serotype contemplated herein and can further encode a nucleic acid encoding a MYOC RNAi (e.g., shRNA) targeting SEQ ID NO:6 and comprising the loop sequence of SEQ ID NO:7 and/or one or more of: an RSPO1 comprising SEQ ID NOs:8, 11, and/or 12; an RSPO2 comprising SEQ ID NOs:9, 13, and/or 14; an RSPO3 comprising SEQ ID NOs:1, 15, 16, and/or 17; and an RSPO4 comprising SEQ ID NOs:10, 18, and/or 19. In some embodiments, the nucleic acid encodes an RSPO1 that is at least about 80%, 85%, 90%, 91%, 92%, 93%, 94%, 95%, 96%, 97%, 98%, or 99% identical to SEQ ID NOs:8, 11, or 12; an RSPO2 that is at least about 80%, 85%, 90%, 91%, 92%, 93%, 94%, 95%, 96%, 97%, 98%, or 99% identical to SEQ ID NOs:9, 13, or 14; an RSPO3 that is at least about 80%, 85%, 90%, 91%, 92%, 93%, 94%, 95%, 96%, 97%, 98%, or 99% identical to SEQ ID NOs:1 or 15-17; or an RSPO4 that is at least about 80%, 85%, 90%, 91%, 92%, 93%, 94%, 95%, 96%, 97%, 98%, or 99% identical to SEQ ID NOs:10, 18, or 19.

In further embodiments, the rAAV particle comprises capsid proteins of AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, the AAV viral particle comprises an AAV capsid comprising an amino acid substitution at one or more of positions R484, R487, K527, K532, R585 or R588, numbering based on VP1 of AAV2. In further embodiments, a rAAV particle comprises capsid proteins of an AAV serotype from Clades A-F. In some embodiments, a mutant capsid protein maintains the ability to form an AAV capsid. In some embodiments, the rAAV particles comprise a capsid protein that allows transduction of the trabecular meshwork. In some embodiments, the rAAV particles comprise a mutant capsid protein that allows transduction of the trabecular meshwork. In some embodiments, the rAAV particle comprises capsid proteins of AAV2, wherein the capsid protein comprises a R471A amino acid substitution, numbering based on VP1 of AAV2 (Lochrie et al., *J Virol* (2006) 80(2):821-834). In some embodiments, the invention provides rAAV particles comprising a vector encoding an RSPO1, RSPO2, RSPO3, RSPO4 polypeptide, or a functional variant thereof; an AAV2 capsid comprising an R471A amino acid substitution, numbering based on VP1 of AAV2; and/or a vector encoding MYOC RNAi (e.g., shRNA).

In some embodiments, the invention provides compositions and methods to treat myocilin (MYOC) glaucoma in a mammal, wherein a rAAV2 viral particle comprising a rAAV vector encoding an RSPO1, RSPO2, RSPO3, RSPO4 polypeptide, or a functional variant thereof is delivered to the eye of the mammal where different parts of the eye may be transduced (e.g. the retina) and a rAAV2 R471A viral particle comprising a rAAV vector encoding a MYOC RNAi is delivered to the eye of the mammal where cells of the trabecular meshwork are transduced. In some embodiments, the invention provides compositions and methods to treat myocilin (MYOC) glaucoma in a mammal, wherein a rAAV2 R471A viral particle comprising a rAAV vector encoding an RSPO1, RSPO2, RSPO3, RSPO4 polypeptide, or a functional variant thereof and a rAAV2 R471A viral particle comprising a rAAV vector encoding a MYOC RNAi are delivered to the eye of the mammal where cells of the trabecular meshwork are transduced. In some embodiments, the invention provides compositions and methods to treat myocilin (MYOC) glaucoma in a mammal, wherein a rAAV2 R471A viral particle comprising a rAAV vector encoding an RSPO1, RSPO2, RSPO3, RSPO4 polypeptide, or a functional variant thereof and encoding a MYOC RNAi are delivered to the eye of the mammal where cells of the trabecular meshwork are transduced.

In some aspects, the invention provides compositions and methods to deliver a transgene (e.g., a therapeutic transgene to the trabecular meshwork of the eye). In some embodiments, the compositions and methods use a rAAV2 particle comprising a mutant capsid where the capsid comprises a R471A amino acid substitution, numbering relative to VP1 of AAV2. Such compositions and methods may be used in the treatment of ocular disease; for example, ocular disease associated with the trabecular meshwork such as myocilin (MYOC) glaucoma.

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype.

Self-Complementary AAV Viral Genomes

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., miR-708 and/or a rhodopsin coding strand) and a second heterologous polynucleotide sequence (e.g., antisense strand of miR-708 and/or a rhodopsin noncoding or antisense strand) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). In some embodiments, the ITR comprises the polynucleotide sequence 5'-CACTCCCTCTCT-GCGCGCTCGCTCGCTCACTGAGGCCGGGCGAC-CAAAGGTCGCCC ACGCCCGGGCTTTGCCCGGGCG-3' (SEQ ID NO:20). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding an RSPO1, RSPO2, RSPO3, RSPO4 polypeptide, or a functional variant thereof, and/or a MYOC RNAi (e.g., shRNA), a mutated AAV2 ITR comprising a deletion of the D region and lacking a functional terminal resolution sequence, a second polynucleotide sequence comprising the complementary sequence to the sequence encoding an RSPO1, RSPO2, RSPO3, RSPO4 polypeptide, or a functional variant thereof, and/or a MYOC RNAi (e.g., shRNA), of the first polynucleotide sequence and a functional AAV2 ITR.

Production of AAV Particles

The rAAV particles can be produced using methods know in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) a rAAV pro-vector comprising a nucleic acid encoding a therapeutic polypeptide and/or nucleic acid as described herein flanked by at least one AAV ITR, and (iii) an AAV helper function; and (b) recovering the rAAV particles produced by the host cell.

In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Also provided herein are pharmaceutical compositions comprising a rAAV particle comprising a heterologous nucleic acid encoding a therapeutic polypeptide and/or therapeutic nucleic acid, wherein the rAAV particle comprises a rAAV capsid comprising one or more substitutions or amino acids that interact with HSPG, and a pharmaceutically acceptable carrier. The pharmaceutical compositions may be suitable for any mode of administration described herein; for example, by subretinal administration.

In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Systems & Kits

The rAAV compositions as described herein may be contained within a system designed for use in one of the methods of the invention as described herein. In some embodiments, the invention provides a system for delivery of a vector to an eye of an individual, comprising a) a composition comprising an effective amount of rAAV particles, wherein the vector comprises a heterologous nucleic acid encoding a therapeutic polypeptide and/or therapeutic RNA and at least one AAV terminal repeat; and b) a device for ocular delivery of the rAAV. In some embodiments, the rAAV particles comprise a rAAV vector encoding an RSPO1, RSPO2, RSPO3, RSPO4 polypeptide, or a functional variant thereof. In some embodiments, the rAAV particles comprise an rAAV vector encoding one or more MYOC RNAi(s) (e.g., shRNAs) that target (e.g., reduces or inhibits) MYOC expression. In some embodiments, the rAAV particles comprise a rAAV vector encoding an RSPO1, RSPO2, RSPO3, RSPO4 polypeptide, or a functional variant thereof and one or more MYOC RNAi(s) (e.g., shRNA)s that target (e.g., reduces or inhibits) MYOC expression. In some embodiments, the kit or system comprises rAAV particles comprising a rAAV vector encoding an RSPO1, RSPO2, RSPO3, RSPO4 polypeptide, or a functional variant thereof and rAAV particles comprising a rAAV vector encoding one or more MYOC RNAi(s) (e.g., shRNA) that target (e.g., reduces or inhibits) MYOC expression.

Generally, the system comprises a fine-bore cannula, wherein the cannula is 27 to 45 gauge, one or more syringes (e.g., 1, 2, 3, 4 or more), and one or more fluids (e.g., 1, 2, 3, 4 or more) suitable for use in the methods of the invention.

The fine bore cannula is suitable for subretinal injection of the vector suspension and/or other fluids to be injected into the subretinal space. In some embodiments, the cannula is 27 to 45 gauge. In some embodiments, the fine-bore cannula is 35-41 gauge. In some embodiments, the fine-bore cannula is 40 or 41 gauge. In some embodiments, the fine-bore cannula is 41-gauge. The cannula may be any suitable type of cannula, for example, a de-Juan® cannula or an Eagle® cannula.

The syringe may be any suitable syringe, provided it is capable of being connected to the cannula for delivery of a fluid. In some embodiments, the syringe is an Accurus® system syringe. In some embodiments, the system has one syringe. In some embodiments, the system has two syringes. In some embodiments, the system has three syringes. In some embodiments, the system has four or more syringes.

The system may further comprise an automated injection pump, which may be activated by, e.g., a foot pedal.

The fluids suitable for use in the methods of the invention include those described herein, for example, one or more fluids each comprising an effective amount of one or more vectors as described herein, one or more fluids for creating an initial bleb (e.g., saline or other appropriate fluid), and one or more fluids comprising one or more therapeutic agents.

The fluids suitable for use in the methods of the invention include those described herein, for example, one or more fluids each comprising an effective amount of one or more vectors as described herein, one or more fluids for creating an initial bleb (e.g., saline or other appropriate fluid), and one or more fluids comprising one or more therapeutic agents.

In some embodiments, the volume of the fluid comprising an effective amount of the vector is greater than about 0.8 ml. In some embodiments, the volume of the fluid comprising an effective amount of the vector is at least about 0.9 ml. In some embodiments, the volume of the fluid comprising an effective amount of the vector is at least about 1.0 ml. In some embodiments, the volume of the fluid comprising an effective amount of the vector is at least about 1.5 ml. In some embodiments, the volume of the fluid comprising an effective amount of the vector is at least about 2.0 ml. In some embodiments, the volume of the fluid comprising an effective amount of the vector is greater than about 0.8 to about 3.0 ml. In some embodiments, the volume of the fluid comprising an effective amount of the vector is greater than about 0.8 to about 2.5 ml. In some embodiments, the volume of the fluid comprising an effective amount of the vector is greater than about 0.8 to about 2.0 ml. In some embodiments, the volume of the fluid comprising an effective amount of the vector is greater than about 0.8 to about 1.5 ml. In some embodiments, the volume of the fluid comprising an effective amount of the vector is greater than about 0.8 to about 1.0 ml. In some embodiments, the volume of the fluid comprising an effective amount of the vector is about 0.9 to about 3.0 ml. In some embodiments, the volume of the fluid comprising an effective amount of the vector is about 0.9 to about 2.5 ml. In some embodiments, the volume of the fluid comprising an effective amount of the vector is about 0.9 to about 2.0 ml. In some embodiments, the volume of the fluid comprising an effective amount of the vector is about 0.9 to about 1.5 ml. In some embodiments, the volume of the fluid comprising an effective amount of the vector is about 0.9 to about 1.0 ml. In some embodiments, the volume of the fluid comprising an effective amount of the vector is about 1.0 to about 3.0 ml. In some embodiments, the volume of the fluid comprising an effective amount of the vector is about 1.0 to about 2.0 ml.

The fluid for creating the initial bleb may be, for example, about 0.1 to about 0.5 ml. In some embodiments, the total volume of all fluids in the system is about 0.5 to about 3.0 ml.

In some embodiments, the system comprises a single fluid (e.g., a fluid comprising an effective amount of the vector). In some embodiments, the system comprises 2 fluids. In some embodiments, the system comprises 3 fluids. In some embodiments, the system comprises 4 or more fluids.

The systems of the invention may further be packaged into kits, wherein the kits may further comprise instructions for use. In some embodiments, the kits further comprise a device for subretinal delivery of compositions of rAAV particles. In some embodiments, the instructions for use include instructions according to one of the methods described herein. In some embodiments, the instructions for use include instructions for intravitreal and/or intracameral delivery of rAAV particles comprising a vector encoding an RSPO1, RSPO2, RSPO3, RSPO4 polypeptide, or a functional variant thereof and/or MYOC RNAi (e.g., shRNA).

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Glaucomatous MYOC Mutations (e.g., P370L and Y437H) Block Secretion of MYOC To understand how MYOC mutants affect the function of the eye, particularly cells such as the trabecular meshwork cells that may contribute to IOP, will provide insights into the pathogenesis of myocilin (MYOC) glaucoma. Understanding MYOC function may also help uncover potential therapeutic strategies for myocilin (MYOC) glaucoma. The results described herein demonstrate that MYOC mutants reduce wild-type MYOC expression and block Wnt signaling. Further, these results suggest that expression of R-spondin 3 (RSPO3) and/or silencing of MYOC may restore Wnt signaling blocked by expression of mutant MYOC.

Methods

Plasmid Vectors

For MYOC and RSPO3 plasmids, MYOC cDNA was provided by Clone DB—Sanofi Oncology. RSPO3 cDNA was provided by Clone DB—Sanofi Oncology.

For construction of pCBA2-in-MYOC P370L, QUIKCHANGE® II kit (Agilent, Santa Clara) was used to introduce desired single base substitution following manufacturer's recommendations and primers 5'-ACCACG-GACAGTTCCTGTATTCTTGGGGTGG-3' (SEQ ID NO:21) and 5'-CCACCCCAAGAATAC AGGAACTGTCCGTGGT-3' (SEQ ID NO:22).

For construction of pCBA2-in-MYOC Y437H, QUIKCHANGE® Lightning kit (Agilent, Santa Clara) was used to introduce the desired single base substitution following manufacturer's recommendations and primers 5'-TCTGTGGCACCTTGCACACCGTCAGCAGC-3' (SEQ ID NO:23) and 5'-GCTGCTGACGGTGT GCAAGGTGCCACAGA-3' (SEQ ID NO:24).

Grp94 shRNA plasmids were obtained from OriGene Technologies, Inc. (Cat. No. TR312309). pGIPZ-MYOC plasmids (Dharmacon GE Life Sciences) were provided by Clone DB—Sanofi Oncology. The GIPZ microRNA-adapted shRNA collection (Stegmeier, et al. (2005) *Proc. Natl. Acad. Sci.* USA. 102:13212-7). GIPZ shRNA designs are based on native miR-30 primary transcript to enable processing by the endogenous RNAi pathway and result in specific gene silencing with minimized cellular toxicity. pGIPZ-Null plasmid, a constitutive shRNAmir vector that expresses non-targeting, null shRNAmir, was provided by Clone DB—Sanofi Oncology.

Cell Culture and Recombinant Proteins

HEK293 cells (Microbix Biosystems Inc.) were cultured in DMEM, 10% FCS, and 5% CO2. HEK293T (293T) cell line was obtained from ATCC and cultured in DMEM, 10% FCS, and 5% CO2.

Immortalization of Primary Human Trabecular Meshwork (hTM) Cells

The SV40 Large T-antigen (SV40 TAg) was used for immortalization via transduction with an AAV2-SV40 T-antigen vector. Passage 7 hTM cells (ScienCell Research Laboratories, Carlsbad, Calif.) maintained in complete fibroblast growth media (ScienCell) were seeded onto 10 cm cell culture plates and transduced with $1 \times 10^5$ DRP of either AAV2-SV40-Tag (labeled "hTM-T") or AAV2-EGFP (negative control, labeled "hTM-ENT") for 24 hour. Once the cells reached confluence, they were passaged onto 2×15 cm plates (P8). Cells were repeatedly passaged approximately every 3-4 days. At passage 10, an aliquot was taken to determine a cell count. Total cell number from hTM-T cells was $5.2 \times 10^6$, compared to $2.5 \times 10^5$ total cells from the hTM-ENT cells.

Western blotting was performed to determine the presence of SV40 T-antigen. Briefly, a 500 uL suspension of cells was centrifuged, and the resulting cell pellet lysed into 100 µL RIPA buffer containing a protease inhibitor cocktail. 5 µL of cell lysates were analyzed by SDS-PAGE followed by immunoblotting using the iBlot rapid transfer system (Life Technologies). The blot was blocked using TBS protein free blocker (Thermo Fisher Scientific, Waltham, Mass.) and incubated with a monoclonal anti-SV40 T-antigen antibody (GeneTex, Irvine, Calif.). The blot was then incubated with an anti-mouse HRP labeled antibody (R&D Systems, Minneapolis, Minn.). Immunoreactive bands were visualized using the Supersignal West Femto Chemiluminescent Substrate (Thermo Fisher). A prominent 80 kDa band corresponding to the SV40 T-antigen was detected from hTM-T, but not hTM-ENT cells, indicating the presence and expression of SV40 T-antigen. Lysate from 293T cells served as a positive control which also contained the 80 kDa SV40 T-antigen band. hTM-T cells were expanded and cell banks were frozen in cell freezing media (Life Technologies, Grand Island, N.Y.) at passage 12 (10 vials at $1 \times 10^6$ cells) and later at passage 18 (46 vials at $10^6$ cells).

hTM-T Characterization

Comparison of hTM-T and primary hTM cells showed a marked difference in the cell morphology, population doubling times, and plasmid transfection efficiency. Primary hTM cells appeared larger and fibroblast-like with a long, spindle cell body, whereas the immortalized hTM-T cells were smaller, cuboidal shaped, and a relatively uniform size. The hTM-T cell line demonstrated an increased growth rate with population doublings occurring approximately 3-4 times faster than the primary cells. In addition, hTM-T cells continued to proliferate beyond 20 cell passages, whereas the primary hTM cells displayed decreased growth rate by passage 10 and eventual growth arrest by passage 12. Transfection efficiency was determined using an EGFP plasmid and lipofectamine onto both cell types of similar cell density. Briefly, subconfluent hTM-T or hTM cells were transfected with an EGFP plasmid using Lipofectamine 2000 (Life Technologies) according to the manufacturer's protocol. Although hTM-T cells had greater cell number per $mm^2$ of cell culture surface, there was clearly a greater percentage of EGFP+hTM-T cells (~50%) compared to primary hTM cells (~5%).

Western Blotting 293T or hTM-T cells were transfected with plasmids expressing wtMYOC, MYOC mutants P370L and Y437H, RSPO3, and/or shRNAs using Lipofectamine 2000 (Life Technologies). Briefly, cells were lysed into 50-100 µL RIPA buffer containing a protease inhibitor cocktail. 10-13 µL of cell lysates were analyzed by SDS-PAGE followed by immunoblotting using the iBlot rapid transfer system (Life Technologies). The blot was blocked using Tris Buffered Saline, 0.05% Tween 20 (TBST). 0.2% I-Block (Casein-based blocking reagent; Life Technologies) and incubated with a mouse anti-human MYOC antibody. The blot was then incubated with an anti-mouse HRP labeled antibody (R&D Systems, Minneapolis, Minn.). Immunoreactive bands were visualized using ECL Chemiluminescent Substrate (Thermo Fisher) and visualized on BioMax XAR film (Carestream Health) developed with a Kodak X-Omat 2000 Processor.

Luciferase Reporter Assay 293T or hTM-T cells were seeded into Costar 96 well white or black wall plates at $2 \times 10^4$ cells/well. Transfections were performed 1-2 days post cell seeding using Fugene HD transfection reagent (Promega, Madison, Wis.) according to the manufacturer's protocol.

Briefly, the Topflash reporter plasmid (Millipore, Billerica, Mass.) containing a 40:1 ratio of the Tcf/lef regulated Firefly Luciferase reporter gene and the cytomegalovirus (CMV) driven *Renilla* Luciferase gene was mixed 1:1 with target plasmids. 8 µL of Fugene HD reagent was added, and samples were immediately vortexed then incubated for 15 minutes at room temperature. Plasmid DNA complexes were added to the cells and incubated at 37° C. for 24 hours. Samples were either unstimulated or stimulated with 400 ng/mL of recombinant human or mouse wnt3a protein (R&D Systems) and incubated for an additional 20-24 hours. Wnt signaling was measured using the Dual Luciferase Assay System (Promega) according to the manufacturer's protocol. Absorbance values were measured on a Centro $XS^3$ 960 microplate luminometer (Berthold Technologies, Oak Ridge, Tenn.) and reported as relative light units (RLUs). To control for transfection efficiency, firefly luciferase RLUs were normalized against *Renilla* luciferase RLUs. All samples were performed in triplicate wells.

Results

Wild-type MYOC (wtMYOC) is secreted from cultured cells, but little to no MYOC is secreted from cells expressing five different mutant forms of MYOC, and it has been reported that co-transfection of cultured cells with normal and mutant MYOC suppresses wtMYOC secretion (Jacobson et al. (2001) *Hum. Mol. Genet.* 10(2):117-25). In order to examine the effects of mutant MYOC expression on MYOC secretion, 293 cells were transfected with plasmids expressing wild-type MYOC, P370L mutant MYOC, or Y437H mutant MYOC.

As shown in FIG. 1, 293 cells expressing wild-type MYOC showed detectable MYOC protein expression in both cell lysates (see bottom blot labeled "CELLS") and secreted into the cell culture medium (see top blot labeled "MEDIUM"). However, cells transfected with plasmids expressing P370L or Y437H MYOC showed intracellular expression but no secretion into the cell culture medium. Moreover, co-transfection of 293 cells with plasmids expressing wild-type MYOC and either P370L or Y437H MYOC caused a lack of MYOC secretion into the cell culture medium. These results suggest that the P370L and Y437H mutants fail to be secreted from 293 cells and are also able to block the secretion of wild-type MYOC.

Figure 2:
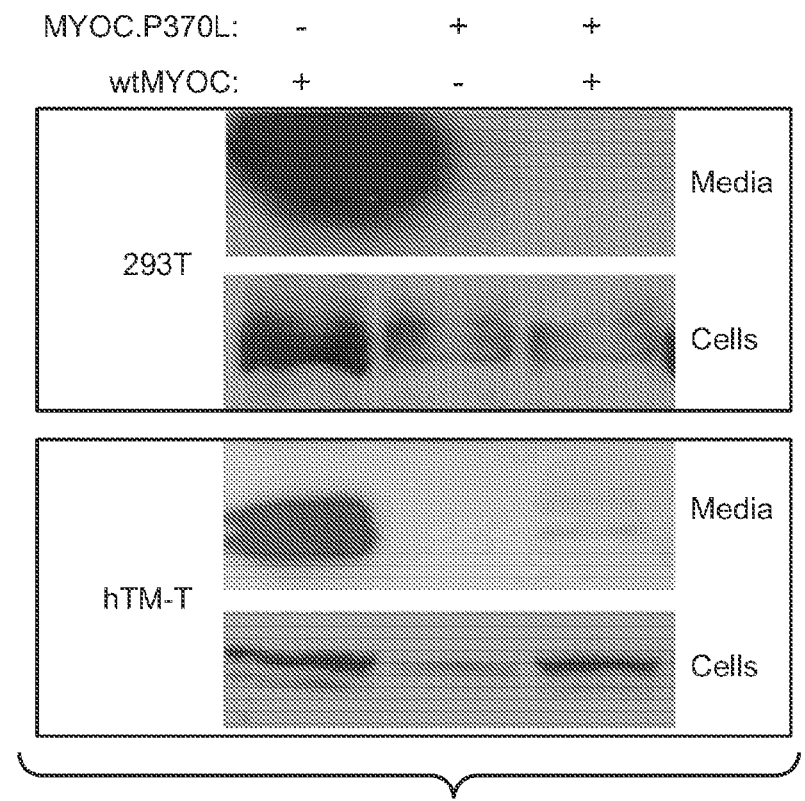
FIG. 2 shows that MYOC mutant P370L is not secreted and blocks the secretion of wild-type MYOC ("wtMYOC") in both 293T and SV40 T-antigen-transformed human trabecular meshwork ("hTM-T") cells. Cell culture medium or cell lysates from 293T or hTM-T cells transfected with constructs expressing wtMYOC and/or P370L MYOC (as labeled) were probed by Western blotting using anti-human MYOC antibody.

Further experiments were undertaken to determine whether these results are observed in human eye cells. A human trabecular meshwork cell line was immortalized by AAV-mediated expression of the SV40 Large T-antigen (hTM-T cells), as described above. 293T and hTM-T cells were transfected with a plasmid expressing wild-type MYOC, a plasmid expressing P370L MYOC, or transfected with both plasmids. FIG. 2 shows Western blots probing the presence of intracellular or secreted MYOC protein in these cells. While wild-type MYOC was expressed and secreted by 293T and hTM-T cells, P370L MYOC was expressed but not secreted by both 293T and hTM-T cells. P370L MYOC also blocked the secretion of wild-type MYOC in both 293T and hTM-T cells.

These results demonstrate that glaucomatous MYOC mutants (e.g., P370L and Y437H) are able to block secretion of wild-type MYOC in human cells. Moreover, mutant MYOC is also able to block MYOC secretion in hTM cells.

Example 2: Glaucomatous MYOC Mutations (e.g., P370L and Y437H) Block Wnt Signaling MYOC is thought to interact with components of the Wnt signaling pathways such as Wnt receptors of the Frizzled (Fzd) family, Wnt antagonists of the secreted Frizzled-related protein (sFRP) family, and Wnt inhibitory factor 1 (WIF-1)), which modulate the organization of actin cytoskeleton stimulating the formation of stress fibers (Kwon et al. (2009) *Mol. Cell. Biol.* 29:2139-54). The formation of stress fibers is critical for the contractility of the trabecular meshwork (TM) and IOP regulation. However, precisely how MYOC is connected to Wnt signaling, and how this connection affects IOP, are unclear. Based on cell biological experiments, a role of myocilin as a matricellular protein has been proposed (Resch and Fautsch, 2009; Koch et al, 2014). Other groups have demonstrated that myocilin is a mediator of oligodendrocyte differentiation and is involved in the myelination of the optic nerve in mice (Kwon et al., 2014).

It was suggested that MYOC may serve as a modulator of Wnt signaling and that Wnt proteins may compensate for an absence of myocilin by performing its functions (Kwon et al. (2009) *Mol. Cell. Biol.* 29:2139-54). Several groups reported similarities between actions of myocilin and Wnt proteins acting through a b-catenin-independent mechanism (Kwon and Tomarev (2011) *J. Cell. Physiol.* 226(12):3392-402). It was reported that reduced Wnt signaling in glaucomatous TM (GTM) cells is due to higher endogenous levels of sFRP1 (Wang et al. (2008) *J. Clin. Invest.* 118:1056-64; Lin and Hankenson (2011) *J. Cell. Biochem.* 112:3491-501). Another group has shown that Wnt signaling pathway protects retinal cell line RGC-5 from elevated pressure (Fragoso et al. (2011) *Cell. Mol. Neurobiol.* 31(1):163-73).

It is unclear from the literature whether glaucomatous MYOC mutations (e.g., P370L or Y437H) have any effect on Wnt signaling in the TM. One report has stated that the effect of glaucomatous MYOC mutations, which inhibit MYOC secretion from the TM, on Wnt signaling in the TM is unclear, as measured by the TOP-Flash Wnt signaling assay (Mao et al. (2012) *Invest. Ophthalmol. Vis. Sci.* 53(11):7043-51). Another group has reported that P370L had a stimulating effect on Wnt signaling in Caco-2 cells, shown by TOP-Flash Wnt signaling assay (Shen et al. (2012) *PLoS ONE* 7(9):e44902).

In contrast, the inventors have discovered that MYOC mutations (e.g., P370L and Y437H) have an inhibitory effect on Wnt signaling in 293 and TM cells, as shown by TOP-Flash Wnt signaling assay, which reports beta-catenin activity.

To evaluate the effect of MYOC P370L and Y437H mutants on Wnt signaling, 293T cells were co-transfected with TOP-Flash reporter construct and wtMYOC ("MYOC"), P370L MYOC, or Y437H MYOC plasmids. Wnt signaling was amplified after addition of recombinant mouse Wnt3a (400 ng/ml) and measured by TOP-Flash assay. Luciferase activity (mean±SD, n=4) was measured post transfection and was normalized to the transfection control of constitutively expressed *Renilla* luciferase level.

Figure 3:
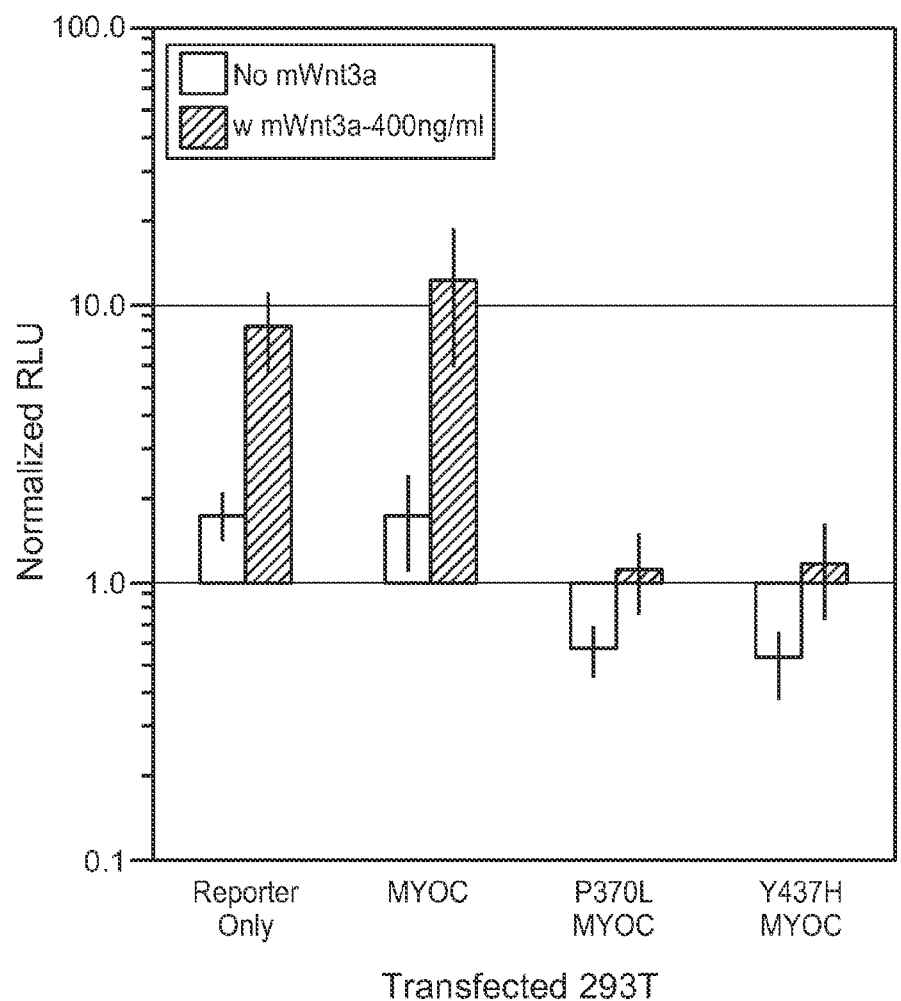
FIG. 3 depicts the effect of wtMYOC, P370L MYOC, or Y437H expression on Wnt signaling. For each experiment, the "no mWnt3a" bar is on the left, and the "w mWnt3a-400 ng/ml" bar is on the right.

As shown in FIG. 3, stimulation of 293T cells with recombinant mouse Wnt3 caused an increase in the TOP-Flash reporter. Expression of wild-type MYOC did not interfere with Wnt signaling, as assayed by TOP-Flash. However, co-expression of wild-type MYOC with either P370L MYOC or Y437H MYOC blocked TOP-Flash activation in 293T cells. These results indicate that expression of glaucomatous MYOC mutants (e.g., P370L and Y437H) are able to inhibit Wnt signaling in human cells.

Example 3: Restoration of Wnt Signaling Blocked by Glaucomatous MYOC Mutations (e.g., P370L and Y437H)

The previous Example demonstrates that glaucomatous MYOC mutants P370L and Y437H act to block Wnt signaling in human cells. Further experiments were undertaken to examine potential mechanisms by which Wnt signaling may be restored in cells expressing these MYOC mutants.

R-spondin 3 (RSPO3) is a protein encoded by the RSPO3 gene that activates Wnt signaling, and it was examined whether expression of RSPO3 is able to restore Wnt signaling upon its inhibition by mutant MYOC expression. For these experiments, similar to FIG. 3 above, 293T cells were co-transfected with TOP-Flash reporter construct and wtMYOC ("MYOC"), P370L MYOC, Y437H MYOC, and/or RSPO3 plasmids, as labeled. Wnt signaling was amplified after addition of recombinant mouse Wnt3a (400 ng/ml) and measured by TOP-Flash assay. Luciferase activity (mean±SD, n=3) was measured post transfection and was normalized to the transfection control of constitutively expressed *Renilla* luciferase level.

Figure 4:
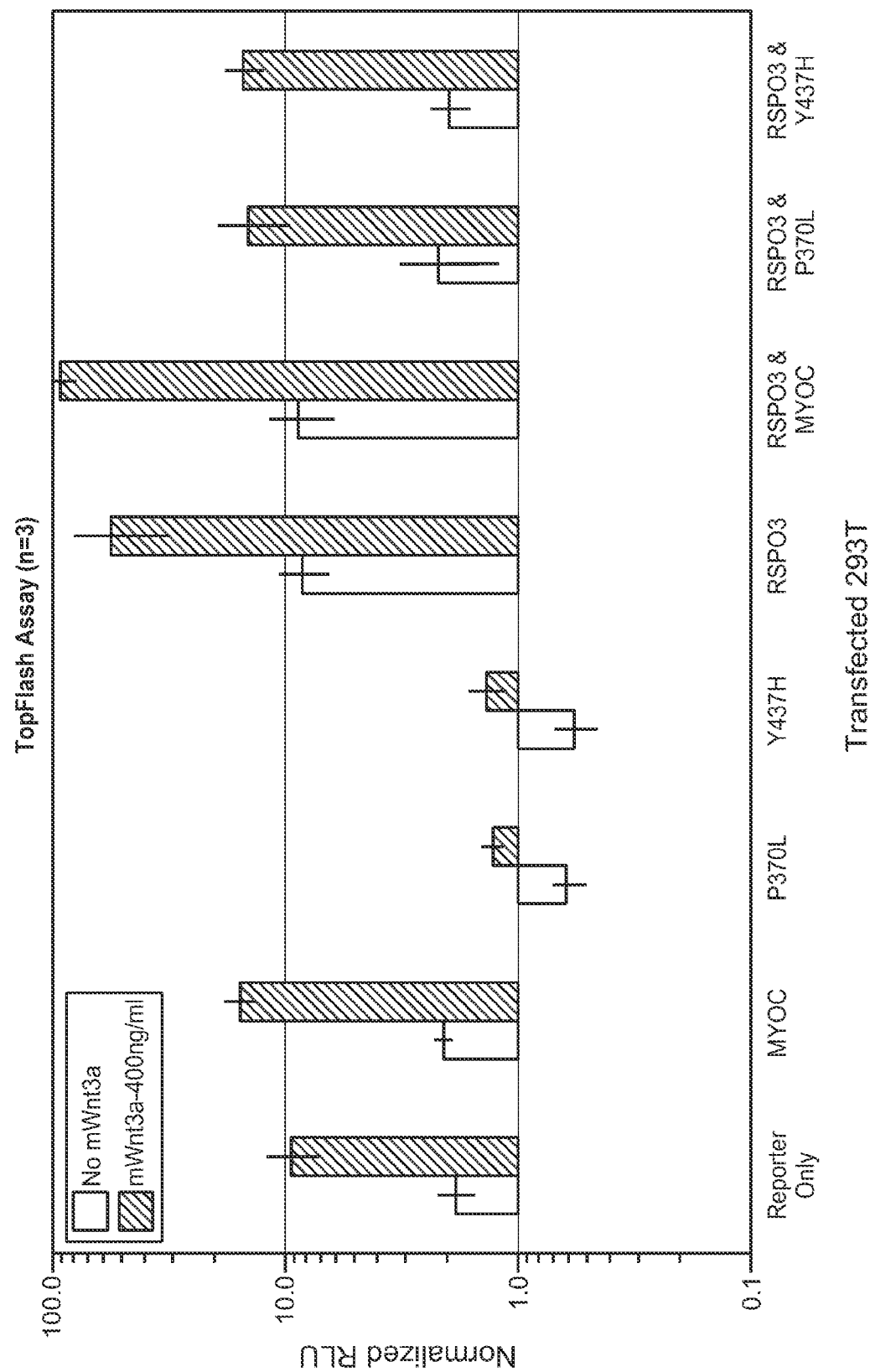
FIG. 4 shows that RSPO3 expression can restore Wnt signaling upon co-expression with P370L or Y437H MYOC. For each experiment, the "no mWnt3a" bar is on the left, and the "mWnt3a-400 ng/ml" bar is on the right.

As shown in FIG. 4, RSPO3 expression caused an increase in Wnt signaling, as measured by TOP-Flash. Importantly, co-expression of RSPO3 and either P370L MYOC or Y437H MYOC was able to restore Wnt signaling, as compared to the inhibition of Wnt signaling observed upon expression of P370L MYOC or Y437H MYOC alone. 293T cells were co-transfected with TOP-Flash reporter construct and wtMYOC ("MYOC"), P370L MYOC, Y437H MYOC, and/or RSPO3 plasmids, as labeled. Wnt signaling was amplified after addition of recombinant mouse Wnt3a (400 ng/ml) and measured by TOP-Flash assay. Luciferase activity was measured post transfection and was normalized to the transfection control of constitutively expressed *Renilla* luciferase level.

Figure 5:
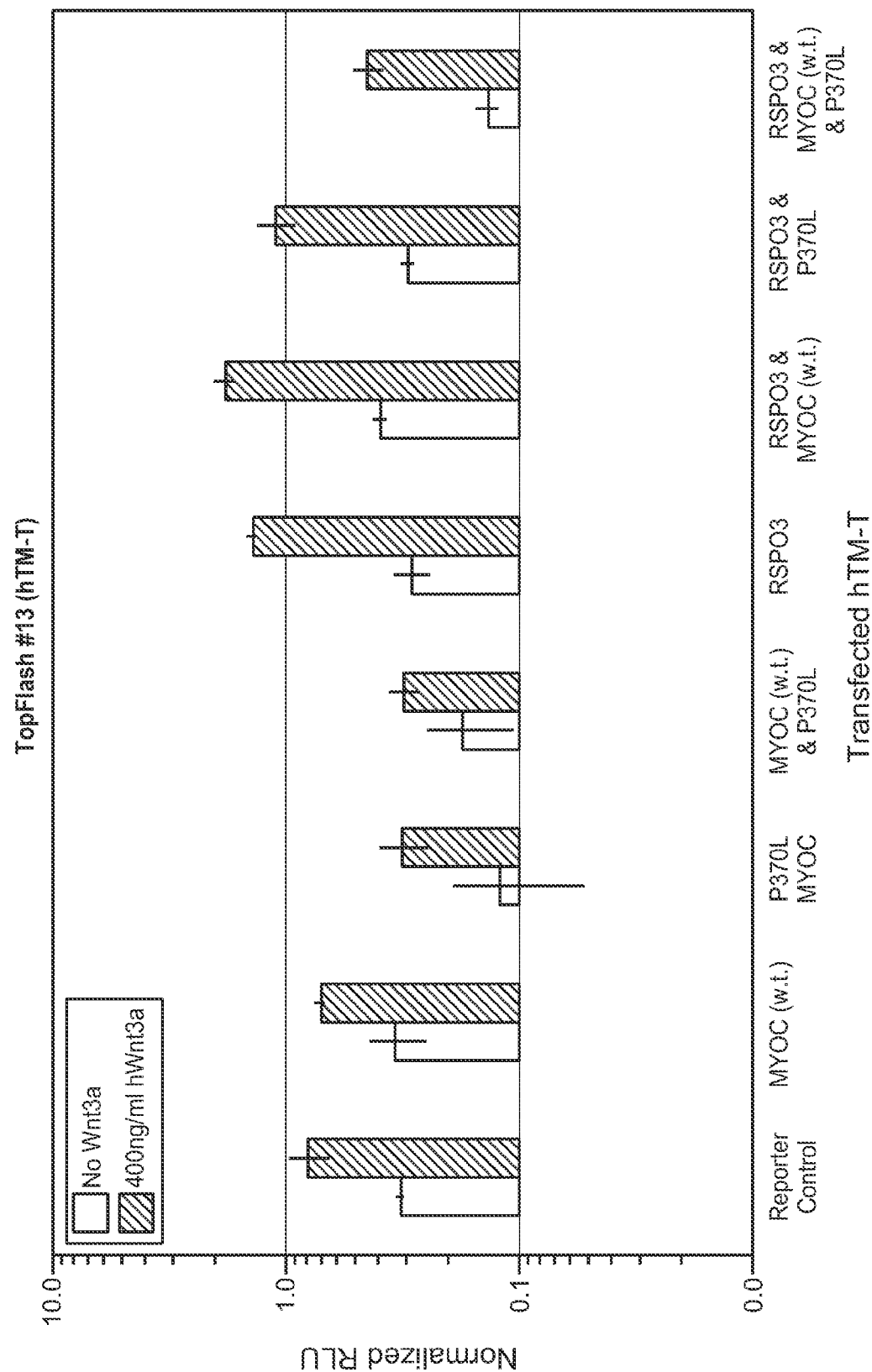
FIG. 5 shows that RSPO3 expression can restore Wnt signaling in hTM-T cells upon co-expression with P370L MYOC. For each experiment, the "no mWnt3a" bar is on the left, and the "400 ng/ml hWnt3a" bar is on the right.

To test whether a similar effect is observed in hTM cells, hTM-T cells were co-transfected with TOP-Flash reporter construct and wtMYOC ("MYOC w.t."), P370L MYOC, and/or RSPO3 plasmids. Wnt activity was measured by TOP-Flash assay as described above (luciferase activity is shown as mean±SD, n=3). FIG. 5 shows that expression of P370L MYOC caused a reduction in Wnt signaling and was able to reduce Wnt signaling in hTM-T cells co-expressing wild-type MYOC. Expression of RSPO3 was able to increase Wnt signaling in hTM-T cells expressing P370L MYOC alone or P370L MYOC in combination with wild-type MYOC. The results depicted in FIGS. 4 and 5 indicate that expression of RSPO3 restores Wnt signaling in cells expressing glaucomatous MYOC mutants, such as 293T and hTM-T cells.

Figure 6:
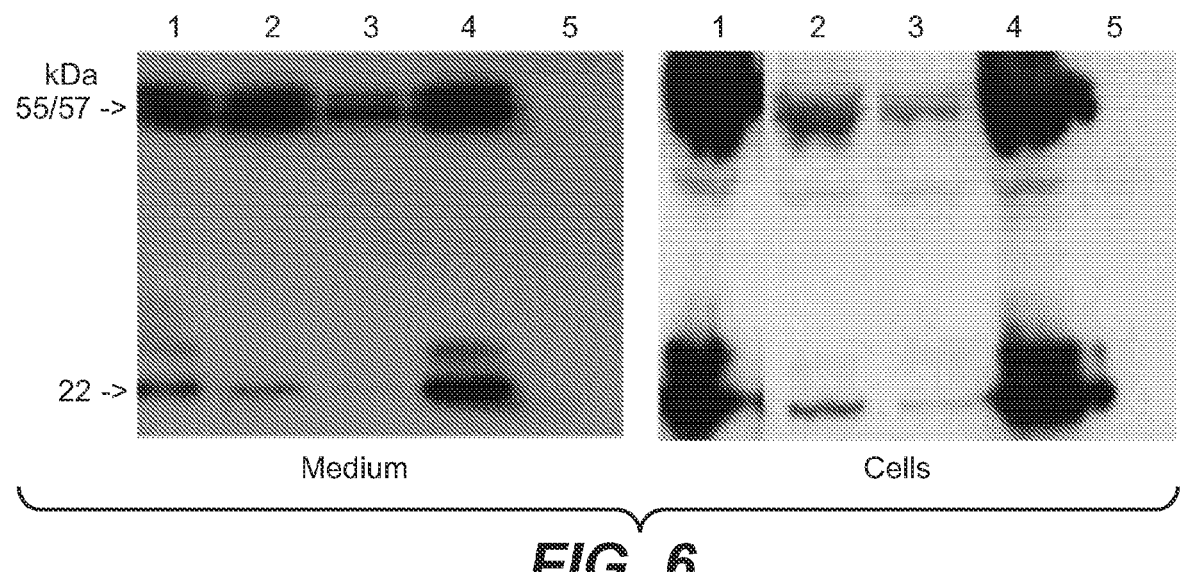
FIG. 6 shows the effect of MYOC shRNA on MYOC expression in 293T cells. Cell culture medium or cell lysates from 293T cells were probed via Western blotting with anti-human MYOC antibody. Cells were transfected with plasmids expressing wtMYOC (lane 1); wtMYOC and MYOC shRNA #79 (2); wtMYOC and MYOC shRNA #93 (3); wtMYOC and scrambled shRNA control (4); or EGFP (5). 55/57 kD bands represent glycosylated (57 kD) and non-glycosylated (55 kD) forms of a full-size MYOC protein. 22 kD band represents N-terminus of a calpain II cleavage product.

Surprisingly, it has also been discovered that Wnt inhibition by expression of glaucomatous MYOC mutants ace be reversed by silencing MYOC (e.g., by RNAi). The effect of MYOC shRNA on MYOC expression was tested in 293T cells. As shown in FIG. 6, MYOC shRNA reduced MYOC protein expression in cells expressing wild-type MYOC, as compared to scrambled shRNA control. This reduction was observed for both intracellular and secreted MYOC.

Figure 7:
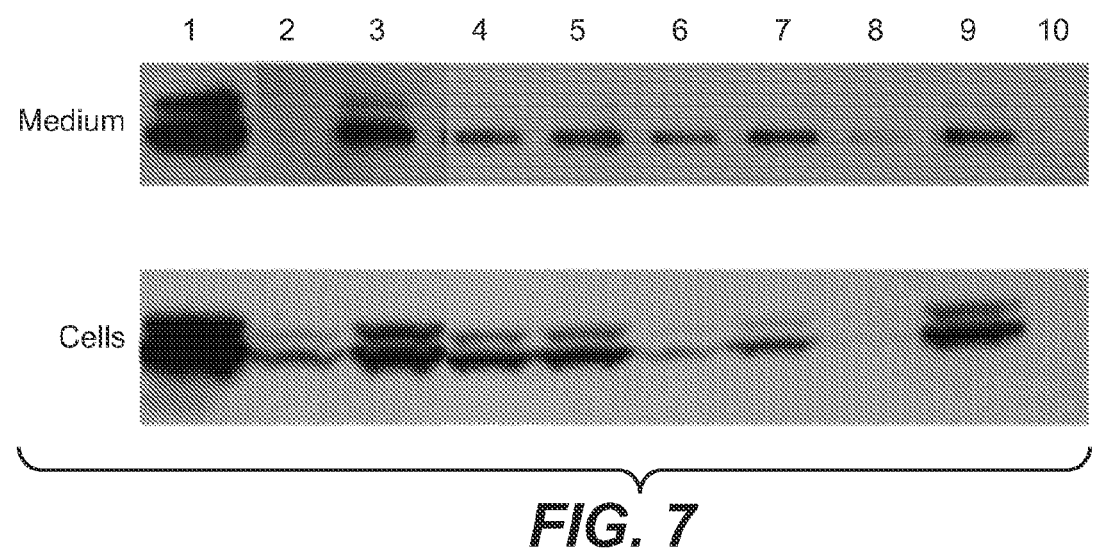
FIG. 7 shows the effect of MYOC shRNA on MYOC expression in hTM-T cells. Cell culture medium or cell lysates from hTM-T cells were probed via Western blotting with anti-human MYOC antibody. Cells were transfected with plasmids expressing wtMYOC (lane 1); P370L MYOC (2); wtMYOC and P370L MYOC (3); wtMYOC and P370L MYOC and Grp94 shRNA #1 (4); wtMYOC and P370L MYOC and Grp94 shRNA #2 (5); wtMYOC and P370L MYOC and MYOC shRNA #53 (6); wtMYOC and P370L MYOC and pGIPZ MYOC shRNA #79 (7); wtMYOC and P370L MYOC and pGIPZ MYOC shRNA #93 (8); wtMYOC and P370L MYOC and scrambled shRNA control (9); or EGFP (10).

FIG. 7 shows the effect of MYOC shRNA in hTM-T cells. MYOC shRNA reduced MYOC protein expression in hTM-T cells co-expressing wild-type and P370L mutant MYOC. This reduction was observed for both intracellular and secreted MYOC. In contrast, shRNA targeting Grp94 had no effect on MYOC expression. Grp94 is a molecular chaperone that is involved in the processing and transport of secreted proteins, and it was recently proposed as a therapeutic for patients suffering from some cases of MYOC glaucoma because Grp94 was thought to facilitate clearance of MYOC mutants (Suntharalingam et al., (2012) *J. Biol. Chem.* 287(48):40661-9). Scrambled shRNA controls similarly had no effect on MYOC expression.

Figure 8:
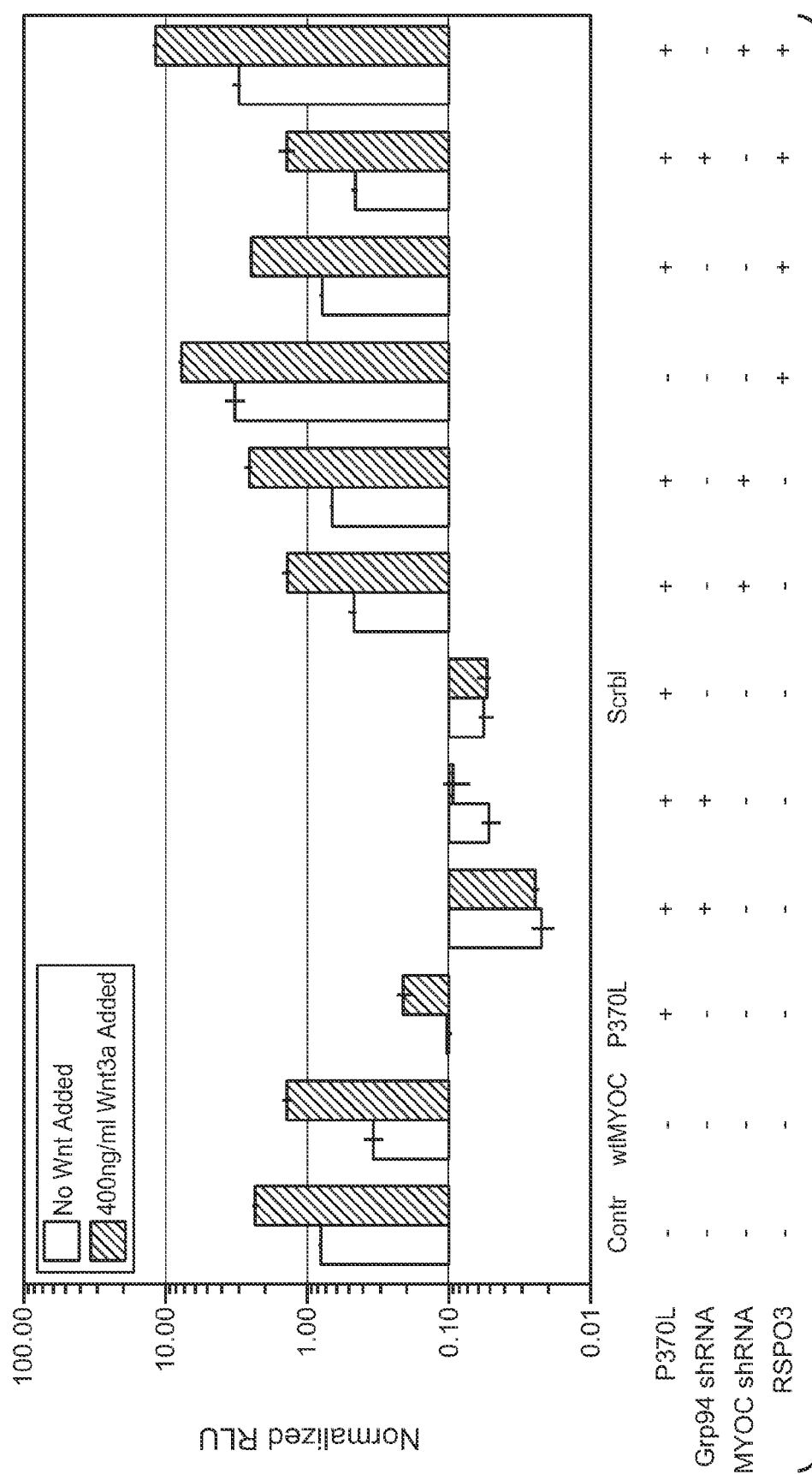
FIG. 8 shows that RSPO3 expression and MYOC silencing synergistically restore Wnt signaling upon co-expression with P370L MYOC. 293T cells were co-transfected with TOP-Flash reporter construct and wtMYOC ("MYOC"), plus P370L MYOC, Grp94 shRNA, pGIPZ MYOC shRNAs #79 (the first) and #93 (the second), and/or RSPO3 plasmids, as labeled. Wnt signaling was amplified after addition of recombinant mouse Wnt3a (400 ng/ml) and measured by TOP-Flash assay. Luciferase activity (mean±SD, n=1-3 replicate wells) was measured post transfection and was normalized to the transfection control of constitutively expressed *Renilla* luciferase level. For each experiment, the "no Wnt added" bar is on the left, and the "400 ng/ml Wnt3a added" bar is on the right.

Since MYOC shRNA affected MYOC expression, its effects on Wnt signaling were next investigated. As shown in FIG. 8, expression of P370L MYOC reduced Wnt signaling in 293T cells. Grp94 shRNA and scrambled shRNA controls were unable to restore Wnt signaling inhibited by P370L MYOC. In contrast, MYOC shRNA increased Wnt signaling in cells expressing P370L MYOC to approximately wild-type levels (i.e., level of Wnt signaling observed in control cells not expressing P370L MYOC, as measured by TOP-Flash). Expression of RSPO3 was also found to increase Wnt signaling in cells expressing P370L MYOC, and combining expression of RSPO3 with MYOC RNAi (e.g., shRNA) led to a synergistic increase in Wnt signaling in cells expressing P370L MYOC.

Although inhibition of Grp94 has been proposed as a mechanism to reduce the effects of MYOC mutants, these results described herein indicate that expression of RSPO3 and/or MYOC shRNA can be more effective in de-repressing Wnt signaling in the presence of MYOC mutant expression.

Figure 9:
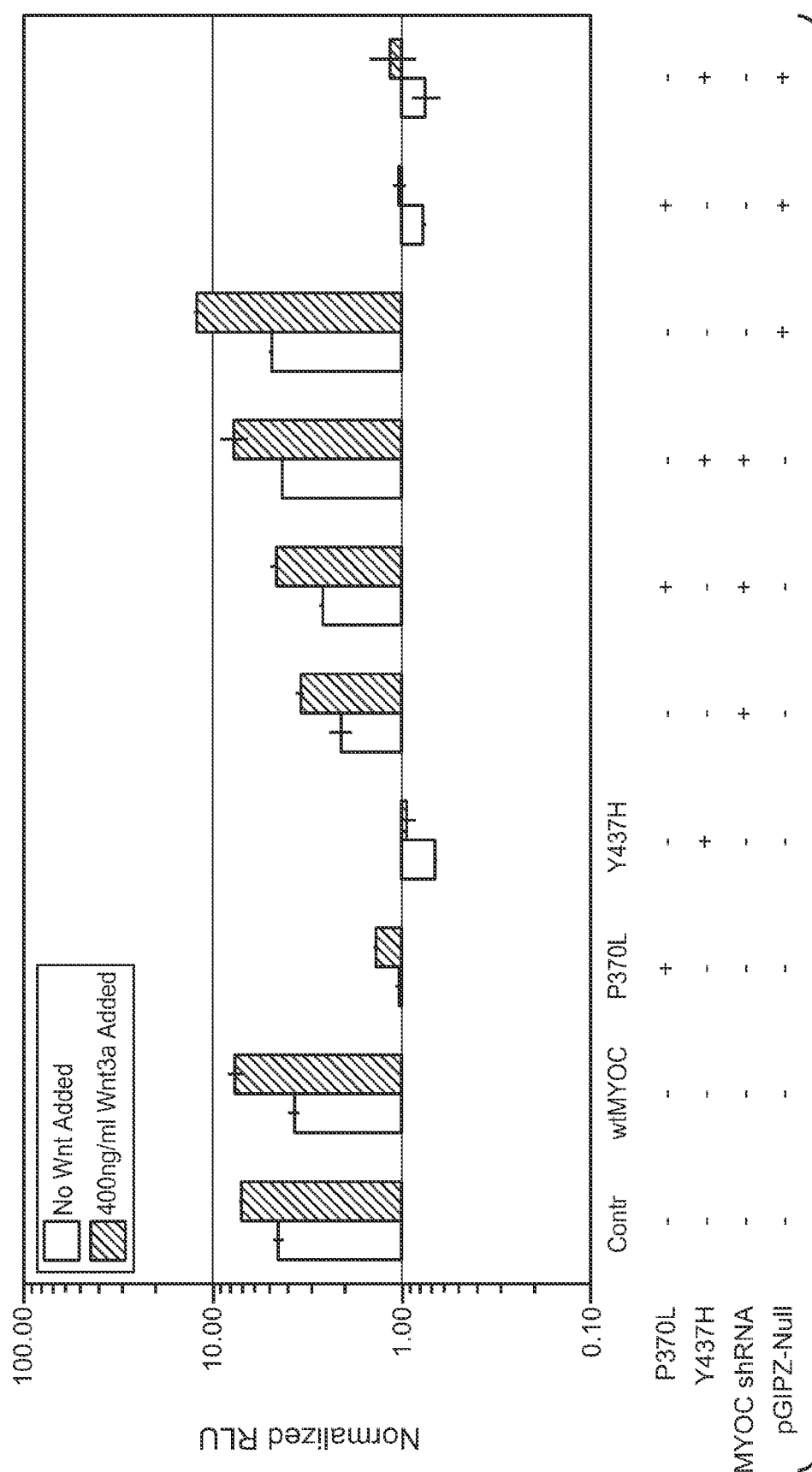
FIG. 9 shows that MYOC silencing restores Wnt signaling upon co-expression with P370L or Y437H MYOC. 293T cells were co-transfected with TOP-Flash reporter construct and wtMYOC ("MYOC"), plus P370L MYOC, Y437H MYOC, MYOC shRNA, and/or scrambled control shRNA ("pGIPZ-Null"), as labeled. Wnt signaling was amplified after addition of recombinant mouse Wnt3a (400 ng/ml) and measured by TOP-Flash assay. Luciferase activity (mean±SD, n=1-3 replicate wells) was measured post transfection and was normalized to the transfection control of constitutively expressed *Renilla* luciferase level. For each experiment, the "no Wnt added" bar is on the left, and the "400 ng/ml Wnt3a added" bar is on the right.

The effect of MYOC shRNA on Wnt signaling in cells expressing Y437H MYOC was also examined. As shown in FIG. 9, expression of P370L or Y437H MYOC reduced Wnt signaling in 293T cells. However, MYOC shRNA was able to restore Wnt signaling in cells expressing either P370L or Y437H MYOC. This effect was not observed upon expression of a scrambled shRNA control.

In summary, these results demonstrate that Wnt signaling blocked by MYOC mutants (e.g., P370L and Y437H) can be restored by R-spondin 3 (RSPO3) expression and/or inhibiting MYOC (e.g., by RNAi).

Example 4: AAV2 R471A Transduces Cells of the Trabecular Meshwork

Figure 10:
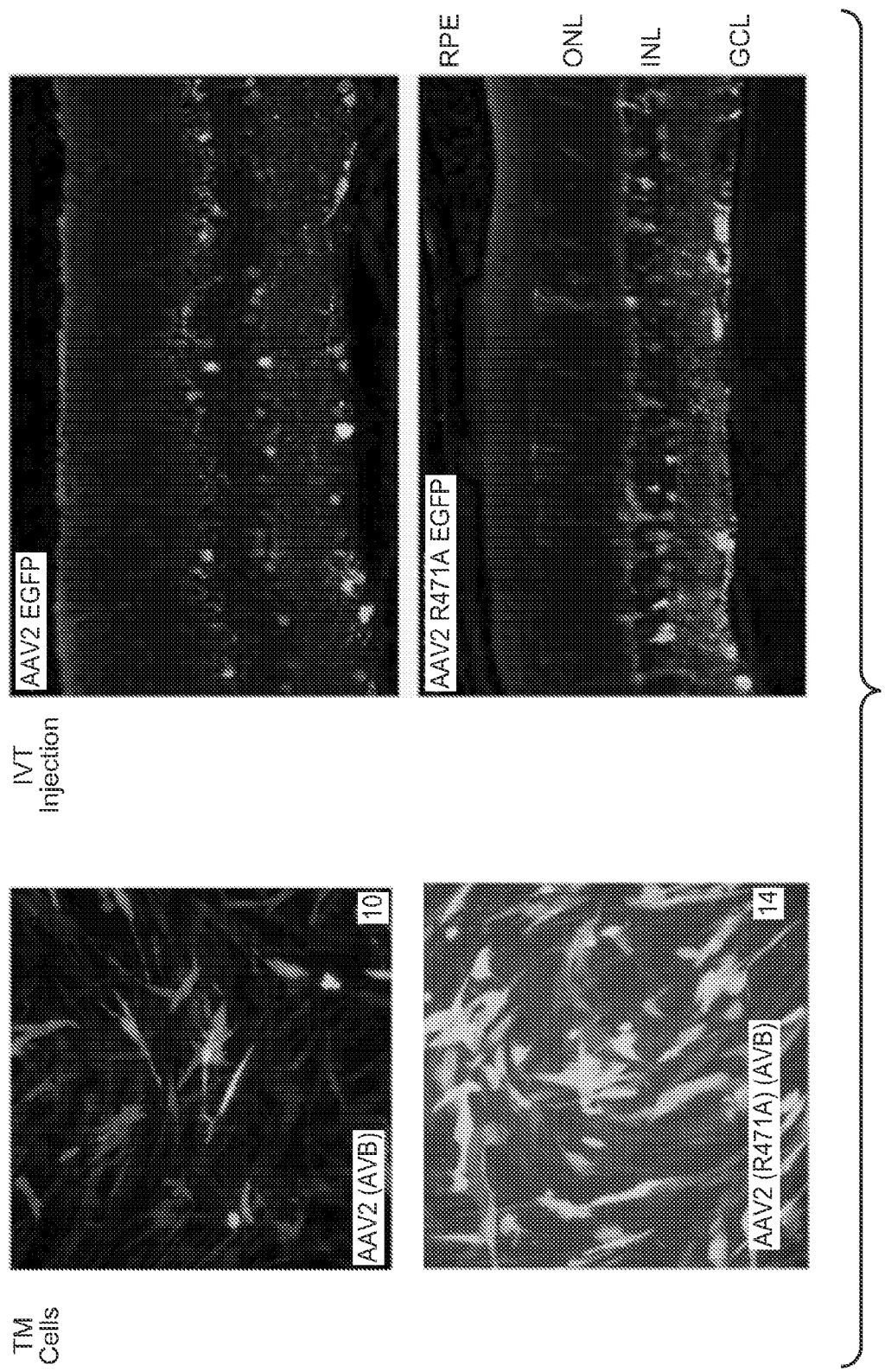
FIG. 10 shows in vitro (left panels) and in vivo (right panels) transduction of cells of the trabecular meshwork by wild-type AAV2 viral particles (top panels) and AAV2 particles comprising a R471A amino acid substitution of capsid protein.

To determine if AAV particles could transduce cells of the trabecular meshwork, AAV2 vectors encoding EGFP were packaged into wildtype AAV2 particles of AAV2 particles comprising a R471A amino acid substitution (numbering based on VP1). Viral particles were evaluated in vitro by treating hTM cells (described above) with AAV2 EGFP and AAV2 R471A EGFP. As shown in FIG. 10 (left panels), AAV2 R471A EGFP showed higher TM cell transduction compared to wild-type AAV2. To evaluate TM cell transduction in vivo, AAV2 EGFP and AAV2 R471A EGFP were injected into the eyes of mice. Mice were then sacrificed and analyzed for EGFP expression. As shown in FIG. 10 (right panels), AAV2 R471A EGFP showed higher TM cell transduction in vivo compared to wild-type AAV2.

Example 5: RSPO3 Expression or MYOC shRNA in Animal Models of Myocilin (MYOC) Glaucoma The above Examples demonstrate that glaucomatous MYOC mutations (e.g., P370L and Y437H) block Wnt signaling, and that this inhibition of Wnt signaling may be reversed by R-spondin 3 (RSPO3) expression or MYOC shRNA. Without wishing to be bound by any particular theory, it is thought that MYOC mutations (e.g., P370L and/or Y437H) may effect Wnt signaling in the TM, thereby modulating IOP and contributing to POAG. The following experiments test whether R-spondin 3 (RSPO3) expression or MYOC shRNA, delivered via AAV2 vector, is able to improve glaucoma symptoms in mouse models of the disease.

A mouse model of POAG is used to examine the efficacy of AAV-mediated delivery of R-spondin 3 (RSPO3) expression and/or MYOC shRNA to the eye in treating myocilin (MYOC) glaucoma. For example, a mouse model expressing Y437H MYOC may be used (see Zode et al. (2011) *J. Clin. Invest.* 121(9):3542-53). In this model, human Y437H MYOC is expressed under control of the CMV promoter in a transgenic mouse. Using this system, Y437H MYOC is expressed in tissues related to myocilin (MYOC) glaucoma, such as the trabecular meshwork and the sclera. These mice exhibit grossly normal eye morphology but begin to show myocilin (MYOC) glaucoma-like symptoms after three months of age, such as increased IOP and progressive, axonal degeneration of the optic nerve.

Transgenes expressing GFP, mouse RSPO3, shRNA targeting mouse MYOC (MYOC shRNA target and loop sequence from plasmid pGIPZ #93; Dharmacon, GE Healthcare), or scrambled shRNA are cloned into an AAV2 genome under the control of a hybrid chicken β-actin (CBA) promoter from plasmid pCBA(2)-int-BGH, which also contains the bovine growth hormone polyadenylation signal sequence (Xu, R., et al. (2001) *Gene Ther.* 8:1323-32). The expression cassette is then cloned into a previral plasmid vector pAAVSP70 containing AAV2 inverted terminal repeats (ITRs) (Ziegler, R. J., et al. (2004) *Mol. Ther.* 9:231-40). The total size of the resulting AAV genome in plasmid sp70.BR/sFLT01 including the region flanked by ITR is 4.6 kb.

AAV2 genomes are packaged into AAV2 capsids with R471A mutation to allow infection of the trabecular meshwork or wild-type AAV2 capsids to allow infection of the retinal ganglion cells. AAV2 genomes are packaged into the AAV2 wild-type or R471A capsid using the "gutless" vector approach using a triple transfection method (see, e.g., Xiao et al. (1998) *J. Virol.*, 3:2224-32). Briefly, the rep and cap genes are replaced with the therapeutic gene and its regulatory elements, both sandwiched between a 5' and 3' inverted terminal repeat (ITR). The rep and cap genes are provided in trans on a separate plasmid, and a third plasmid contributes the required adenoviral helper genes. Alternatively, the required helper genes are provided by a replication deficient adenovirus and/or adenoviral helper genes are stably integrated into the host cell genome. Without wishing to be bound by any particular theory, it is postulated that the viral capsids are fully assembled, and the ITR flanked vector genome is then inserted into the capsid via a capsid pore (Myers & Carter (1980) *Virology,* 102:71-82). Genome-containing capsids are then formulated for injection.

Transgenic mice expressing human Y437H MYOC are grown to approximately three months of age and then randomly assigned into treatment groups. Mice are anesthetized and injected via intravitreal or intracameral injection with AAV vectors encoding GFP, mouse RSPO3, shRNA targeting mouse MYOC, or scrambled shRNA. In one treatment group, to test effects in retinal ganglion cells, a mouse receives an injection of AAV2 vectors with wild-type AAV2 capsid expressing mouse RSPO3 and an injection of AAV2 vectors with wild-type AAV2 capsid expressing GFP in the contralateral eye. In one treatment group, to test effects in the trabecular meshwork, a mouse receives an injection of AAV2 vectors with R471A AAV2 capsid expressing shRNA targeting mouse MYOC and an injection of AAV2 vectors with R471A AAV2 capsid expressing scrambled shRNA in the contralateral eye. In one treatment group, a mouse receives an injection of a mixture of AAV vectors expressing mouse RSPO3 and AAV vectors expressing shRNA targeting mouse MYOC in one eye and an injection of AAV vectors expressing GFP and/or AAV vectors expressing scrambled shRNA in the contralateral eye. In one treatment group, a mouse receives an injection of AAV vectors expressing mouse RSPO3 and expressing shRNA targeting mouse MYOC in one eye and an injection of AAV vectors expressing GFP and expressing scrambled shRNA in the contralateral eye.

Mice are examined at regular intervals following injection for myocilin (MYOC) glaucoma symptoms, comparing the eye receiving experimental treatment to the eye receiving control treatment. IOP is measured by tonometry (Kim, C. Y., et al. (2007) *Eye* (Lond.) 21(9):1202-9). Corneal thickness is measured by ultrasound pachymeter (Lively, G. D., et al. (2010) *Physiol. Genomics* 42(2):281-6). Iridocorneal angle is assessed by gonioscopy. Retinal ganglion cell function is measured by analyzing pattern electroretinography responses to visual stimuli using pattern electroretinography (PERG) (Zode et al. (2011) *J. Clin. Invest.* 121(9): 3542-53). Mice may be sacrificed and eyes dissected for other phenotypic characterizations. For example, retinal ganglion cell number and/or morphology are assessed by immunofluorescence microscopy and/or transmission electron microscopy.

Example 6: Use of RSPO Family Proteins to Restore Wnt Signaling Blocked by Glaucomatous MYOC Mutation As demonstrated in Example 3, Wnt signaling blocked by MYOC mutants (e.g., P370L and Y437H) can be restored by R-spondin 3 (RSPO3) expression. To further understand the mechanisms underlying this restoration of Wnt signaling, the ability of different RSPO family members and variants to restore Wnt signaling was examined.

Figure 11:
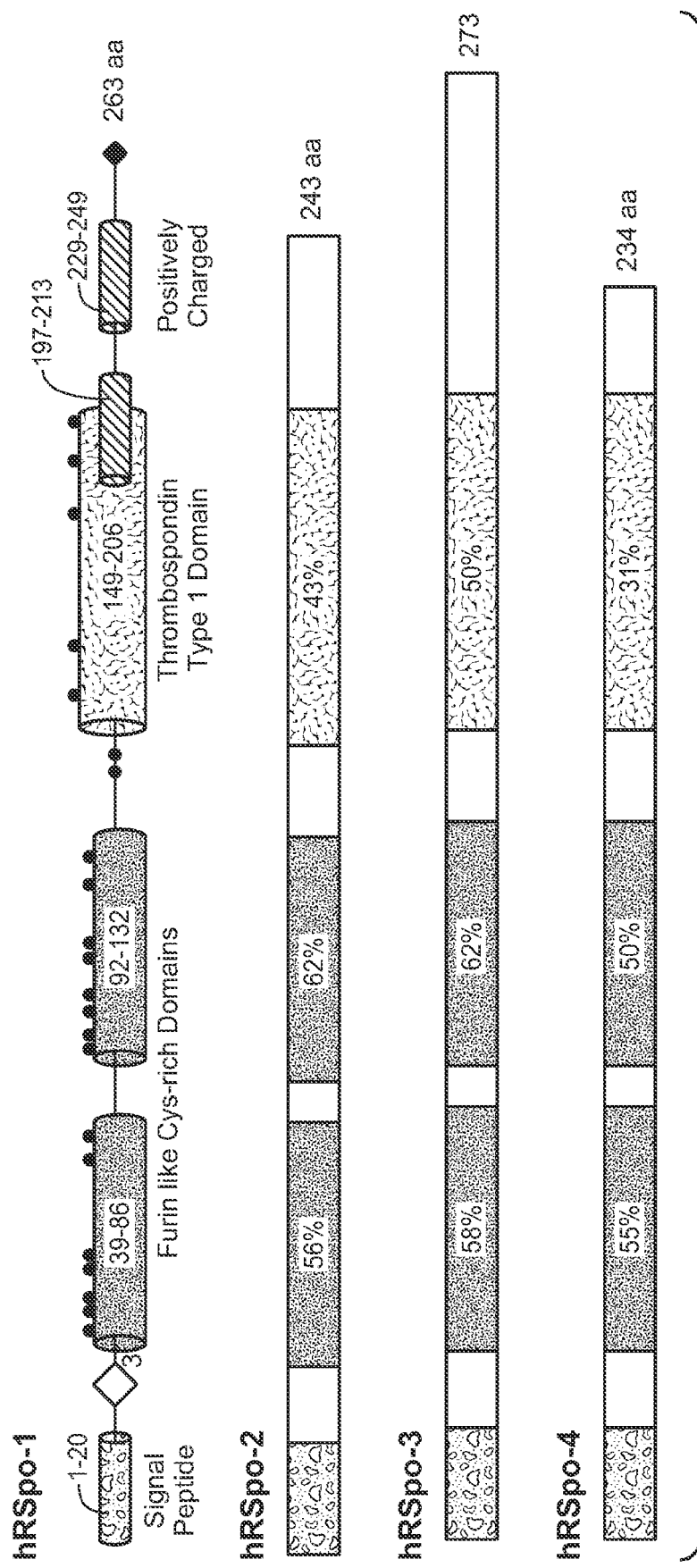
FIG. 11 shows a domain diagram of human RSPO family proteins depicting furin-like Cys rich domains, the thrombospondin type1 domain, and the C-terminal positively charged domain, as labeled (figure adapted from Kim, K. A. et al. (2008) *Mol. Biol. Cell.* 19:2588-2596).
Figure 12:
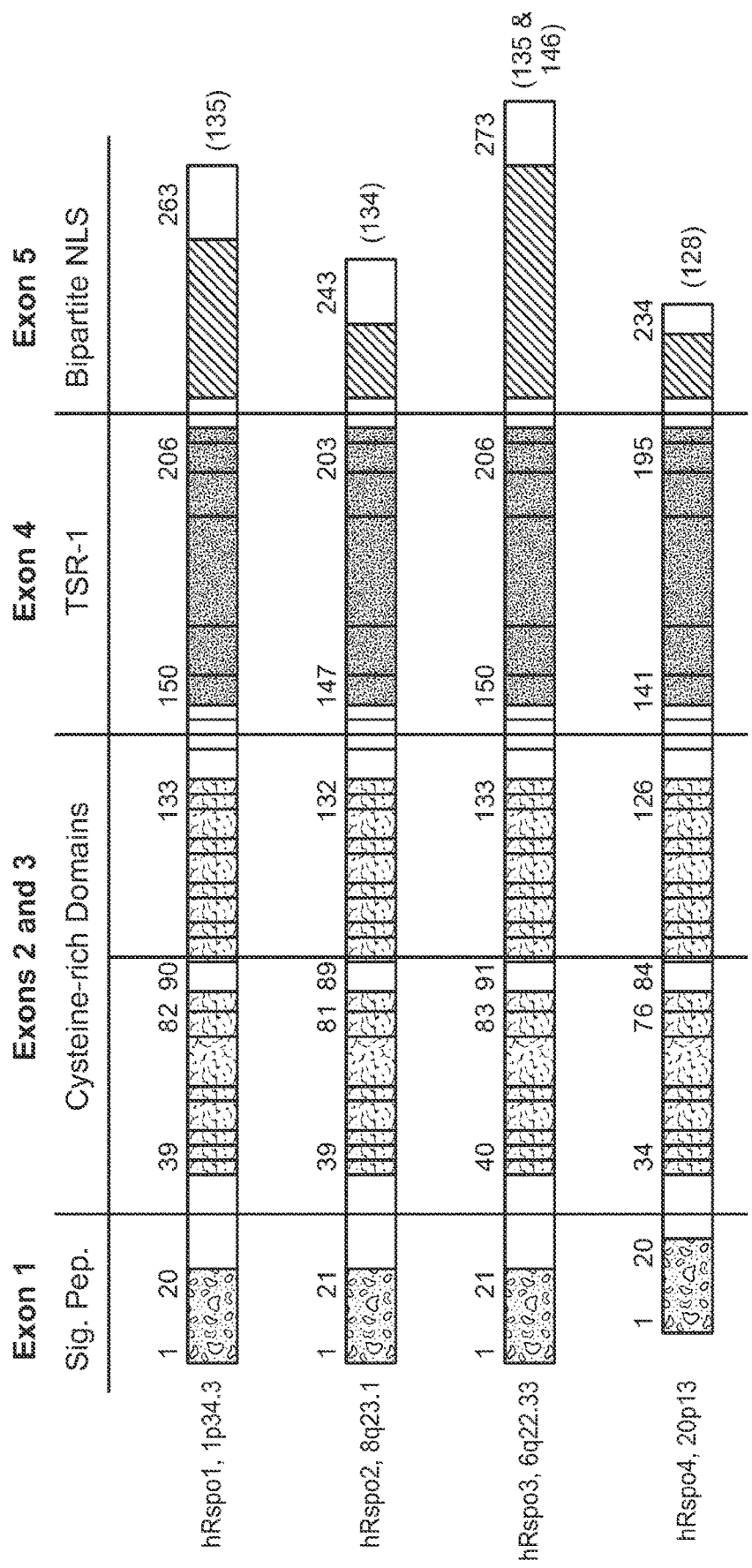
FIG. 12 shows a domain diagram of human RSPO family genes depicting the protein domains listed in FIG. 11. Amino acid sequence numbering is depicted, and truncated mutants tested for each family member are as labeled (figure adapted from Kim, K. A. et al. (2006) *Cell Cycle* 5:23-26).
Figure 14:
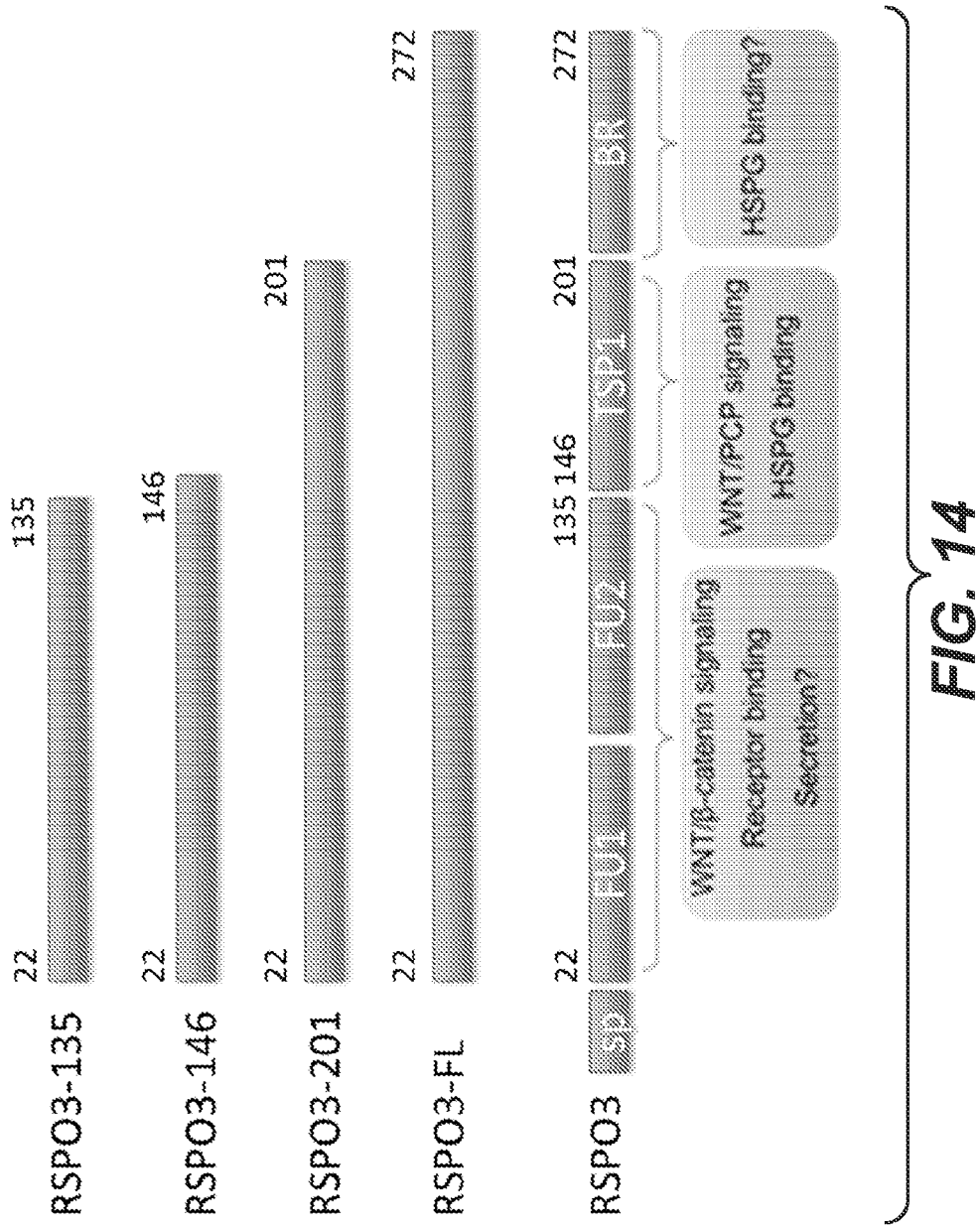
FIG. 14 depicts the hRSPO3 fragments tested. The domain structure of full-length hRSPO3 with signal peptide, FU1, FU2, TSP1, and BR domains labeled and putative functions for each domain are also provided below.

Human RSPO family proteins hRSPO1, 2, 3, and 4 share a similar domain structure that includes furin-like Cys rich domains, a thrombospondin type I domain, and a C-terminal positively charged domain, as illustrated in FIGS. 11 & 12. To examine the functional domains required for restoration of Wnt signaling, several truncated variants of human RSPO3 were generated. The variants, and the specific domains included and excluded in each variant, are shown in FIGS. 11, 12, 13A and 14.

Figure 15:
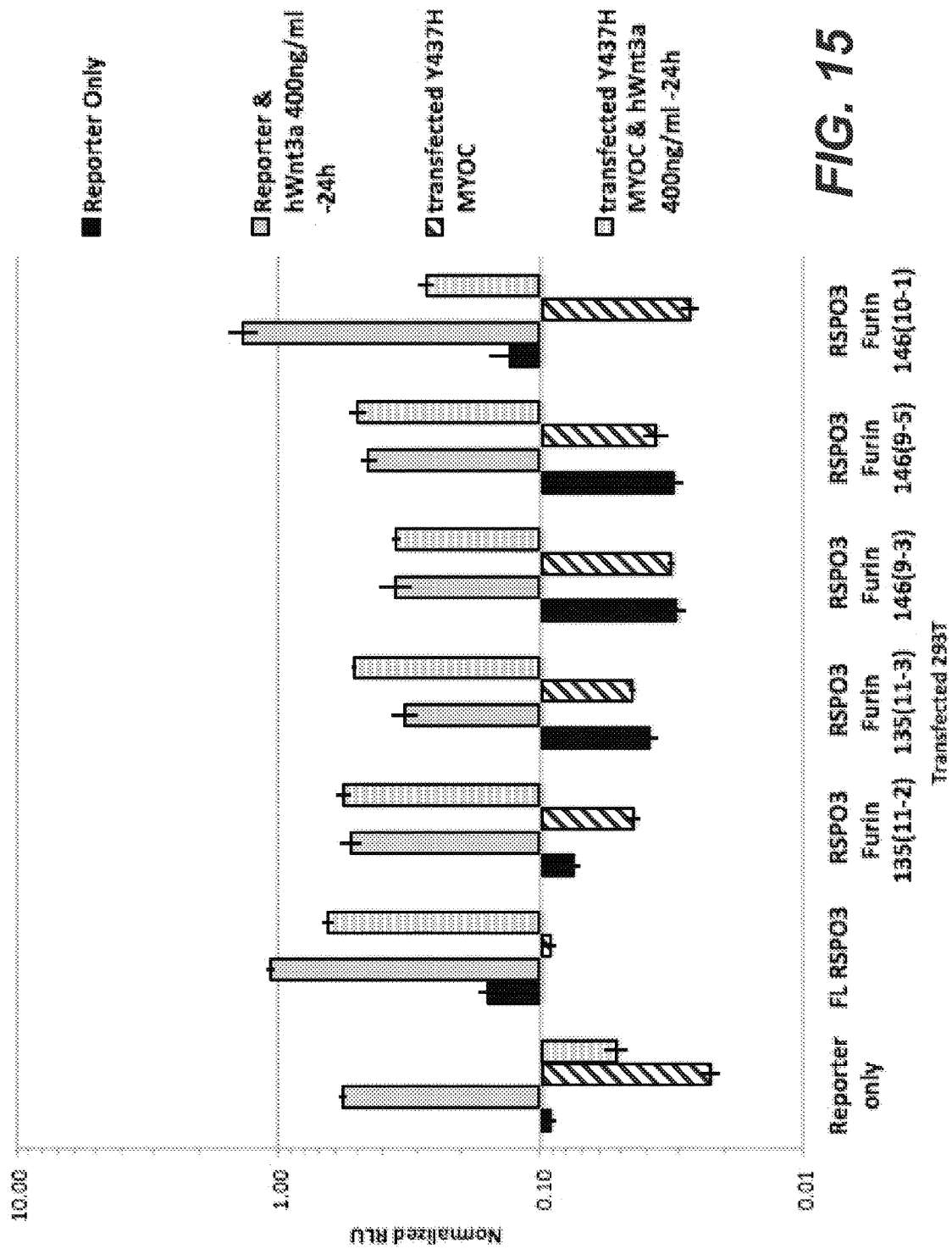
FIG. 15 shows that expression of full-length RSPO3 and RSPO3 fragments can restore Wnt signaling upon co-expression with Y437H MYOC.

To test the effect of the RSPO3 variants on Wnt signaling, 293T cells were co-transfected with TOP-Flash reporter construct and wtMYOC ("MYOC") or Y437H MYOC, and also transfected with full length or partial RSPO3 plasmids, as labeled in FIG. 15. Wnt signaling was amplified after addition of recombinant human Wnt3a (400 ng/ml) and measured by TOP-Flash assay. Luciferase activity (mean±SD, n=3) was measured post transfection and was normalized to the transfection control of constitutively expressed *Renilla* luciferase level.

As described in Example 3, mutant MYOC Y437H inhibits Wnt signaling in 293T cells as measured by TOP-Flash assay. FIG. 15 shows the effect of the various hRSPO3 truncated variants on Wnt signaling in this assay. As shown in FIG. 15, all hRSPO3 forms tested, both partial and full-length, had Wnt restoring activity with full-length RSPO3 exhibiting more potent activity than many of the truncated forms.

Figure 16:
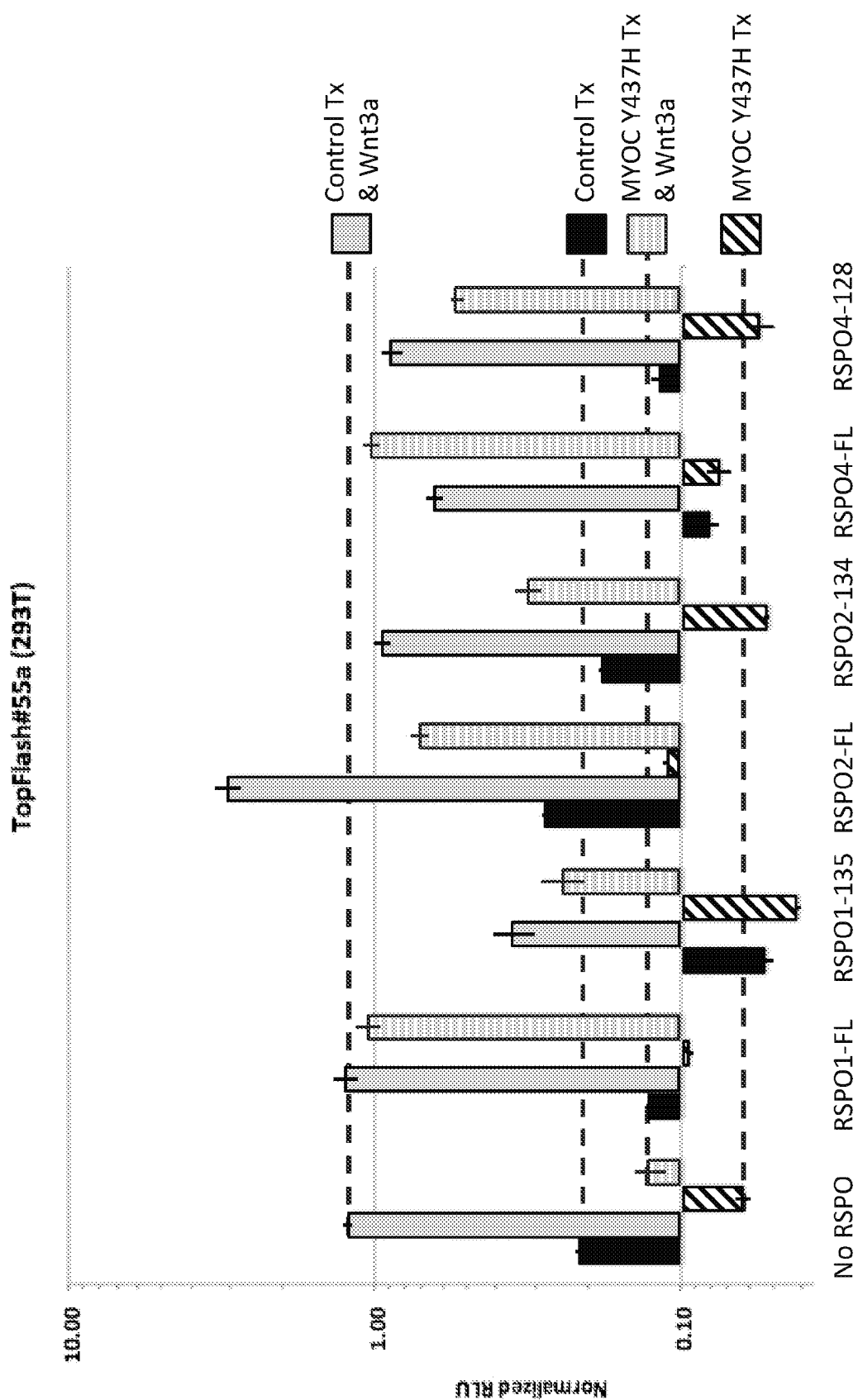

To test the effect of different RSPO family members on Wnt signaling, 293T cells were co-transfected with TOP-Flash reporter construct and wtMYOC ("MYOC") or Y437H MYOC, and also transfected with full length or partial RSPO1, RSPO2 or RSPO4 plasmids, as labeled in FIG. 16 (see FIG. 12 for depiction of RSPO1, 2, 3, and 4 truncated forms). Wnt signaling was amplified after addition of recombinant mouse Wnt3a (400 ng/ml) and measured by TOP-Flash assay. Luciferase activity (mean±SD, n=3) was measured post transfection and was normalized to the transfection control of constitutively expressed *Renilla* luciferase level.

The results of these studies are shown in FIG. 16. These results indicate that full-length and truncated RSPO1, 2, and 4 also had Wnt restoring activity with full-length RSPOs exhibiting more potent activity than truncated forms. All RSPO family members and forms worked with Wnt3a.

SEQUENCES

RSPO3 polypeptide sequence (signal sequence underlined)
(SEQ ID NO: 1)
<u>MHLRLISWLFIILNFMEYIGS</u>QNASRGRRQRRMHPNVSQGCQGGCATCSD
YNGCLSCKPRLFFALERIGMKQIGVCLSSCPSGYYGTRYPDINKCTKCKA
DCDTCFNKNFCTKCKSGFYLHLGKCLDNCPEGLEANNHTMECVSIVHCEV
SEWNPWSPCTKKGKTCGFKRGTETRVREIIQHPSAKGNLCPPTNETRKCT
VQRKKCQKGERGKKGRERKRKKPNKGESKEAIPDSKSLESSKEIPEQREN
KQQQKKRKVQDKQKSVSVSTVH RSPO3 polynucleotide sequence
(SEQ ID NO: 2)
ATGCACTTGCGACTGATTTCTTGGCTTTTTATCATTTTGAACTTTATGGA
ATACATCGGCAGCCAAAACGCCTCCCGGGGAAGGCGCCAGCGAAGAATGC
ATCCTAACGTTAGTCAAGGCTGCCAAGGAGGCTGTGCAACATGCTCAGAT
TACAATGGATGTTTGTCATGTAAGCCCAGACTATTTTTTGCTCTGGAAAG
AATTGGCATGAAGCAGATTGGAGTATGTCTCTCTTCATGTCCAAGTGGAT
ATTATGAACTCGATATCCAGATATAAATAAGTGTACAAAATGCAAAGCT
GACTGTGATACCTGTTTCAACAAAAATTTCTGCACAAAATGTAAAAGTGG
ATTTTACTTACACCTTGGAAAGTGCCTTGACAATTGCCCAGAAGGGTTGG
AAGCCAACAACCATACTATGGAGTGTGTCAGTATTGTGCACTGTGAGGTC
AGTGAATGGAATCCTTGGAGTCCATGCACGAAGAAGGGAAAAACATGTGG
CTTCAAAAGAGGGACTGAAACACGGGTCCGAGAAATAATACAGCATCCTT
CAGCAAAGGGTAACCTGTGTCCCCCAACAAATGAGACAAGAAAGTGTACA
GTGCAAAGGAAGAAGTGTCAGAAGGGAGAACGAGGAAAAAAGGAAGGGA
GAGGAAAAGAAAAAAACCTAATAAAGGAGAAAGTAAAGAAGCAATACCTG
ACAGCAAAAGTCTGGAATCCAGCAAAGAAATCCCAGAGCAACGAGAAAAC
AAACAGCAGCAGAAGAAGCGAAAAGTCCAAGATAAACAGAAATCGGTATC
AGTCAGCACTGTACACTAG MYOC polypeptide sequence
(SEQ ID NO: 3)
MRFFCARCCSFGPEMPAVQLLLLACLVWDVGARTAQLRKANDQSGRCQYT
FSVASPNESSCPEQSQAMSVIHNLQRDSSTQRLDLEATKARLSSLESLLH
QLTLDQAARPQETQEGLQRELGTLRRERDQLETQTRELETAYSNLLRDKS
VLEEEKKRLRQENENLARRLESSSQEVARLRRGQCPQTRDTARAVPPGSR
EVSTWNLDTLAFQELKSELTEVPASRILKESPSGYLRSGEGDTGCGELVW
VGEPLTLRTAETITGKYGVWMRDPKPTYPYTQETTWRIDTVGTDVRQVFL
YDLISQFMQGYPSKVHILPRPLESTGAVVYSGSLYFQGAESRTVIRYELN
TETVKAEKEIPGAGYHGQFPYSWGGYTDIDLAVDEAGLWVIYSTDEAKGA
IVLSKLNPENLELEQTWETNIRKQSVANAFIICGTLYTVSSYTSADATVN
FAYDTGTGISKTLTIPFKNRYKYSSMIDYNPLEKKLFAWDNLNMVTYDIK
LSKM MYOC cDNA sequence
(SEQ ID NO: 4)
ATGAGGTTCTTCTGTGCACGTTGCTGCAGCTTTGGGCCTGAGATGCCAGC
TGTCCAGCTGCTGCTTCTGGCCTGCCTGGTGTGGGATGTGGGGGCCAGGA
CAGCTCAGCTCAGGAAGGCCAATGACCAGAGTGGCCGATGCCAGTATACC
TTCAGTGTGGCCAGTCCCAATGAATCCAGCTGCCCAGAGCAGAGCCAGGC
CATGTCAGTCATCCATAACTTACAGAGAGACAGCAGCACCCAACGCTTAG
ACCTGGAGGCCACCAAAGCTCGACTCAGCTCCCTGGAGAGCCTCCTCCAC
CAATTGACCTTGGACCAGGCTGCCAGGCCCCAGGAGACCCAGGAGGGGCT
GCAGAGGGAGCTGGGCACCCTGAGGCGGGAGCGGGACCAGCTGGAAACCC
AAACCAGAGAGTTGGAGACTGCCTACAGCAACCTCCTCCGAGACAAGTCA
GTTCTGGAGGAAGAGAAGAAGCGACTAAGGCAAGAAAATGAGAATCTGGC
CAGGAGGTTGGAAAGCAGCAGCCAGGAGGTAGCAAGGCTGAGAAGGGGCC
AGTGTCCCCAGACCCGAGACACTGCTCGGGCTGTGCCACCAGGCTCCAGA
GAAGTTTCTACGTGGAATTTGGACACTTTGGCCTTCCAGGAACTGAAGTC
CGAGCTAACTGAAGTTCCTGCTTCCCGAATTTTGAAGGAGAGCCCATCTG
GCTATCTCAGGAGTGGAGAGGGAGACACCGGATGTGGAGAACTAGTTTGG
GTAGGAGAGCCTCTCACGCTGAGAACAGCAGAAACAATTACTGGCAAGTA
TGGTGTGTGGATGCGAGACCCAAGCCCACCTACCCCTACACCCAGGAGA
CCACGTGGAGAATCGACACAGTTGGCACGGATGTCCGCCAGGTTTTTGAG
TATGACCTCATCAGCCAGTTTATGCAGGGCTACCCTTCTAAGGTTCACAT
ACTGCCTAGGCCACTGGAAAGCACGGGTGCTGTGGTGTACTCGGGGAGCC
TCTATTTCCAGGGCGCTGAGTCCAGAACTGTCATAAGATATGAGCTGAAT
ACCGAGACAGTGAAGGCTGAGAAGGAAATCCCTGGAGCTGGCTACCACGG
ACAGTTCCCGTATTCTTGGGGTGGCTACACGGACATTGACTTGGCTGTGG
ATGAAGCAGGCCTCTGGGTCATTTACAGCACCGATGAGGCCAAAGGTGCC
ATTGTCCTCTCCAAACTGAACCCAGAGAATCTGGAACTCGAACAAACCTG
GGAGACAAACATCCGTAAGCAGTCAGTCGCCAATGCCTTCATCATCTGTG
GCACCTTGTACACCGTCAGCAGCTACACCTCAGCAGATGCTACCGTCAAC
TTTGCTTATGACACAGGCACAGGTATCAGCAAGACCCTGACCATCCCATT
CAAGAACCGCTATAAGTACAGCAGCATGATTGACTACAACCCCCTGGAGA
AGAAGCTCTTTGCCTGGGACAACTTGAACATGGTCACTTATGACATCAAG
CTCTCCAAGATGTAG MYOC shRNA Target sequences
(SEQ ID NO: 5)
GGCCATGTCAGTCATCCAT (SEQ ID NO: 6)
QAMSVIH shRNA Loop sequence
(SEQ ID NO: 7)
AATAGTGAAGCCACAGATGTATT RSPO1 polypeptide sequence (signal sequence underlined)
(SEQ ID NO: 8)
MRLGLCVVALVLSWTHLTISSRGIKGKRQRRISAEGSQACAKGCELCSEV
NGCLKCSPKLFILLERNDIRQVGVCLPSCPPGYFDARNPDMNKCIKCKIE
HCEACFSHNFCTKCKEGLYLHKGRCYPACPEGSSAANGTMECSSPAQCEM
SEWSPWGPCSKKQQLCGFRRGSEERTRRVLHAPVGDHAACSDTKETRRCT
VRRVPCPEGQKRRKGGQGRRENANRNLARKESKEAGAGSRRRKGQQQQQQ
QGTVGPLTSAGPA RSPO2 polypeptide sequence (signal sequence underlined)
(SEQ ID NO: 9)
MQFRLFSFALIILNCMDYSHCQGNRWRRSKRASYVSNPICKGCLSCSKDN
GCSRCQQKLFFFLRREGMRQYGECLHSCPSGYYGHRAPDMNRCARCRIEN
CDSCFSKDFCTKCKVGFYLHRGRCFDECPDGFAPLEETMECVEGCEVGHW
SEWGTCSRNNRTCGFKWGLETRTRQIVKKPVKDTILCPTIAESRRCKMTM
RHCPGGKRTPKAKEKRNKKKKRKLIERAQEQHSVFLATDRANQ RSPO4 polypeptide sequence (signal sequence underlined)
(SEQ ID NO: 10)
MRAPLCLLLLVAHAVDMLALNRRKKQVGTGLGGNCTGCIICSEENGCSTC
QQRLFFFLRREGIRQYGKCLHDCPPGYFGIRGQEVNRCKKCGATCESCFS
QDFCIRCKRQFYLYKGKCLPTCPPGTLAHQNTRECQGECELGPWGGWSPC
THNGKTCGSAWGLESRVREAGRAGHEEAATCQVLSESRKCPIQRPCPGER
SPGQKKGRKDRRPRKDRKLDRRLDVRPRQPGLQP RSPO1 truncation 1-135 polypeptide sequence (signal sequence underlined)
(SEQ ID NO: 11)
MRLGLCVVALVLSWTHLTISSRGIKGKRQRRISAEGSQACAKGCELCSEV
NGCLKCSPKLFILLERNDIRQVGVCLPSCPPGYFDARNPDMNKCIKCKIE
HCEACFSHNFCTKCKEGLYLHKGRCYPACPEGSSA RSPO1 truncation 1-206 polypeptide sequence (signal sequence underlined)
(SEQ ID NO: 12)
MRLGLCVVALVLSWTHLTISSRGIKGKRQRRISAEGSQACAKGCELCSEV
NGCLKCSPKLFILLERNDIRQVGVCLPSCPPGYFDARNPDMNKCIKCKIE
HCEACFSHNFCTKCKEGLYLHKGRCYPACPEGSSAANGTMECSSPAQCEM
SEWSPWGPCSKKQQLCGFRRGSEERTRRVLHAPVGDHAACSDTKETRRCT
VRRVPC RSPO2 truncation 1-134 polypeptide sequence (signal sequence underlined)
(SEQ ID NO: 13)
MQFRLFSFALIILNCMDYSHCQGNRWRRSKRASYVSNPICKGCLSCSKDN
GCSRCQQKLFFFLRREGMRQYGECLHSCPSGYYGHRAPDMNRCARCRIEN
CDSCFSKDFCTKCKVGFYLHRGRCFDECPDGFAP RSPO2 truncation 1-203 polypeptide sequence (signal sequence underlined)
(SEQ ID NO: 14)
MQFRLFSFALIILNCMDYSHCQGNRWRRSKRASYVSNPICKGCLSCSKDN
GCSRCQQKLFFFLRREGMRQYGECLHSCPSGYYGHRAPDMNRCARCRIEN
CDSCFSKDFCTKCKVGFYLHRGRCFDECPDGFAPLEETMECVEGCEVGHW
SEWGTCSRNNRTCGFKWGLETRTRQIVKKPVKDTILCPTIAESRRCKMTM
RHC RSPO3 truncation 1-135 polypeptide sequence (signal sequence underlined)
(SEQ ID NO: 15)
MHLRLISWLFIILNFMEYIGSQNASRGRRQRRMHPNVSQGCQGGCATCSD
YNGCLSCKPRLFFALERIGMKQIGVCLSSCPSGYYGTRYPDINKCTKCKA
DCDTCFNKNFCTKCKSGFYLHLGKCLDNCPEGLEA RSPO3 truncation 1-146 polypeptide sequence (signal sequence underlined)
(SEQ ID NO: 16)
MHLRLISWLFIILNFMEYIGSQNASRGRRQRRMHPNVSQGCQGGCATCSD
YNGCLSCKPRLFFALERIGMKQIGVCLSSCPSGYYGTRYPDINKCTKCKA
DCDTCFNKNFCTKCKSGFYLHLGKCLDNCPEGLEANNHTMECVSIV RSPO3 truncation 1-206 polypeptide sequence (signal sequence underlined)
(SEQ ID NO: 17)
MHLRLISWLFIILNFMEYIGSQNASRGRRQRRMHPNVSQGCQGGCATCSD
YNGCLSCKPRLFFALERIGMKQIGVCLSSCPSGYYGTRYPDINKCTKCKA
DCDTCFNKNFCTKCKSGFYLHLGKCLDNCPEGLEANNHTMECVSIVHCEV
SEWNPWSPCTKKGKTCGFKRGTETRVREIIQHPSAKGNLCPPTNETRKCT
VQRKKC RSPO4 truncation 1-128 polypeptide sequence (signal sequence underlined)
(SEQ ID NO: 18)
MRAPLCLLLLVAHAVDMLALNRRKKQVGTGLGGNCTGCIICSEENGCSTC
QQRLFLFIRREGIRQYGKCLHDCPPGYFGIRGQEVNRCKKCGATCESCFS
QDFCIRCKRQFYLYKGKCLPTCPPGTLA RSPO4 truncation 1-195 polypeptide sequence (signal sequence underlined)
(SEQ ID NO: 19)
MRAPLCLLLLVAHAVDMLALNRRKKQVGTGLGGNCTGCIICSEENGCSTC
QQRLFLFIRREGIRQYGKCLHDCPPGYFGIRGQEVNRCKKCGATCESCFS
QDFCIRCKRQFYLYKGKCLPTCPPGTLAHQNTRECQGECELGPWGGWSPC
THNGKTCGSAWGLESRVREAGRAGHEEAATCQVLSESRKCPIQRP Mutated ITR polynucleotide sequence
(SEQ ID NO: 20)
CACTCCCTCTCTGCGCGCTCGCTCGCTCACTGAGGCCGGGCGACCAAAGG
TCGCCCACGCCCGGGCTTTGCCCGGGCG MYOC370L forward mutagenesis primer (substitution is underlined)
(SEQ ID NO: 21)
ACCACGGACAGTTCCTGTATTCTTGGGGTGG

SEQUENCES

MYOC370L reverse mutagenesis primer (substitution is underlined)

(SEQ ID NO: 22)

CCACCCCAAGAATACAGGAACTGTCCGTGGT

MYOCY437H forward mutagenesis primer (substitution is underlined)

(SEQ ID NO: 23)

TCTGTGGCACCTTGCACACCGTCAGCAGC

MYOCY437H reverse mutagenesis primer (substitution is underlined)

(SEQ ID NO: 24)

GCTGCTGACGGTGTGCAAGGTGCCACAGA

---

What is claimed is:

1. A method for treating myocilin (MYOC) glaucoma associated with a mutation in the myocilin in a human, comprising directly administering to the eye of the human an agent that increases Wnt signaling in the eye of the human, wherein the agent is a recombinant adeno-associated virus (rAAV) particle comprising a vector comprising a nucleic acid encoding RSPO1, RSPO2, RSPO3, or RSPO4, wherein the nucleic acid is operably linked to a promoter capable of expressing the RSPO1, the RSPO2, the RSPO3, or the RSPO4 in the eye of the human, wherein the rAAV particle comprises an AAV serotype 2 (AAV2) capsid, and wherein the mutation in the myocilin comprises one or more amino acid substitutions selected from the group consisting of E323K, K398R, Q368X, G364V, P370L, D380A, K423E, Y437H, and I477S.

2. The method of claim 1, the rAAV particle comprises the vector encoding the RSPO1, the RSPO2, the RSPO3, or the RSPO4, and the vector further encodes a MYOC RNAi operably linked to a second promoter, which targets expression of the myocilin in the eye.

3. The method of claim 2, wherein the RNAi is a small inhibitory RNA (siRNA), a micro RNA (miRNA), or a small hairpin RNA (shRNA).

4. The method of claim 2, wherein the RNAi is a shRNA.

5. The method of claim 4, wherein the MYOC shRNA targets the nucleic acid sequence encoding the amino acid sequence of SEQ ID NO:6.

6. The method of claim 4, wherein the MYOC shRNA comprises a loop sequence as set forth in SEQ ID NO: 7.

7. The method of claim 2, wherein the second promoter is a hybrid chicken (CBA) promoter or a RNA polymerase III promoter.

8. The method of claim 1, wherein the MYOC glaucoma is primary open-angle glaucoma (POAG) or the juvenile form of primary open angle glaucoma (JOAG).

9. The method of claim 1, wherein the vector encodes the RSPO1, and wherein the RSPO1 is a human RSPO1.

10. The method of claim 1, wherein the vector encodes the RSPO1, and wherein the RSPO1 comprises the amino acid sequence of SEQ ID NO: 8, SEQ ID NO: 11, or SEQ ID NO: 12.

11. The method of claim 1, wherein the vector encodes the RSPO2, and wherein the RSPO2 is a human RSPO2.

12. The method of claim 1, wherein the vector encodes the RSPO2, and wherein the RSPO2 comprises the amino acid sequence of SEQ ID NO:9, SEQ ID NO: 13, or SEQ ID NO: 14.

13. The method of claim 1, wherein the vector encodes the RSPO3, and wherein the RSPO3 is a human RSPO3.

14. The method of claim 1, wherein the vector encodes the RSPO3, and wherein the RSPO3 comprises the amino acid sequence of SEQ ID NO:1, SEQ ID NO: 15, SEQ ID NO: 16, or SEQ ID NO: 17.

15. The method of claim 14, wherein the RSPO3 comprises the amino acid sequence of SEQ ID NO: 1.

16. The method of claim 1, wherein the vector encodes the RSPO4, and wherein the RSPO4 is a human RSPO4.

17. The method of claim 1, wherein the vector encodes the RSPO4, and the RSPO4 comprises the amino acid sequence of SEQ ID NO: 10, SEQ ID NO: 18, or SEQ ID NO: 19.

18. The method of claim 1, wherein the promoter is capable of expressing the RSPO1, the RSPO2, the RSPO3, or the RSPO4 in cells of the trabecular meshwork.

19. The method of claim 1, wherein the promoter is a hybrid chicken β-actin (CBA) promoter.

20. The method of claim 1, wherein AAV2 capsid comprising an amino acid substitution at one or more of positions of R484, R487, K527, K532, R585 and R588, numbering based on VP1 of the AAV2.

21. The method of claim 1, wherein the AAV serotype 2 capsid comprises an AAV2 capsid protein comprising a R471A amino acid substitution, numbering relative to the AAV2 VP1.

22. The method of claim 1, wherein the vector comprises AAV1, AAV2, AAV3, AAV4, AAV5, AAV6, AAV7, AAV8, AAVrh8, AAVrh8R, AAV9, AAV10, AAVrh10, AAV11, AAV 12, a goat AAV, a bovine AAV, or a mouse AAV inverted terminal repeats (ITRs).

23. The method of claim 22, wherein the vector comprises the AAV serotype 2 ITRs.

24. The method of claim 23, wherein the AAV2 capsid comprises an AAV2 capsid protein comprising a R471A amino acid substitution, numbering relative to the AAV2 VP1.

25. The method of claim 1, wherein the rAAV particle comprises one or more ITRs from a different AAV serotype than the capsid of the rAAV particle.

26. The method of claim 1, wherein at least 1×10⁹ genome copies of the rAAV particle are administered to the eye.

27. The method of claim 1, wherein the rAAV particle is administered by at least one of intravitreal injection and intracameral injection.

28. The method of claim 1, wherein the rAAV particle is administered to more than one location of the eye.

29. The method of claim 1, wherein the rAAV particle is in a pharmaceutical composition.

30. The method of claim 1, wherein the myocilin mutation comprises a P370L amino acid substitution.

31. The method of claim 1, wherein the myocilin mutation comprises a Y437H amino acid substitution.

32. A method for treating MYOC glaucoma associated with a mutation in the myocilin in a human, comprising directly administering to the eye of the human a first rAAV particle comprising a first vector comprising a first nucleic acid encoding RSPO1, RSPO2, RSPO3, or RSPO4, and a second rAAV particle comprising a second vector comprising a second nucleic acid encoding a MYOC RNAi which targets expression of a myocilin in the human, wherein the first nucleic acid is operably linked to a first promoter capable of expressing the RSPO1, the RSPO2, the RSPO3, or the RSPO4 in the eye of the human, wherein the second nucleic acid is operably linked to a second promoter capable of expressing the MYOC RNAi in the eye of the human, wherein the first rAAV particle and the second rAAV particle comprise an AAV2 capsid, and wherein the mutation in the myocilin comprises one or more amino acid substitutions selected from the group consisting of E323K, K398R, Q368X, G364V, P370L, D380A, K423E, Y437H, and I477S.

33. The method of claim 32, wherein the MYOC glaucoma is POAG or the JOAG.

34. The method of claim 32, wherein the myocilin mutation comprises a P370L amino acid substitution.

35. The method of claim 32, wherein the myocilin mutation comprises a Y437H amino acid substitution.

36. The method of claim 32, wherein the first vector encodes the RSPO1, and wherein the RSPO1 is a human RSPO1.

37. The method of claim 32, wherein the first vector encodes the RSPO1, and wherein the RSPO1 comprises the amino acid sequence of SEQ ID NO: 8, SEQ ID NO: 11, or SEQ ID NO: 12.

38. The method of claim 32, wherein the first vector encodes the RSPO2, and wherein the RSPO2 is a human RSPO2.

39. The method of claim 32, wherein the first vector encodes the RSPO2, and wherein the RSPO1 comprises the amino acid sequence of SEQ ID NO:9, SEQ ID NO: 13, or SEQ ID NO: 14.

40. The method of claim 32, wherein the first vector encodes the RSPO3, and wherein the RSPO3 is a human RSPO3.

41. The method of claim 32, wherein the first vector encodes the RSPO3, and wherein the RSPO3 comprises the amino acid sequence of SEQ ID NO:1, SEQ ID NO: 15, SEQ ID NO: 16, or SEQ ID NO: 17.

42. The method of claim 41, wherein the RSPO3 comprises the amino acid sequence of SEQ ID NO: 1.

43. The method of claim 32, wherein the first vector encodes the RSPO4, and wherein the RSPO4 is a human RSPO4.

44. The method of claim 32, wherein the first vector encodes the RSPO3, and wherein the RSPO3 comprises the amino acid sequence of SEQ ID NO: 10, SEQ ID NO: 18, or SEQ ID NO: 19.

45. The method of claim 32, wherein the first promoter is capable of expressing the RSPO1, the RSPO2, the RSPO3, or the RSPO4 in cells of the trabecular meshwork.

46. The method of claim 32, wherein the first promoter is a hybrid chicken β-actin (CBA) promoter.

47. The method of claim 32, wherein the RNAi is a siRNA, a miRNA, or a shRNA.

48. The method of claim 32, wherein the RNAi is a shRNA.

49. The method of claim 48, wherein the MYOC shRNA targets the nucleic acid sequence encoding the amino acid sequence of SEQ ID NO:6.

50. The method of claim 49, wherein the MYOC shRNA comprises a loop sequence as set forth in SEQ ID NO: 7.

51. The method of claim 32, wherein the second promoter is a CBA promoter or a RNA polymerase III promoter.

52. The method of claim 32, wherein the AAV2 capsid comprises an amino acid substitution at one or more of positions of R484, R487, K527, K532, R585 and R588, numbering based on VP1 of the AAV2.

53. The method of claim 32, wherein the AAV serotype 2 capsid of the first rAAV particle and the second rAAV particle comprises an AAV2 capsid protein comprising a R471A amino acid substitution, numbering relative to the AAV2 VP1.

54. The method of claim 53, wherein the first vector and the second vector comprise the AAV serotype 2 ITRs.

55. The method of claim 32, wherein the first vector and/or the second vector comprises AAV1, AAV2, AAV3, AAV4, AAV5, AAV6, AAV7, AAV8, AAVrh8, AAVrh8R, AAV9, AAV10, AAVrh10, AAV11, AAV 12, a goat AAV, a bovine AAV, or a mouse AAV ITRs.

56. The method of claim 55, wherein the first vector and the second vector comprise the AAV serotype 2 ITRs.

57. The method of claim 32, wherein the first rAAV particle comprises one or more ITRs from a different AAV serotype than the capsid of the first rAAV particle, and/or the second rAAV particle comprises one or more ITRs from a different AAV serotype than the capsid of the second rAAV particle.

58. The method of claim 32, wherein at least $1\times10^9$ genome copies of the first rAAV particle and the second rAAV particle are administered to the eye.

59. The method of claim 32, wherein the first rAAV particle and the second rAAV particle are administered by at least one of intravitreal injection and intracameral injection.

60. The method of claim 32, wherein the first rAAV particle and the second rAAV particle are administered to more than one location of the eye.

61. The method of claim 32, wherein the first rAAV particle and the second rAAV particle are in a pharmaceutical composition.

* * * * *

UNITED STATES PATENT AND TRADEMARK OFFICE
CERTIFICATE OF CORRECTION

PATENT NO. : 10,821,193 B2
APPLICATION NO. : 15/511595
DATED : November 3, 2020
INVENTOR(S) : Peter Pechan et al.

Page 1 of 1

It is certified that error appears in the above-identified patent and that said Letters Patent is hereby corrected as shown below:

In the Claims

Claim 2, Column 81, Line 66: please replace "The method of claim 1, the rAAV particle" with --The method of claim 1, wherein the rAAV particle--;

Claim 20, Column 83, Lines 31-32: please replace "wherein AAV2 capsid comprising an amino acid" with --wherein the AAV2 capsid comprises an amino acid--;

Claim 20, Column 83, Lines 32-33: please replace "substitution at one or more of positions of R484" with --substitution at one or more of positions R484--;

Claim 39, Column 84, Line 35: please replace "encodes the RSPO2, and wherein the RSPO1 comprises" with --encodes the RSPO2, and wherein the RSPO2 comprises--; and Claim 52, Column 85, Lines 4-5: please replace "substitution at one or more of positions of R484" with --substitution at one or more of positions R484--.

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*